United States Patent
Ahmad et al.

(10) Patent No.: US 11,696,702 B2
(45) Date of Patent: Jul. 11, 2023

(54) BREATH ANALYSIS SYSTEM, DEVICE AND METHOD EMPLOYING NANOPARTICLE-BASED SENSOR

(71) Applicant: Invoy Holdings, LLC, Aliso Viejo, CA (US)

(72) Inventors: Lubna M. Ahmad, Chandler, AZ (US); Rhett L. Martineau, Chandler, AZ (US); Salman A. Ahmad, Chandler, AZ (US); Zachary Smith, Phoenix, AZ (US)

(73) Assignee: Invoy Holdings Inc., Irvine, CA (US)

(*) Notice: Subject to any disclaimer, the term of this patent is extended or adjusted under 35 U.S.C. 154(b) by 126 days.

(21) Appl. No.: 16/884,830

(22) Filed: May 27, 2020

(65) Prior Publication Data

US 2020/0281504 A1  Sep. 10, 2020

Related U.S. Application Data

(63) Continuation of application No. 15/156,188, filed on May 16, 2016, now Pat. No. 10,694,978.

(Continued)

(51) Int. Cl.
*A61B 5/08* (2006.01)
*A61B 5/097* (2006.01)

(52) U.S. Cl.
CPC .............. *A61B 5/082* (2013.01); *A61B 5/097* (2013.01); *A61B 2560/0214* (2013.01); *A61B 2562/0285* (2013.01)

(58) Field of Classification Search
CPC . A61B 5/082; A61B 5/097; A61B 2560/0214; A61B 2562/0285
See application file for complete search history.

(56) References Cited

U.S. PATENT DOCUMENTS

| 4,147,514 A | 4/1979 | Magers et al. |
| 4,844,867 A | 7/1989 | Bather |

(Continued)

FOREIGN PATENT DOCUMENTS

| EP | 1 524 522 | 4/2005 |
| WO | WO 03/039367 | 5/2003 |

(Continued)

OTHER PUBLICATIONS

"CMS Operator Guide", CMS Operator Training 0108, dated Apr. 19, 2002, in 10 pages. URL: http://www.buydraegertubes.com/ds/cms-ops-guide.pdf.

(Continued)

*Primary Examiner* — Dennis White
(74) *Attorney, Agent, or Firm* — Knobbe, Martens, Olson & Bear, LLP

(57) ABSTRACT

A system is provided that includes a portable measurement device for measuring acetone in a breath sample of a user. The measurement device comprises a housing, a user-direct breath input device for engaging in direct fluid communication with a respiratory tract of the user and receiving the breath sample from the respiratory tract, a flow path disposed within the housing, a nanoparticle-based sensor disposed in the housing in fluid communication with the flow path and at an intermediate location between the upstream end and the downstream end, and a flow control device disposed in the housing and in the flow path between the upstream end and the nanoparticle-based sensor that prevents flow of the breath sample in an upstream direction opposite the downstream direction.

14 Claims, 28 Drawing Sheets

Related U.S. Application Data

(60) Provisional application No. 62/161,872, filed on May 14, 2015.

(56) References Cited

U.S. PATENT DOCUMENTS

| | | | |
|---|---|---|---|
| 4,931,404 | A | 6/1990 | Kundu |
| 4,970,172 | A | 11/1990 | Kundu |
| 5,071,769 | A | 12/1991 | Kundu et al. |
| 5,174,959 | A | 12/1992 | Kundu et al. |
| 5,465,728 | A | 11/1995 | Phillips |
| 5,834,626 | A | 11/1998 | De Castro et al. |
| 6,010,459 | A | 1/2000 | Silkoff et al. |
| 6,067,989 | A | 5/2000 | Katzman |
| 6,190,858 | B1 | 2/2001 | Persaud |
| 6,206,837 | B1 | 3/2001 | Brugnoli |
| 6,221,026 | B1 | 4/2001 | Phillips |
| 6,234,006 | B1 | 5/2001 | Sunshine et al. |
| 6,254,547 | B1 | 7/2001 | Phillips |
| 6,454,723 | B1 | 9/2002 | Montagnino |
| 6,540,691 | B1 | 4/2003 | Phillips |
| 6,582,376 | B2 | 6/2003 | Baghdassarian |
| 6,599,253 | B1 | 7/2003 | Baum et al. |
| 6,607,387 | B2 | 8/2003 | Mault |
| 6,629,934 | B2 | 10/2003 | Mault et al. |
| 6,658,915 | B2 | 12/2003 | Sunshine et al. |
| 6,726,637 | B2 | 4/2004 | Phillips |
| 6,841,391 | B2 | 1/2005 | Lewis et al. |
| 6,981,947 | B2 | 1/2006 | Melker |
| 7,052,854 | B2 | 5/2006 | Melker et al. |
| 7,104,963 | B2 | 9/2006 | Melker et al. |
| 7,220,387 | B2 | 5/2007 | Flaherty et al. |
| 7,300,408 | B2 | 11/2007 | Hancock et al. |
| 7,364,551 | B2 | 4/2008 | Allen et al. |
| 7,533,558 | B2 | 5/2009 | Flaherty et al. |
| 7,794,994 | B2 | 9/2010 | Cranley et al. |
| 7,837,936 | B1 | 11/2010 | Martin |
| 7,920,998 | B2 | 4/2011 | Brown |
| 7,976,467 | B2 | 7/2011 | Young et al. |
| 8,021,308 | B2 | 9/2011 | Carlson et al. |
| 8,036,708 | B2 | 10/2011 | Oozeki |
| 8,286,088 | B2 | 10/2012 | Shaffer et al. |
| 8,287,454 | B2 | 10/2012 | Wolpert et al. |
| 8,342,178 | B2 | 1/2013 | Hengstenberg et al. |
| 8,399,837 | B2 | 3/2013 | Robbins et al. |
| 8,514,086 | B2 | 8/2013 | Harper et al. |
| 8,680,974 | B2 | 3/2014 | Meiertoberens et al. |
| 8,722,417 | B2 | 5/2014 | Ahmad |
| 8,816,862 | B2 | 8/2014 | Harper et al. |
| 8,848,189 | B2 | 9/2014 | Atkin et al. |
| 8,871,521 | B2 | 10/2014 | Akers, Jr. |
| 8,917,184 | B2 | 12/2014 | Smith et al. |
| 9,170,225 | B2 | 10/2015 | Dutta et al. |
| 9,173,595 | B2 | 11/2015 | Böhm et al. |
| 9,341,632 | B1 | 5/2016 | Ahmad et al. |
| 9,643,186 | B1 | 5/2017 | Ahmad et al. |
| 10,694,978 | B2 | 6/2020 | Ahmad et al. |
| 2003/0208133 | A1 | 11/2003 | Mault |
| 2004/0018114 | A1 | 1/2004 | Wang et al. |
| 2004/0236244 | A1 | 10/2004 | Allen et al. |
| 2007/0245810 | A1 | 10/2007 | Carter et al. |
| 2007/0258894 | A1 | 11/2007 | Melker et al. |
| 2008/0008666 | A1 | 1/2008 | Phillips |
| 2008/0053194 | A1 | 3/2008 | Ahmad |
| 2008/0056946 | A1 | 3/2008 | Ahmad |
| 2008/0234553 | A1 | 9/2008 | Urman et al. |
| 2009/0004054 | A1* | 1/2009 | Burke ............ G01N 33/4972 422/400 |
| 2009/0049890 | A1* | 2/2009 | Zhong ............ G01N 33/497 73/23.3 |
| 2009/0054799 | A1 | 2/2009 | Vrtis et al. |
| 2010/0301197 | A1 | 12/2010 | Boyle |
| 2011/0028091 | A1 | 2/2011 | Higgins et al. |
| 2011/0098590 | A1 | 4/2011 | Garbutt et al. |
| 2011/0244584 | A1 | 10/2011 | Haick et al. |
| 2012/0071737 | A1 | 3/2012 | Landini et al. |
| 2012/0295595 | A1 | 11/2012 | Gibori et al. |
| 2013/0231711 | A1 | 9/2013 | Kaib |
| 2013/0253358 | A1 | 9/2013 | Phillips |
| 2014/0276100 | A1 | 9/2014 | Satterfield et al. |
| 2014/0366610 | A1 | 12/2014 | Rodriguez |
| 2015/0073233 | A1 | 3/2015 | Rich et al. |
| 2015/0168307 | A1 | 6/2015 | Kück et al. |
| 2015/0289782 | A1 | 10/2015 | Peverall et al. |
| 2016/0146779 | A1 | 5/2016 | Gallagher et al. |
| 2016/0150995 | A1 | 6/2016 | Ratto et al. |
| 2016/0245797 | A1 | 8/2016 | Ahmad et al. |

FOREIGN PATENT DOCUMENTS

| | | | |
|---|---|---|---|
| WO | WO 03/039483 | 5/2003 | |
| WO | WO 2005/082234 | 9/2005 | |
| WO | WO 2010/094967 | 8/2010 | |
| WO | WO 2011/104567 | 9/2011 | |
| WO | WO-2013115933 A1 * | 8/2013 | ........... A61B 5/0059 |
| WO | WO 2013/164836 | 11/2013 | |
| WO | WO 2015/134390 | 9/2015 | |

OTHER PUBLICATIONS

"Figaro Gas Sensor TGS 822", Figaro Engineering Inc., Mar. 1987, in 10 pages.

"MiniMed 530G System User Guide", Medtronic MiniMed, Inc., 2012, in 312 pages.

Ahmad, L. et al., "Design of a Breath Ketone Sensor for Obesity Management", Poster Presentation, Fall Meeting of the Biomedical Engineering Society, 2004, in 3 pages.

Barnett, D. et al., "Breath acetone and blood sugar measurements in diabetes", Clinical Science, vol. 37 (1969), in 1 page.

Chakraborty, S. et al., "Detection of biomarker in breath: a step towards noninvasive diabetes monitoring", Current Science, vol. 94, Jan. 25, 2008, in 6 pages.

Chakraborty, S. et al., "Pt nanoparticle-based highly sensitive platform for the enzyme-free amperometric sensing of $H_2O_2$", Biosensors and Bioelectronics, vol. 24 (2009), in 5 pages.

Crofford, O. et al., "Acetone in Breath and Blood", Transactions of the American Clinical and Climatological Association, vol. 88 (1977), in 12 pages.

Diskin, A. et al., "Time variation of ammonia, acetone, isoprene and ethanol in breath: a quantitative SIFT-MS study over 30 days", Physiological Measurement, vol. 24 (2003), in 13 pages.

Dräger CMS Production Information (document properties of document indicate that the document was created on Dec. 1, 2008), in 4 pages. URL: http://www.draeger.com/sites/assets/PublishingImages/Products/cin_chip_measurement_system/US/cms-ds-pi-9044337-en-us.pdf.

DrägerTubes & Accuro Pump Production Information (document properties of document indicate that the document was created on Nov. 11, 2008), in 4 pages. URL: http://www.draeger.com/sites/assets/PublishingImages/Products/cin_accuro/US/081209-pi-DetectorTubes-22-10-2008-en.pdf.

Dubowski, K. et al., "Response of Breath-Alcohol Analyzers to Acetone: Further Studies", Journal of Analytical Toxicology, vol. 8, Sep./Oct. 1984, in 4 pages.

Gervais, T. et al., "Mass transport and surface reactions in microfluidic systems", Chemical Engineering Science, vol. 61 (2006), in 20 pages.

Gouma, P. et al., "A selective nanosensing probe for nitric oxide", Applied Physics Letters, vol. 93 (2008), in 3 pages.

Gouma, P. et al., "Nanosensor and Breath Analyzer for Ammonia Detection in Exhaled Human Breath", IEEE Sensors Journal, vol. 10, Jan. 2010, in 5 pages.

Ketonix US, "Ketonix 2015 Blue Specifications", 2015, in 2 pages. URL:https://www.ketonix.com/index.php/product-2/ketonix-2015-blue.

Ketonix, "Ketonix data for Michel Lundell", 2015, in 1 page. URL: https://www.ketonix.com.

Khan, A. et al. "Evaluation of a bedside blood ketone sensor: the effects of acidosis, hyperglycaemia and acetoacetate on sensor

(56) References Cited

OTHER PUBLICATIONS performance", Diabetic Medicine, vol. 21 (2004), in 5 pages.
Kundu, S. et al., "Breath Acetone Analyzer: Diagnostic Tool to Monitor Dietary Fat Loss", Clinical Chemistry, vol. 39 (1993), in 6 pages.
Kundu, S. K. et al., "Novel Solid-Phase Assay of Ketone Bodies in Urine", Clinical Chemistry, vol. 37 (1991), in 5 pages.
Kupari, M. et al., "Breath Acetone in Congestive Heart Failure", the American Journal of Cardiology, vol. 76, Nov. 15, 1995, in 3 pages.
Landini, B. et al., "Breath Acetone Concentration Measured Using a Palm-Size Enzymatic Sensor System", IEEE Sensors Journal, vol. 9, Dec. 2009, in 6 pages.
Landini, B. et al., "Effect of Exhalation Variables on the Current Response of an Enzymatic Breath Acetone Sensing Device", IEEE Sensors Journal, vol. 10, Jan. 2010, in 6 pages.
Likhodii, S. et al., "Breath Acetone as a Measure of Systemic Ketosis Assessed in a Rat Model of the Ketogenic Diet", Clinical Chemistry, vol. 48 (2002), in 6 pages.
Loken, S. C., "Breath Acetone and Ketone Metabolism in Obese and Diabetic Mice", Diabetes, vol. 25 (1976), in 1 page.
Musa-Veloso, K. et al., "Breath acetone is a reliable indicator of ketosis in adults consuming ketogenic meals", the American Journal of Clinical Nutrition, vol. 76 (2002), in 6 pages.
Reungchaiwat, A. et al., "Home-made Detection Device for a Mixture of Ethanol and Acetone", Sensors, vol. 7 (2007), in 12 pages.
Schwarz, K. et al., "Breath acetone—aspects of normal physiology related to age and gender as determined in a PTR-MS study", Journal of Breath Research, vol. 3 (2009), in 9 pages.
Wang, L. et al., "An Acetone Nanosensor for Non-invasive Diabetes Detection", AIP Conferences Proceedings, 1137 (2009), in 4 pages.
Wang, L. et al., "Nanosensor Device for Breath Acetone Detection", Sensor Letters, vol. 8 (2010), in 4 pages.
Wang, L., "Tailored synthesis and characterization of selective metabolite-detecting nanoprobes for handheld breath analysis", Dissertation Ph. D. Thesis, Stony Brook University, Dec. 2008, in 127 pages.
Yadav, L. et al., "Non-Invasive Biosensor for Diabetes Monitoring", Asian Journal of Pharmaceutical and Clinical Research, vol. 7 (2014), in 5 pages.
Yoon, S. et al., "Active control of the depletion boundary layers in microfluidic electrochemical reactors", Lab on a Chip, vol. 6 (2006), in 9 pages.

\* cited by examiner

BREATH ANALYSIS SYSTEM, DEVICE AND METHOD EMPLOYING NANOPARTICLE-BASED SENSOR

INCORPORATION BY REFERENCE TO ANY PRIORITY APPLICATIONS

This application claims the benefit of U.S. application Ser. No. 15/156,188, filed May 16, 2016, which is hereby incorporated by reference in its entirety herein. This application claims the benefit of U.S. Provisional Application No. 62/161,872, filed May 14, 2015, which is hereby incorporated by reference in its entirety herein. Any and all applications for which a foreign or domestic priority claim is identified in the Application Data Sheet as filed with the present application are hereby incorporated by reference under 37 C.F.R. § 1.57.

FIELD

The present disclosure relates to breath measurement or analysis systems, devices and methods for measuring acetone in breath and, more specifically, to breath measurement systems, devices and methods that employ nanoparticle-based sensors.

BACKGROUND

Breath analysis for measuring chemical components or analytes in the breath offers important potential benefits over other alternative methods of analyte measurement, e.g., such as blood- or urine-based measurement. Such benefits include ease of use and patient or user compliance, particularly for home or other non-clinical use. Gaining patient compliance is generally far easier when the requirement is to exhale into a device, rather than drawing blood or obtaining a urine sample. Ease of handling the samples also is enhanced.

Hand-held or otherwise portable breath analysis devices afford the potential for even greater advantages. Such portability presents opportunities for extra-clinical applications, e.g., at home, office, gym, weight loss facility, and the like, and by the patient or user himself or herself, rather than by a trained clinician or technician. Portable breath sensing systems offer the potential for comfortable and more natural sampling to increase user adherence to a desired sampling schedule.

Although approximately 300 analytes have been identified in human breath, acetone is an important analyte that is particularly promising for practical and beneficial application. Acetone has been correlated with fat metabolism, which in turn is involved in physiological and pathophysiological phenomena ranging from weight loss to metabolic disorders. Measurement of breath acetone at levels or concentration ranges of interest, for example, can enable one to gain useful information about such factors as patient or user weight loss, and about such pathological states as diabetes mellitus, metabolic syndrome, and metabolic or ketoacidosis.

SUMMARY

The sensor can be a central component in portable breath analysis devices. The analyte or analytes of interest in breath analysis often are present only in very low concentrations, thus requiring highly sensitive sensors. The sensing task is made more difficult by the fact that, as noted above, breath typically has a range of chemical components in it, including a range of volatile organic compounds. In addition, breath is typically at or near saturation with humidity. These concerns and the plethora of potential inteferents make accurate and reliable detection of the target analyte challenging.

A variety of sensor technologies are known or have been theorized. Examples include thermo-electric sensors, pyro-electric sensors, electrochemical and enzyme sensors, and colorimetric sensors. Each of these sensor technologies has its own set of advantages, disadvantages, limitations and challenges.

With some sensor technologies, the sensor must be heated from a power or heat source prior to and as part of its operation. In the context of portable breath measurement devices, this usually requires that electrical circuitry and a suitable power source be provided.

In some portable breath measurement devices, the user positions the breath measurement device in contact with his or her mouth and exhales directly into the device. Where the sensor is heated, for example, as may be required with nanoparticle-based sensors, this places the heated sensor in fluid communication with the user's mouth and respiratory tract. In addition to the unwanted transfer of heat, such devices can present chemical toxicity risks. Electrical aspects of the breath measurement devices also can pose risks. Electrical anomalies can arise, for example, such as electrostatic discharge, power surges or spikes, overvoltage or overcurrent conditions, radiation, and the like. Thus, there is a need for breath measurement systems, devices and methods, and particularly breath measurement systems, devices and methods comprising nanoparticle-based sensors, for safety-related enhancements.

This disclosure includes a portable measurement device for measuring acetone in a breath sample of a user. The measurement device comprises a housing, a user-direct breath input device for engaging in direct fluid communication with a respiratory tract of the user and receiving the breath sample from the respiratory tract, a flow path disposed within the housing and comprising an upstream end and a downstream end, the upstream end of the flow path being in fluid communication with the user-direct breath input device, wherein in normal operation of the device the flow path directs the breath sample in a downstream direction from user-direct breath input device at the upstream end of the flow path and toward the downstream end, and a nanoparticle-based sensor disposed in the housing in fluid communication with the flow path and at an intermediate location between the upstream end and the downstream end. The device can further include a flow control device disposed in the housing and in the flow path between the upstream end and the nanoparticle-based sensor that prevents flow of the breath sample in an upstream direction opposite the downstream direction.

The user-direct breath input device may comprise a mouthpiece, a face mask, a nasal airway, and/or the like. The nanoparticle-based sensor can be disposed within the housing so that the nanoparticle-based sensor is substantially inaccessible to the user during use of the device. The intermediate location can include a compartment within the housing that comprises a detachable cover at an external location on the housing, and wherein the detachable cover is secured in a closed position. The detachable cover can include a fastener that requires a tool to detach from the housing.

In one embodiment, the housing comprises an insertion aperture, and the nanoparticle-based sensor can be disposed on an insertion member that can be inserted into and detached from the insertion aperture.

The flow control device may include at least one one-way valve, or at least two one-way valves. The one-way valve can be disposed adjacent to the breath input device. The one-way valve can be disposed at the upstream end of the flow path or, alternatively or in addition, the one-way valve may be disposed between the upstream end of the flow path and the intermediate location.

The measurement device can include a conditioning device disposed in the flow path between the upstream end of the flow path and the intermediate location, for example, disposed adjacent to the user-direct breath input device and/or disposed between the user-direct breath input device and the nanoparticle-based sensor.

The measurement device can include a conditioning device. The conditioning device can be disposed in the flow path downstream from the one-way valve and between the one-way valves if there is more than one. In either event, the conditioning device can be disposed in the flow path between the upstream end of the flow path and the nanoparticle-based sensor. Where there is a user-direct breath input device, the conditioning device can be disposed adjacent to the input device.

The measurement device can include a processor operatively coupled to the nanoparticle-based sensor for receiving a measurement signal representative of a concentration of the acetone in the breath sample from the nanoparticle-based sensor, and a communications device operatively coupled to the processor that receives the measurement signal from the processor and communicates the measurement signal externally from the measurement device.

In accordance with another aspect of the disclosure, a method is provided for sensing acetone in a breath sample of a user. The method can comprise providing a measurement device that comprises a housing, a flow path disposed within the housing, wherein the flow path comprises an upstream end and a downstream end, a user-direct breath input device disposed at the upstream end of the flow path that engages in direct fluid communication with a respiratory tract of the user and receiving the breath sample from the respiratory tract, and a nanoparticle-based sensor disposed in the housing in fluid communication with the flow path and at an intermediate location between the upstream end and the downstream end. During exhalation of the user into the user-direct breath input device, the method comprises using the measurement device to cause the breath sample to flow in the flow path in a downstream direction from the upstream end and toward the downstream end, and to contact the breath sample with the nanoparticle-based sensor so that the nanoparticle-based sensor senses the acetone in the breath sample. During an inhalation of the user from the user-direct breath input device, the method can further include using the measurement device to prevent flow of the breath sample in the flow path in an upstream direction from the downstream end and toward the upstream end.

In accordance with another aspect of the disclosure, a system is provided for sensing acetone in a breath sample of a user. The system can comprise a breath bag that contains the breath sample. The system can also include a portable measurement device that in turn comprises a housing, a flow path disposed within the housing and comprising an upstream end and a downstream end, wherein in normal operation of the measurement device the flow path directs the breath sample in the flow path in a downstream direction from the upstream end and toward the downstream end, a breath input coupler disposed at the upstream end of the flow path, the breath input coupler detachably engaging the breath bag and placing the breath sample in fluid communication with the flow path, and a nanoparticle-based sensor disposed in the housing in fluid communication with the flow path and at an intermediate location between the upstream end and the downstream end.

The breath bag can include a one-way valve. The breath input coupler can include a valve-opening mechanism that automatically opens the one-way valve when the breath bag is engaged with the breath input coupler. The one-way valve can include a valve closure, and the valve-opening mechanism can include a post that engages valve closure and move the valve closure to an open state.

The measurement device can include a flow control device disposed in the housing and in the flow path between the upstream end and the nanoparticle-based sensor that prevents flow of the breath sample in an upstream direction opposite the downstream direction.

The measurement device can also include a conditioning device disposed in the flow path between the upstream end of the flow path and the nanoparticle-based sensor. The conditioning device may advantageously be disposed adjacent to the user-direct breath input device.

In accordance with another aspect of the disclosure, a portable measurement device is provided for measuring acetone in a breath sample of a user contained within a breath bag. The measurement device can comprise a housing, and a flow path disposed within the housing and comprising an upstream end and a downstream end. In normal operation of the measurement device, the flow path directs the breath sample in the flow path in a downstream direction from the upstream end and toward the downstream end. The measurement device can also include a breath input coupler disposed at the upstream end of the flow path, the breath input coupler detachably engaging the breath bag and placing the breath sample in fluid communication with the flow path, and a nanoparticle-based sensor disposed in the housing in fluid communication with the flow path and at an intermediate location between the upstream end and the downstream end.

In accordance with still another aspect of the disclosure, a method is provided for sensing acetone in a breath sample of a user. The method can comprise inputting the breath sample into a breath bag. It can also include providing a portable measurement device comprising a housing, a flow path disposed within the housing and comprising an upstream end and a downstream end, wherein in normal operation of the measurement device the flow path directs the breath sample in the flow path in a downstream direction from the upstream end and toward the downstream end, a breath input coupler disposed at the upstream end of the flow path, and a nanoparticle-based sensor disposed in the housing in fluid communication with the flow path and at an intermediate location between the upstream end and the downstream end. The method can further include detachably engaging the breath bag to the breath input coupler, and using the measurement device to cause the breath sample to contact the nanoparticle-based sensor and to measure a concentration of the acetone in the breath sample.

In accordance with yet another aspect of the disclosure, a portable measurement device is provided for measuring acetone in a breath sample of a user. The measurement device comprises a housing, a flow path disposed within the housing and comprising an upstream end and a downstream end, the upstream end of the flow path being in fluid communication with the user-direct breath input device, wherein in normal operation of the device the flow path directs the breath sample in a downstream direction from user-direct breath input device at the upstream end of the flow path and toward the downstream end. The measurement device can also include a breath input device disposed at the upstream end of the flow path for inputting the breath sample, and a nanoparticle-based sensor subsystem disposed in the housing in fluid communication with the flow path and at an intermediate location between the upstream end and the downstream end. The measurement device can further include a power source that provides power to the nanoparticle-based subsystem, and an electrical safety device operatively coupled to the power source and the nanoparticle-based sensor subsystem that protects the nanoparticle-based power from an electrical threat.

Where the electrical threat comprises reverse polarity, the electrical safety device can include a diode. Where the electrical threat comprises an electrical fast transient, and the electrical safety device can include a capacitor. Where the electrical threat comprises an over voltage condition, the electrical safety device can include an over voltage protection circuit, for example, such as a voltage regulator. Where the electrical threat comprises an over current condition, the electrical safety device can include an over current protection circuit. Where the electrical threat comprises an electrostatic discharge, the electrical safety device can include an electrostatic discharge mitigation circuit.

In some devices wherein the nanoparticle-based sensor subsystem comprises a heating device, the electrical safety device can be operatively coupled to the power supply and to the heating device to protect the heating device from the electrical threat, and/or can be operatively coupled to the power supply and to the heating device to protect the nanoparticle-based sensor from the electrical threat.

In various embodiments, the power supply may comprise a battery, a DC source and/or an AC source.

BRIEF DESCRIPTION OF THE DRAWINGS

The accompanying drawings, which are incorporated in and constitute a part of the specification, illustrate certain embodiments and methods of the invention and, together with the general description given above and the detailed description of the embodiments and methods given below, serve to explain the principles of the invention. Of the drawings:

FIGS. 4A and 4B show side cutaway views of the proximal or upstream portion of the measurement device shown in FIG. 1, in which FIG. 4A is an expanded or exploded view, and FIG. 4B is an assembled view;

FIGS. 6A and 6B provide side cutaway views of a portion or portions of the measurement device of FIG. 1 indicated by lines 6-6 in FIG. 4A, which illustrates the operation of a one-way valve within the portion, in which FIG. 6A shows the valve in a closed state and FIG. 6B shows the valve in an open state;

FIGS. 9A and 9B provides side cutaway views of a portion or portions of the measurement device of FIG. 1, which illustrates the operation of another one-way valve within the portion, in which FIG. 9A shows the valve in a closed state and FIG. 9B shows the valve in an open state;

FIGS. 11A and 11B shows side cutaway views of a portion of the measurement device of FIG. 10 at a joinder between the mouthpiece or ferrule of a breath bag providing a breath sample and the proximal or upstream end of the measurement device, in which FIG. 11A shows the ferrule and proximal end of the measurement device in expanded or exploded form and FIG. 11B shows them in joined form;

DETAILED DESCRIPTION

Figure 1:
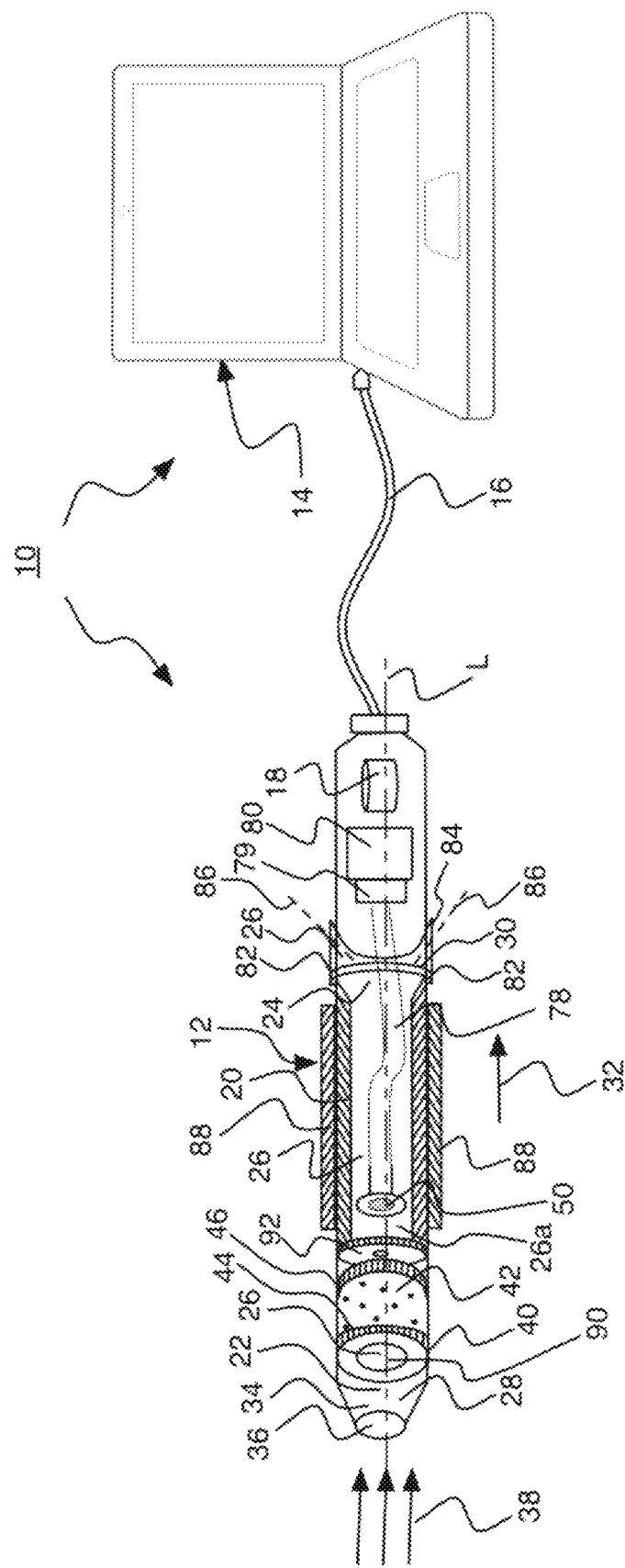
FIG. 1 is a pictorial view of a breath acetone measurement system according to one embodiment, including a partial cutaway view of a measurement device that is part of the system.

Reference will now be made in detail to different embodiments and methods as illustrated in the accompanying drawings, in which like reference characters designate like or corresponding parts throughout the drawings. It should be noted, however, that the invention in its broader aspects is not limited to the specific details, representative devices and methods, and illustrative examples shown and described in this section in connection with the embodiments and methods. The invention according to its various aspects is particularly pointed out and distinctly claimed in the attached claims read in view of this specification, and appropriate equivalents.

There are many instances in which it is desirable to sense or measure the presence and/or quantity of an analyte in a gas. "Analyte" as the term is used herein is used broadly to mean the chemical component or constituent that is sought to be sensed using devices and methods according to various aspects of the disclosure. An analyte may be or comprise an element, compound or other molecule, an ion or molecular fragment, or other substance that may be contained within a fluid. In some instances, embodiments and methods, there may be more than one analyte. The terms "sense," "analyze" and "measure," including their grammatically-based counterparts such as "sensing," "analysis" and "measurement," are used broadly and synonymously to mean detecting the presence of one or more analytes, or to measure the amount or concentration of the one or more analytes, or whether the analyte is within a particular concentration range, e.g., at least 1 part per million ("ppm").

Breath acetone measurement devices according to certain embodiments (including the associated communications device described herein below) are designed to be used and operated by a "user" (e.g., a dieting person, athlete, patient, etc.) whose acetone concentrations are being measured. They are amenable to use by the user alone, for example, without the presence or assistance of a friend, aid, nurse or clinical staff, etc. Such devices also are amenable, however, to use by a person other than the "user" whose acetone levels are being measured, for example, such as a coach, trainer, doctor, nurse, clinical technician, family member, friend and the like. Thus, although the "user" is the person whose breath acetone levels are being measured, the "user" may or may not also be the person who performs the manual commands and operations using the device, for example, wherein a patient exhales into a breath bag but a clinician or technician attaches the bag to the device housing and initiates the test. For simplicity and ease of illustration, throughout the detailed description section in this document, the "user" is assumed to be both the person whose breath acetone is being measured and the operator of the measurement device, even though this may not be and need not be the case in a given instance or application of the system.

Breath measurement devices according certain embodiments also are designed, sized and configured to be used not only in a clinical setting, (e.g., in a hospital, out-patient clinic, physician's office, nutritionist's office, diet treatment center, laboratory, and so on), but also in non-clinical settings, (e.g., the user's home, office, workplace, gym, while traveling, and so on). They can be "portable" in that they are sufficiently small and light weight that they can be conveniently lifted and carried and used by an individual at various locations. Although hand-held devices are included, this portability also includes table-top configurations and the like, provided they can be lifted and carried by an individual.

Acetone is an important analyte in breath measurement, and breath acetone measurement results or data can be extremely useful in managing the health and wellness of the user. Acetone is a member of a class of analytes known as ketones or, similarly, ketone bodies. Ketone bodies as the term is used in biochemistry and physiology means acetoacetate, β-hydroxybutyric acid (β-HBA"), β-hydroxybutyrate (β-HB") and acetone. Acetone is usually the only ketone body found in breath. Ketone bodies provide a supplementary or substitute form of energy that can be used during various metabolic states including stress, starvation, caloric regulation, or certain pathologies, e.g., such as certain diabetic states, epilepsy and others. Breath acetone levels, for example, often are elevated when any of these metabolic states are encountered. Not uncommonly with diabetic patients, for example, low insulin levels and elevated blood glucose levels result in high concentrations of ketones in the body. This sometimes causes a condition known as diabetic ketoacidosis ("DKA").

Patients in DKA commonly experience symptoms such as nausea, fatigue, and rapid breathing. The patient also emits a distinct fruity odor in the breath, which is attributable to acetone. Acetone is a volatile ketone body released into alveolar air. If left untreated, DKA can result in coma or even death. However, DKA often is preventable if ketone levels are monitored and treatment is sought when ketone counts are high.

In contrast, a condition known as hyperosmolar non-ketotic syndrome is where ketone levels in the body are subnormal, meaning that the body is not producing enough ketone bodies for normal functioning.

Ketone monitoring also is becoming recognized as a tool for nutritionists or health care professionals to monitor lipid metabolism during dieting. Several studies show that breath acetone concentrations represent lipid metabolism during a calorie deficit. Obesity has become increasingly prevalent and has now reached epidemic levels. It is consequently of great concern to healthcare professionals. Much effort has been invested in treating obesity and promoting healthy weight loss programs for obese individuals. For treatment of obesity, a sensor that measures fat burning would permit patients, doctors, nutrition advisors and the like to adjust weight management plans to individual physiology, lifestyles, user compliance with dietary restrictions, and the like.

A hand-held breath acetone analyzer also can be used to monitor ovulation. During ovulation, the body temperature increases and accordingly metabolic activity increases, which results in an increase in blood ketones and correspondingly breath acetone. Current ovulation tests involve either urine or blood analysis. A breath test, particularly a hand-held breath test, provides a compelling way for individuals to conveniently and simply monitor ovulation. Such a device may also monitor body temperature and be configured to track or log values over time so that the user may make informed decisions about family planning.

The current methods of ketone measurement are blood and urine analysis. The current blood tests typically are accurate, but their invasive nature is undesirable and frequently causes patients to delay treatment. Blood tests also are expensive, as a number of products are needed, including a lancet for blood sampling, test strips, a specialized device and batteries. Several studies show that urine analysis is not accurate.

A class of sensors referred to as "nanoparticle-based sensors" offers a potential sensor technology in various breath sensing applications. Nanoparticle-based sensors offer the potential of being sufficiently sensitive and selective for a number of breath sensing systems, while also being relatively reliable and inexpensive.

In operation, most nanoparticle-based sensors are most effective, and may only operate effectively, at elevated temperatures of about 150° C. (about 300° F.). They therefore are heated from a power or heat source prior to and as part of their use. For use in portable breath measurement devices, this requires that electrical circuitry and a suitable power source be provided.

Many portable breath measurement devices, and apparently nearly all of the relatively few that are commercially available, are designed such that the user positions the breath measurement device in contact with his or her mouth and exhales directly into the device. If such direct-contact devices are to employ a nanoparticle-based sensor, this places the heated sensor in fluid communication with the user's mouth and respiratory tract. Even though under normal operation the user is instructed only to exhale into the device, if the heat from the sensor is sufficiently substantial, it may be transported to the user's mouth and possibly his or her respiratory tract, e.g., by radiant transport, where it can cause irritation or personal injury. If the user inadvertently or otherwise inhales during the procedure, he or she may greatly increase that risk of exposure, e.g., by convecting the heat and associated air into his or her mouth and respiratory tract.

At elevated temperatures commonly encountered with nanoparticle-based sensors, materials from the sensor material itself, or from the material in the device in the vicinity of the sensor, can vaporize or degas, thereby presenting potentially harmful or toxic materials into the gas stream. These toxic materials also can be inhaled during use of the device, thus entering the user's mouth and potentially his or her respiratory tract and thereby causing injury.

Electrical aspects of the breath measurement devices also pose risks. Electrical anomalies can arise, for example, such as electrostatic discharge, power surges or spikes, overvoltage or overcurrent conditions, radiation, and the like. Such anomalies can present risks through their impact on the device, for example, such as causing aberrant measurement results or damage to the device, and they may pose threats of personal discomfort or injury to the user, such as burns, electrical shock, and the like.

System with User-Direct Breath Sample Input

The systems and methods described in this disclosure can work in conjunction with software systems and mobile devices, such as the mobile device shown in FIG. 1. Exemplary software systems are described, for example, in U.S. Pat. No. 9,341,632, entitled "Ketone Measurement System Capable of Detecting Correlations Between Measurements and User Behaviors," and U.S. patent application Ser. No. 15/040,790, filed Feb. 10, 2016, entitled "Method and Apparatus for Rapid Quantification of an Analyte in Breath," the entirety of both of which is hereby incorporated by reference as if fully set forth herein.

In some embodiments, a system 10 is provided for measuring acetone in a breath sample of a user and appropriately reporting or storing the measured result or results.

System 10 comprises a portable breath measurement device or apparatus 12 and an electronic or communications device 14. Measurement device 12 is useful for analyzing the breath sample to measure the acetone in it. Electronic or communications device 14 is operatively coupled to the measurement device 12 to selectively receive the measurement result from device 12 and store it, process it, and/or communicate it to another device, such as a remote system, network, central database, a cloud application, and/or the like. Electronic or communications device may comprise, e.g., a computer, laptop, tablet computer, cellular phone, a smart phone and/or the like. Measurement device 12 can be detachably coupled to electronic device 14 in this embodiment, for example, via a universal serial bus ("USB") or similar adapter cable 16 that allows measurement results data to be transferred from measurement device 12 to electronic device 14, and for electrical power to be supplied to measurement device 12, to operate the device or to charge a battery pack 18 that in turn provides operational power to device 12, or a combination of these.

Measurement device 12 comprises a housing 20 that, in this embodiment, includes a tubular or substantially cylindrical body. Housing 20 may be constructed of a rigid material that maintains its stiffness and structural integrity under the operating conditions as described herein, and which can maintain its external temperature in a range so that a user may hold the device without discomfort or injury during its operation. Housing 20 has an upstream end 22 and a downstream end 24.

Housing 20 also comprises a flow path 26 disposed within housing 20. Flow path 26 comprises an upstream end 28 corresponding to housing upstream end 22 and a downstream end 38 corresponding to housing downstream end 24. The direction of flow from upstream end 28 to downstream end 30 is referred to herein as the downstream direction 32. The direction directly opposite to the downstream direction, i.e., from the downstream end 30 to the upstream end 28 is referred to herein as the upstream direction.

The system may include a user-direct breath input device (sometimes referred to herein as a conduit) that facilitates the input of the breath sample into the flow channel directly from the respiratory tract of the user, e.g., by exhaling directly into device 12. The breath input device may comprise any one of a number of devices that is configured to provide the breath sample at the upstream end of the flow path so that the breath sample can be flowed into the flow path. Examples include a mouthpiece, face mask, breathing tube, nasal airway, and/or the like. In direct breath input designs, the system may include a mouthpiece into which the user can directly exhale. A face mask may be useful or in some cases even necessary, for example, if the user is unconscious, has a mouth injury or obstruction, or is otherwise experiencing difficulty with forced expiration through the oral cavity.

In system 10, the breath input device of measurement device 12 comprises a mouthpiece 34 affixed to the proximal or upstream end 22 of housing 20. (Incidentally, for ease and simplicity of description, and viewing the measurement device from the perspective of the user and the breath sample flow regime during normal use and operation, components and features of measurement device 12 and the other measurement devices described herein are referred to as "proximal" if they are relatively nearer to the upstream end of the housing and the flow path, and they are referred to as "distal" if they are relatively nearer to the downstream end of housing and flow path.)

Mouthpiece 34 at its proximal end has an opening 36 for entry of the breath exhaled from the user. The direction of the breath as it is inputted into mouthpiece 34 is shown by the arrows at 38. Mouthpiece 34 at a distal end 40 is coupled to the substantially cylindrical body of housing 20. Upstream end 28 of flow path 26 is in fluid communication with the interior or flow channel of mouthpiece 26.

In some systems, the measurement device may include a conditioning device that conditions the breath sample as it is inputted into flow path 26 and prior to its sensing or analyte measurement. The conditioning device may condition the breath sample, for example, for temperature, humidity, flow rate, flow velocity, pressure, concentration, interferents, or some combination thereof. Parameters such as, for example, temperature, pressure, water vapor content, and/or flow rate may significantly impact the ability of chemical sensors to reproducibly sense the concentration of an analyte.

Exhaled human breath usually contains a large amount of water vapor, and semiconducting nanoparticles in general are highly sensitive to the moisture content of the gas sample. In detecting analytes at low concentrations, which is the case for breath analysis, water vapor can obscure the response of the sensor to the analyte, either completely destroying the ability of the sensor to measure the analyte of interest or significantly deteriorating its performance. Addressing the moisture level of breath samples is challenging, e.g., because the water vapor content of breath is a relatively large portion of the total content. Compared to analytes of interest which may have concentrations in the parts per billion or low parts per million, water vapor content in exhaled human breath is measured in the parts per hundred. If a given sensor technology has significant response to water vapor, it may be necessary to both drastically reduce water vapor content in a sensed gas stream while simultaneously retaining a sufficient portion of the analyte of interest. Furthermore, the elevated temperature of exhaled human breath compared to common ambient room temperatures means that at least a portion of the water vapor in exhaled breath will likely condense. Condensation in flow circuits, electrical systems, and onto sensor elements or gas processing components can complicate a sensing system significantly. Many breath analytes of interest, including acetone, are attracted to liquid water such that condensation will also affect the amount of analyte that ultimately reaches the detector.

A given sensor design also may have an operating range that comprises a specific, bounded range of concentrations at which the sensor operates, or in which it operates optimally, or so that amplification or other adjustment of the analyte concentration is desired. Similarly, the presence of interferents, e.g., certain chemical components other than the target analyte or analytes that interfere with the measurement attributable to the target analyte or analytes, may create obstacles so that it is necessary or desirable to reduce the concentration or presence of one or more of these interferents.

The conditioning device may comprise a sorbent trap for reducing the concentration of or removing unwanted interferents. The sorbent trap may be or comprise one of a porous organic polymer (such as 2,6-diphenylene oxide "Tenax TA", 2,6-diphenylene oxide and graphite "Tenax GR", "Chromosorb" or "Porapak"), a graphitized carbon black (such as "Carbotrap", "Carbopack", "Carbograph"), a carbon molecular sieve (such as "Spherocarb", "Carbosieve", "Carboxen", molecular sieve 3A, 4A, 5A, 13X, etc., "Unicarb"), a carbon nanotube device or other nanostructured carbon, or any other activated carbon or adsorbent resin (such as XAD-2 "Amberlite" and "Anasorb CSC").

The conditioning device also may consist of or comprise a flow regulation device. Regulation of the flow of the breath sample in the flow path may take a number of forms, including regulation of flow rate, flow velocity, the flow regime (laminar, turbulent, etc.), and/or the like. The flow regulation device may be configured to condition the sample of breath such that the sample is at the constant flow rate. But, it may also ensure that the sample of breath is at a pre-determined flow rate, which may vary with time. For example, certain chemical systems have an amplification process, whereby the sensitivity of the sensor increases with increased exposure to an analyte. For such a system, the flow regulation device may allow for increased mass transfer of the analyte during the initial phase of the chemical reaction and then gradually decrease mass transfer of the analyte as the chemical amplification process occurs. Flow regulation may comprise one or more flow diffusers to diffuse or mix the flow.

The conditioning device also may be or comprise a device for adjusting or controlling the temperature of the breath sample at various locations within the flow path. This may comprise, e.g., a heater, a cooler, or some combination of these. Temperature control or adjustment also may be achieved by controlling flow characteristics, e.g., by using a narrow orifice to rapidly increase flow velocity while reducing flow rate and pressure, such as in an evaporator.

The conditioning device may be disposable. In certain embodiments, it may be desirable to package the conditioning device in a sterile package. Accordingly, the measurement device may comprise an access that permits the conditioning device to be inserted, removed, and either replaced or replenished.

Conditioning devices that may be suitable for use are disclosed in the present assignee's U.S. Pub. No. 2014/0276100, the entirety of which is hereby incorporated by reference as if fully set forth herein.

In system 10, measurement device 12 may include a conditioning device in the form of a humidity extraction device or desiccant 42. The humidity extraction device 42 may include a substantially cylindrical container in fluid communication with, for example disposed within, flow path 26, adjacent to, in series with and immediately downstream with respect to mouthpiece 34. The container can be filled with a desiccant material which may consist of or comprise calcium dichloride ($CaCl2$), magnesium perchlorate ($Mg(ClO4)2$), magnesium carbonate ($MgCO3$), lithium chloride ($LiCl$), potassium carbonate ($K2CO3$), copper (II) sulfate ($CuSO4$), calcium sulfate ($CaSO4$), oxobarium ($BaO$), phosphorous pentoxide ($P_2O_5$), zeolite, silica gel, aluminum oxide ($Al_2O_3$), or molecular sieve. In conditioning device 42, the desiccant material comprises, and may consist essentially of, calcium dichloride with a particle size range of −12+18 mesh. The perimeter of each of the proximal and distal ends of desiccant 42 can be covered with a seal (44 and 46, respectively), such as an elastomeric material such as rubber or a resilient plastic, to prevent the passage of the breath sample in the annular space between the outer cylindrical surface of desiccant 42 and the corresponding interior of housing 22 that contains desiccant 42. Because mouthpiece 34 can be detachable, as further described herein below, conditioning device 42 can be removed and replaced or replenished.

Figures 2, 3:
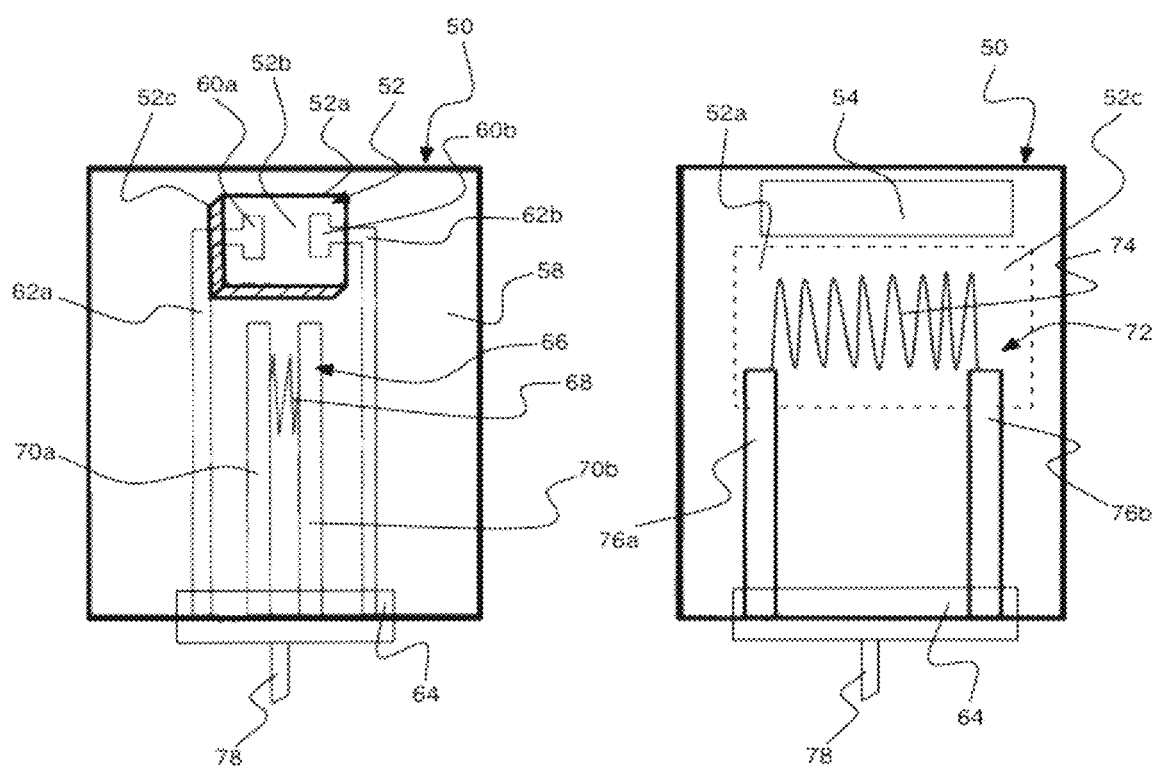
FIG. 2 is a plan top view of a nanoparticle-based sensor subsystem within the measurement device shown in FIG. 1.
FIG. 3 is a bottom view of the nanoparticle-based sensor subsystem of FIG. 2.

Measurement device 12 may include a nanoparticle-based sensor subsystem 50 comprising a sensor 52 disposed in housing 20 and in fluid communication with, for example within, flow path 26 (see FIG. 2). Sensor 52 can be disposed at an intermediate location between upstream end 28 and downstream end 30 of flow path 26, just downstream of desiccant 42.

Nanoparticle-based sensors are comprised of a nanomaterial coupled to an electrode. The term "nanomaterial" is used herein broadly according to its common meaning in the field, to include an analyte-responsive material or element that has been synthesized so that the majority of individual particles or fundamental units of the material or element have characteristic dimensions (e.g., spherical diameter for spheres, cross-sectional diameter for nanotubes, etc.) within the range of a few nanometers to several tens of nanometers, and have been deposited onto a substrate (e.g., as thick-films, self-assembled lawns, etc.). The term "nanomaterial" as used herein also may include substances whose individual particle dimensions are outside of the "nano" specification noted above, but which nevertheless are formulated into a paste, film, or other sensitive layer and adhered to a substrate in contact with electrodes. Examples of nanomaterials that may be used include pure substances (iron III) oxide ($Fe_2O_3$), tungsten (VI) oxide ($WO_3$), titanium (IV) oxide ($TiO_2$), molybdenum (VI) oxide ($MoO_3$), vanadium (V) oxide ($V_2O_5$), chromium (III) oxide ($Cr_2O_3$), indium (III) oxide ($In_2O_3$), tin (IV) oxide ($SnO_2$), manganese (IV) oxide ($MnO_2$)), pure substances of specific crystalline structure (monoclinic, orthorhombic, cubic, etc.), pure substances of specific solid phase (alpha, beta, gamma, epsilon, etc.), pure substances with dopants (gamma $Fe_2O_3$ doped with $TiO_2$, for example), and substances made with specific synthesis methods (sol gel, co-precipitation, ultrasonically assisted co-precipitation, flame spray pyrolysis, etc.), and substances formed with specific nanocrystalline structures (nanoparticles, single-walled nanotubes, multi-walled nanotubes, single crystal nanowires, nanospheres, nanorods, nanofilms, nanoclusters, etc.).

Nanoparticle-based sensors typically comprise a nanomaterial in contact with an electrode material deposited onto a substrate. The nanomaterial may be disposed on the electrode through different means including, without limitation, heat treatment of nanoparticle pastes, drops or powders; low-pressure or vacuum evaporation of pastes, suspensions, or drops; nanoparticle suspensions, self-assembly using gaseous or liquid precursors, etc. The nanoparticle-based sensor may be disposable or it may be reused, depending on the application.

The substrate may be any material that exhibits sufficient adhesion to the nanomaterials and electrode materials of interest, as well as any other physical parameter of interest such as stability under the temperature regime required for sensor operation or mechanical rigidity, and which is otherwise suitable for the application, e.g., by being substantially free of any electrical or magnetic properties that would interfere with the desired operation of the sensor, that do not degas or sublimate interferents, etc. Suitable substrates may include ceramics such as alumina ($Al_2O_3$), glass, or thermally-stable plastics such as polyimide. Nanoparticle pastes can be applied onto substrates with suitable temperature resistance and mechanical rigidity.

An enlarged top or plan view of sensor subsystem 50 is shown in FIG. 2, and an enlarged bottom view is shown in FIG. 3. Sensor subsystem 50 comprises a sensor 52 which in turn comprises a sensor pad 52a which in turn comprises a nanomaterial 52b disposed on a substrate 52c. In system 10 and more specifically in measurement device 12, nanoparticle-based sensor 52 comprises a tin oxide semiconductor sensor formed on an alumina substrate, for example, such as a TGS 822 sensor, commercially available from Figaro USA, Inc. of Arlington Heights, Ill. Alternatively, the sensor may utilize γ-ferric oxide, antimony salt and platinum, such as that disclosed in PCT application IN13/000120 entitled: "A Sensor Composition for Acetone Detection in Breath," which is hereby incorporated by reference in its entirety herein.

Sensor pad 52a is disposed on a printed circuit board ("PCB") 58. A pair of electrode contacts 60a and 60b are disposed on and in ohmic contact with respective ends of sensor pad 52 and, more specifically, with nanoparticle material 54. A corresponding pair of electrical leads 62a and 62b extend from contacts 60a and 60b across sensor PCB 58 and to an edge connector 64.

Operating temperature ranges for nanoparticle-based sensors are commonly in the 100-500° C. range, but can be outside of this range in more rare circumstances. Many operate most optimally in the range of about 300° C. to 400° C. Accordingly, it may be necessary to provide a heating device to raise the sensor to the required temperature during measurement. Thus, sensor subsystem 50 may include a heating device 66 that in turn comprises a resistive coil or element 68 disposed adjacent to nanoparticle material 52b on sensor pad 52a and a pair of electrodes 70a and 70b coupled to resistive element 68. Electrodes 70a and b also are coupled to edge connector 64.

As an alternative to or in addition to heating device 66, which is disposed on the top side of PCB 58, a heating device 72 may be disposed on the bottom side of PCB 58, proximate to and/or under sensor pad 52a (see FIG. 3). In measurement device 12, both are provided. As with heating device 66, heating device 72 comprises a resistive coil or element 74 disposed adjacent to or under sensor pad 52a and a pair of electrodes 76a and 76b coupled to resistive element 74. Electrodes 76a and b also are coupled to edge connector 64.

The electrode contacts 60a,b and electrodes 62a,b, 70a,b and 76a,b can be screen printed onto the substrate 52c and surface material of PCB 58, respectively. A nanomaterial paste can then be applied over substrate 52c and cured at high temperatures. A resistance temperature detector trace also can be screen printed onto substrate 52c, allowing closed loop control of the sensing element's temperature under varying conditions.

The electrode contacts and electrodes may comprise gold, platinum, nickel, silver, copper, and/or other sufficiently conductive and stable material that performs the function of establishing an electrical coupling between the sensitive area of the nanoparticle sensing material and the electrical readout circuitry. They may have a smooth surface or, for certain applications, it may be designed to have a rough surface. As regards the electrode contacts 60a,b, such roughness could allow for increased surface area of the nanoparticle sensing material. The electrode leads at edge connector 64 are spaced so that a single 6-position compression conductor makes contact to both the top and bottom sides simultaneously.

Resistive heating elements 68 and 74 can be deposited onto the respective electrodes near the sensor element (such as resistive pastes or depositions, screen printed onto the substrate) or placed in its proximity (such as resistive wire wound around the substrate or otherwise placed in proximity to the sensing element). Resistive heating elements 68 and 74 can be comprised of any number of materials that exhibit sufficient resistivity, stability, and adhesion to the substrate or positioning scheme, and which exhibit sufficient resistivity, stability, and adhesion appropriate to the operating conditions of the device. Suitable materials may include iron-chrome-aluminum "Kanthal," nickel, gold-palladium, thick-film epoxy-graphite, and others. The heater or heaters can be run open-loop, whereby a constant or pre-defined variable voltage is applied over the heater element, causing current flow which produces heat.

A nanoparticle based sensor subsystem may include a temperature sensor 54 and temperature control element located close to the nanoparticle sensor 52 and may comprise resistive heating wires or traces, resistance temperature devices, thermocouples, control circuitry, and/or other thermal control devices.

The nanomaterial 52b coupled to the electrode 62 may comprise a closed-loop temperature control scheme using a resistance temperature device ("RTD"), thermocouple, or other heat-sensing device working in conjunction with a heater element. Commonly-used RTD materials include platinum and nickel but can include any material that exhibits repeatable resistivity changes as a function of temperature, sufficient resistivity change within the temperature range of interest, and suitable adhesion or fixation properties. Thermocouple elements or other temperature sensing devices can also be used to close the control loop and the methods of manufacture and deployment are both varied and well known. In certain embodiments, closing the loop on thermal control creates a nanoparticle-based sensor that operates more repeatably within a tightly confined temperature range.

The sensing subsystem may comprise a nanoparticle-based sensor coupled to another type of sensor, such as a thermoelectric sensor or an electrochemical sensor. A combination-sensing device of this nature may allow for the measurement and/or analysis of more analytes in breath than any single sensing device or even an array of any single type of sensing device. One example may be an electrochemical sensor for analysis of breath acetone coupled to a nanoparticle-based sensor for analysis of breath oxygen. Or, the sensing device may comprise multiple nanoparticle-based sensors.

As shown in FIGS. 1-3, a cable run 78 comprising wires or electrical conductors for each of the electrodes running to edge connector 64 can run from connector 64 to a device printed circuit board 80 disposed at the distal end of housing 20. PCB 80 comprises the processing and gating circuitry to cause heating devices 66 and 72.

Both PCB 80 and nanoparticle-based sensor 50 can be ohmically coupled to electronic device 14 and/or battery pack 18, so that they can receive power for their operations.

In normal operation of system 10, upon being powered up, PCB 80 causes heating devices 66 and 72 to heat nanoparticle-based sensor 50 to its optimal operating temperature, which may be about 400° C. This heating process also removes some of the humidity and possibly other adsorbed gases or materials on sensor 52. Once sensor 52 reaches this temperature, as indicated by temperature sensor 54, an indicator is provided to user, such as a light (not shown) indicating that the device is ready to begin the acetone measurement test. The user then exhales into mouthpiece 34, which causes the exhaled breath sample to enter flow path 26 and flow in it in downstream direction 32. As the sample passes through desiccant 42, moisture in the sample is substantially reduced. As the sample exits desiccant 42 and continues down the flow path, it contacts sensor 52 at the intermediate location, whereupon the acetone in the breath sample interacts with the sensor and the sensor generates a measurement signal that is representative of the concentration of the acetone in the breath sample. This measurement signal is passed via electrodes 62a and b and cable 78 to PCB 80, which then communicates the measurement signal to electronic device 14.

In a modification of this embodiment, USB cable 16 can be replaced with a wireless link between measurement device 12, and more specifically PCB 80, and electronic device 14. After the breath sample passes sensor 52 and proceeds down flow path 26 in downstream direction 32, past a one-way exit valve 82, and it is vented at a series of venting ports 84 at the distal or downstream end of flow path 26. Venting ports 84 are angled with respect to the longitudinal axis of housing 20 and with respect to the plane normal to the longitudinal axis L, as indicated at 86, so that the warmed breath sample is vented away from the user. A grip 88 is disposed on the exterior of housing 20 in the vicinity of the intermediate location so that the user can grip measurement device 12 at a location that is insulated from sensor 50 and is away from the vented breath sample.

With system 10 as thus far described, there is a concern that sensor 52, and the heat associated with it during operation, is in fluid communication with the user's mouth, possibly nasal passages, and respiratory tract via the portion of flow path 26 that is upstream of sensor 52 (chamber 26a) and through mouthpiece 34. Thus, if the user were to inadvertently inhale during the normal use of system 10, discomfort and potentially personal injury could occur. To address such concerns, system 10 may include a flow control subsystem to mitigate or prevent respiratory tract inhalation.

The flow control device or subsystem can be disposed in the housing and in the flow path between the upstream end and the nanoparticle-based sensor at the intermediate location. It prevents flow of the breath sample in an upstream direction opposite the downstream direction.

The flow control device or subsystem of system 10 comprises a one-way valve 90 disposed in flow path 26 at the distal end of mouthpiece 34 and upstream from desiccant 42. Optionally, the flow control subsystem may include a second one-way valve 92 disposed in flow path 26 downstream from conditioning device 42 but upstream from the intermediate location and sensor 52. Both valves 90 and 92 allow the breath sample to flow in the downstream direction 32, but close to prohibit the breath sample from flowing back in the upstream direction. First one-way valve 90 further mitigates the risk of the user inadvertently inhaling the desiccant in conditioning device 42 in the event of a failure of the latter in which desiccant is released.

Figure 4A:
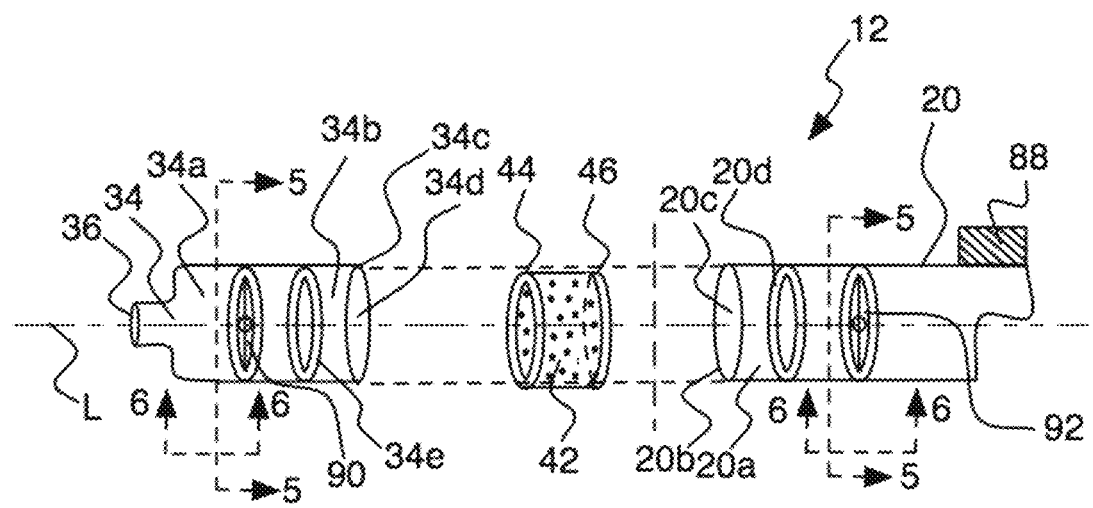
Figure 4B:
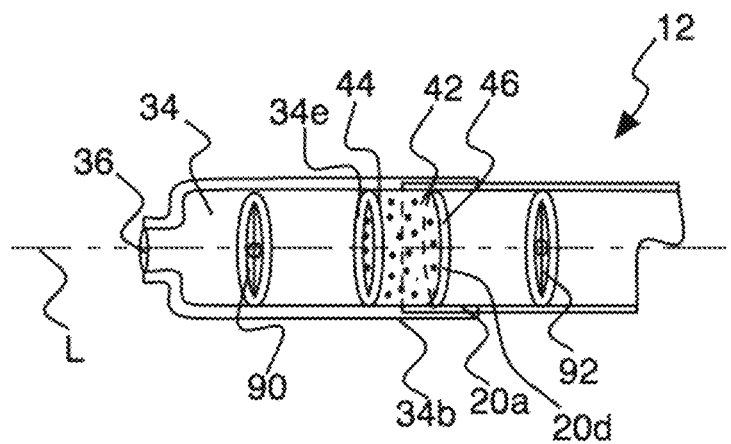

FIGS. 4A and B provide enlarged and partial cutaway side views of the upstream section of housing 20 in which valves 90 and 92 are disposed. FIG. 4A is an exploded view expanded along the longitudinal axis L of housing 20. FIG. 4B shows a corresponding side view, but in which the sections have been moved back together longitudinally to their mated and operational configurations.

FIG. 4A shows mouthpiece 34 longitudinally separated from housing 20 in expanded or exploded form. Conditioning device 42 is shown positioned between mouthpiece 34 and housing 20. One-way valve 90 is disposed in mouthpiece 34 upstream from conditioning device 42. Mouthpiece 34 has a breath input section 34a at its proximal region and a skirt section or skirt 34b at its distal region. The mouth piece 34 can have a distal edge 34c and a distal opening 34d. A stop flange 34e can be fixedly disposed peripherally in the interior of mouthpiece skirt 34b to serve as a stop for conditioning device 42, to secure and immobilize device 42 in the mouthpiece and prevent it from moving upstream past stop flange 34e.

Housing 20 can have an upstream or proximal skirt portion 20a, a proximal edge 20b and a proximal opening 20c. A stop flange 20d can be fixedly disposed peripherally in the interior of proximal skirt 20a to serve as a downstream stop for conditioning device 42, to secure and immobilize device 42 in proximal skirt 20a of housing 20 and prevent it from moving downstream past stop flange 20d.

Figure 5:
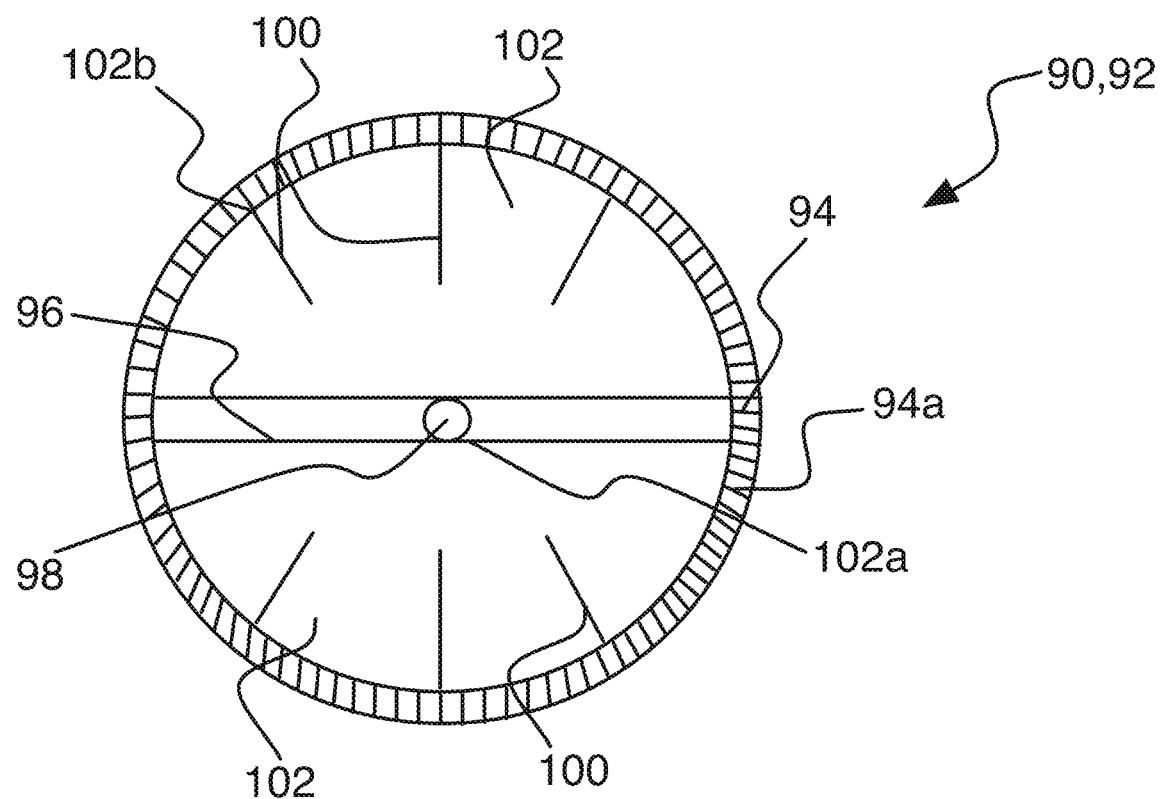
FIG. 5 is a longitudinal or end view of the interior of measurement device of FIG. 1 taken in cross section along the lines 5-5 in FIG. 4A which illustrates one-way valves disposed in the measurement device.

One-way valves 90 and 92 differ in their location within measurement device, but the valves themselves have identical construction. FIG. 5 shows a longitudinal cutaway view of each valve as indicated by line 5-5 in FIG. 4A. Each valve 90,92 can include a peripheral flange 94 that can be fixedly disposed peripherally in the interior of the flow path 26, which for valve 90 is the interior of mouthpiece skirt 34b and for valve 92 is the interior of proximal skirt 20a. Peripheral flange 94 can be spaced from the corresponding stop flange 20d and 34e so that a small air gap is provided between conditioning device 42 and the corresponding peripheral flange. Peripheral flange 94 can include a shelf 94a that extends into flow path 26 perpendicularly with respect to the longitudinal axis L. A support beam 96 can extend at least partially laterally across peripheral flange 94. A post 98 can extend longitudinally from the center of support beam 96 at the center of peripheral flange 94 and at the longitudinal axis L. One or more support members 100 can extend from peripheral flange 94 inward radially so that they are coplanar with respect to shelf 94a. A substantially circular semi-rigid valve closure 102 can be disposed on the substantially planar support structure formed peripheral flange 94 (and more specifically shelf 94a), support beam 96 and support members 100. Valve closure 102 has a hole 102a at its center to receive post 98, so that valve closure lies at the base of post 98 and against the support structure. The relative sizing of hole 102a and post 98, together with appropriate beveling or tapering of post 98, secure it in this position with a press-fit-type lock. The diameter of valve closure 102 is substantially the same as but slightly less that the interior diameter of flow path 26, and is greater than the diameter of the interior periphery of support shelf 94a. Thus, valve closure 102 at rest conforms to the plane of the support structure and rests at its periphery 102b on shelf 94a and thereby closes flow path 26 at that point or location.

Valve closure 102 may comprise any one of a range of materials that is sufficiently rigid to prevent backflows of air, but yet sufficiently resilient to permit air flows in operation as further described herein below. Valve closure also should have sufficient thermal stability to retain its semi-rigidity under thermal conditions encountered operationally. It also should have appropriate biocompatibility for the circumstances of its intended use. In some embodiments, valve closure 102 is a thin polyethylene sheet.

Figure 6A:
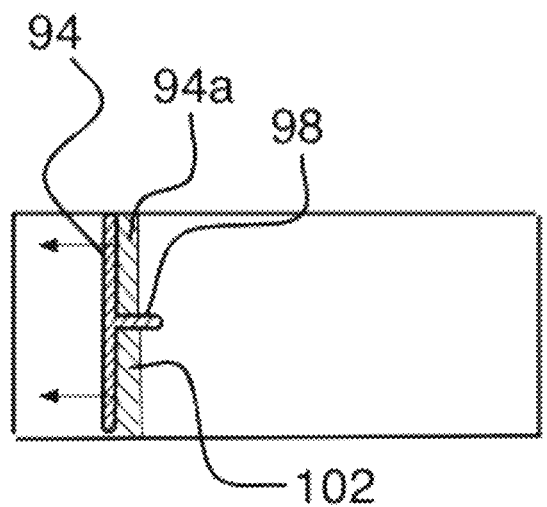
Figure 6B:
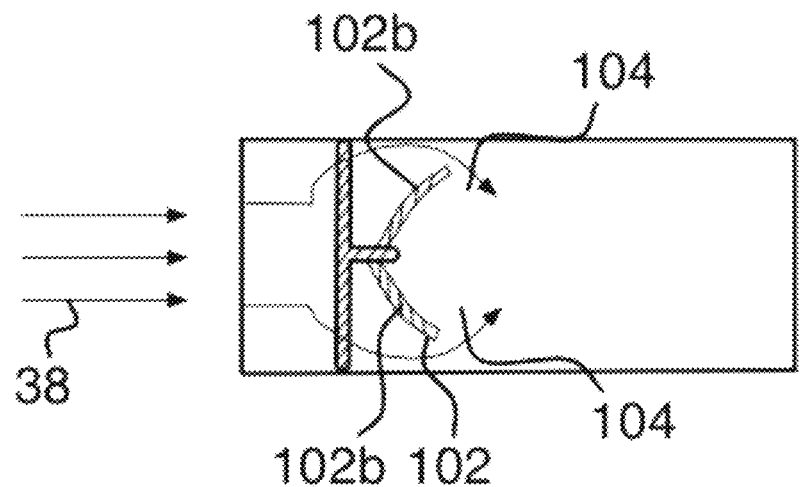

The operation of the valve (90,92) is illustrated in FIGS. 6A and 6B, wherein FIG. 6A shows a side cutaway view of the valve in a closed state, and FIG. 6B shows a side cutaway view of the valve in an open state. In FIG. 6A, the valve is at rest, e.g., in storage or prior to use. Valve closure 102 conforms to the plane of the support structure and rests at its periphery 102b on shelf 94a so that flow path 26 is closed at that point or location. When the user exhales into mouthpiece 34 (or, with respect to other embodiments as described herein below, the breath sample is otherwise inputted into the flow path), as shown by arrows 38, the breath sample flows in the downstream direction 32. The pressure from this inputted fluid sample is applied to valve closure 102, which at its attachment point at post 98 has no effect with regard to motion. At its peripheral edge 102b, however, which is unattached to the support structure or, more specifically, to shelf 94a, and is free to move in downstream direction 32, peripheral edge 102b moves away from shelf 94a, thereby creating a flow passage channel around valve closure 102 and thus opening flow path 26 to allow this downstream flow (see FIG. 6B).

If the user happens to inhale during operation of the device 12 and, most disconcertingly, when sensor 50 is at its elevated operating temperature or higher, this upstream flow would quickly create a low pressure condition at the upstream side of valve closure 102, thereby causing a force 106 in the upstream direction that would close valve closure 102 and prevent further upstream flow (see FIG. 6A). Ideally, this volume of fluid that is allowed to backflow in the upstream direction prior to and as part of closing valve closure would include only a small volume of fluid that is sufficiently small, close to valve closure 102 and far from sensor 50, that no more than minimal and safe heat transfer takes place. This can be accommodated through such specific design features in a given application as the sizes of the flow path and valve closure, the spacing from the sensor to the valve closure, and the speed of valve closure.

In system 10 as described and illustrated herein, because measurement device 12 may include not only valve 90 at mouthpiece 34 but also valve 92 downstream of conditioning device 42, such unintentional upstream or backflow would close both valves 90 and 92 substantially simultaneously. As a result, the relatively minimal portion of the fluid from the portion of the flow path in which the sensor resides that moves past valve 92 and into conditioning device 42 as valve 92 is closed would be insufficient to travel upstream through conditioning device 42 and through valve 90 and into the mouthpiece before valve 90 is closed. The sizing of conditioning device along longitudinal axis L the spacing between valves 90 and 92, or both, could be used to guarantee this result.

Figure 7:
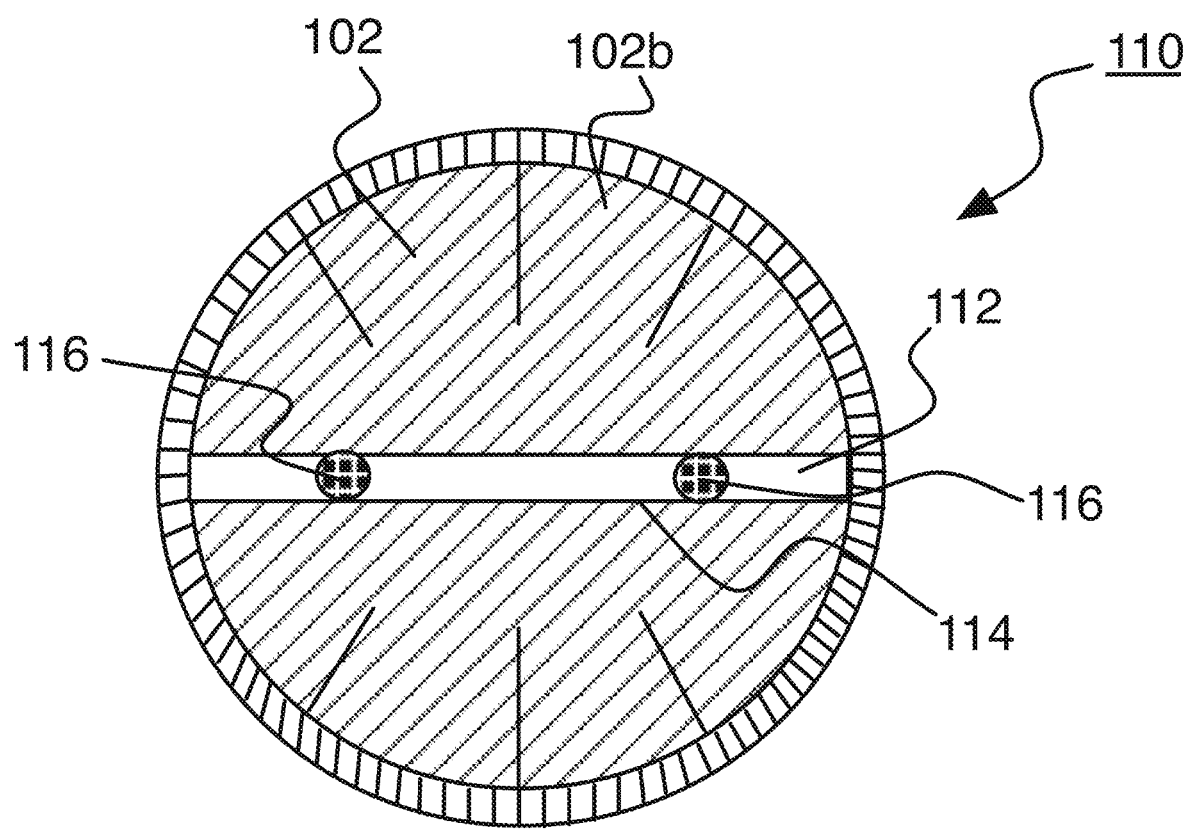
FIG. 7 is a longitudinal or end view of the interior of measurement device of FIG. 1 taken in cross section along the lines 5-5 in FIG. 4A which illustrates an alternative embodiment of one-way valves disposed in the measurement device.
Figure 8:
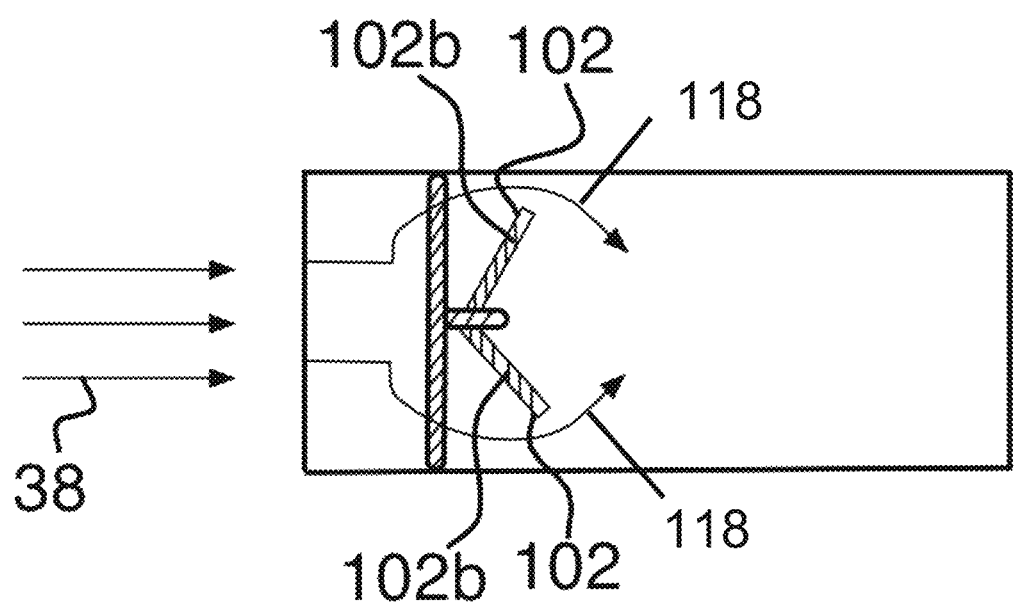
FIG. 8 is a side cutaway view of a portion or portions of the measurement device of FIG. 1, that illustrates the operation of the one-way valve of FIG. 7 within the portion.

Alternative designs for the one-way valves 90,92 may be used. As an example, a "butterfly" valve 110 is shown in FIG. 7, which more specifically shows a longitudinal end view of valve 110 looking down flow path 26 assuming a pair of valves 110 is substituted for valve pair 90 and 92. The support structure for valve 110 is the same as for valves 90 and 92, more specifically including peripheral flange 94, shelf 94a, support beam 96 and support members 100. Valve 110 does not include post 98 from valves 90 and 92, but instead comprises a hinge 112 at the top of support beam 96 that is formed by a top bar 114 and a pair of press-on posts 116. Valve 110 includes a valve closure that is identical to valve closure 102, but which includes two holes for press-on posts 116 rather than center hole 102a. When at rest, valve closure rests against shelf 94a as shown in FIG. 6A. The rigidity of valve closure 102 provides a mild bias of peripheral edge 102b so that flow path 26 is closed at the location of the valve. When a breath sample is introduced via mouthpiece 34, as shown at 38, the hinged valve closure 102 opens with respect to the hinge so that the breath sample is allowed to pass around peripheral edges 102b and through the apertures 118 thereby created (see FIG. 8).

Figure 9A:
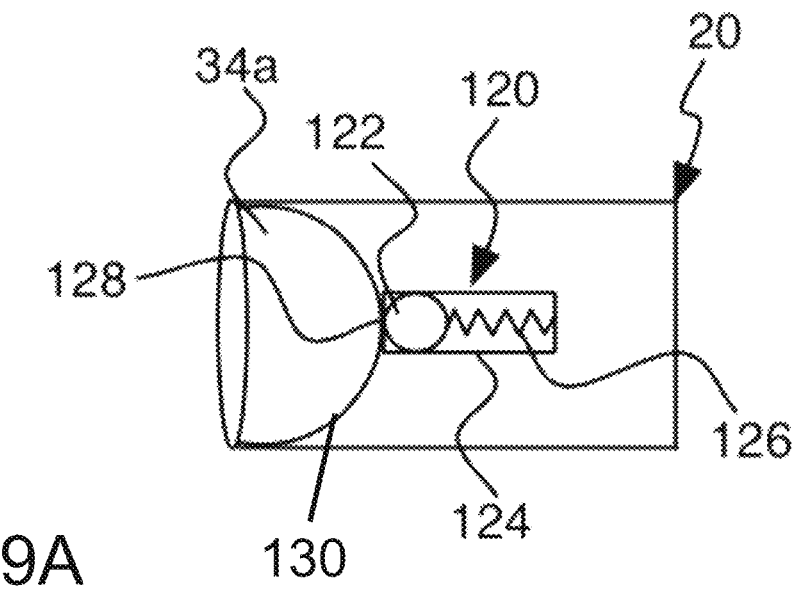
Figure 9B:
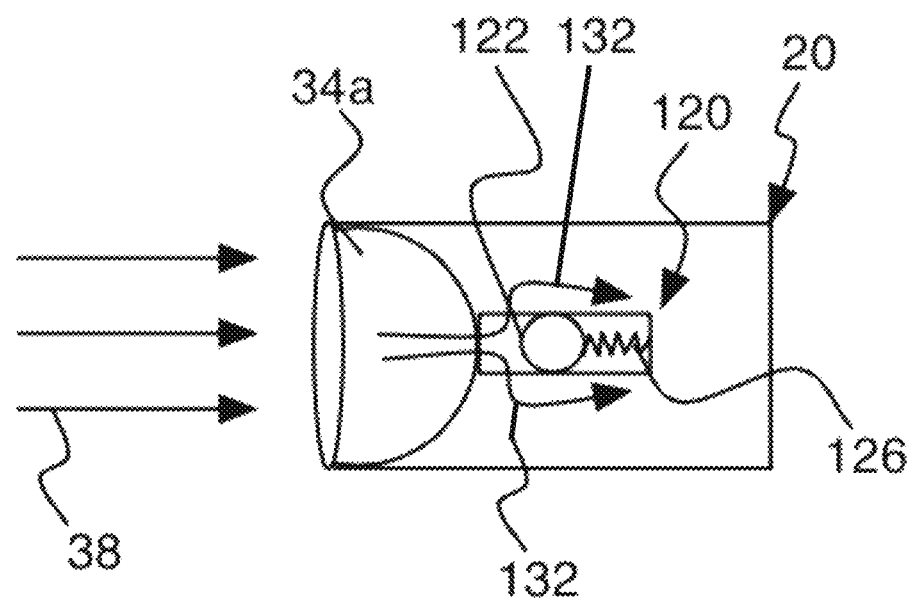

Another alternative design for the one-way valves 90,92, this one a "ball valve" valve 120 is shown in FIGS. 9A and 9B. FIGS. 9A and 9B show a side cutaway view of the locations in flow path 26 that include valves 90 and 92, but wherein ball valve 120 is substituted for valve 90 and, separately, valve 92. FIG. 9A shows valve 120 in a closed state, and FIG. 9B shows the valve 120 in an open state. Valve 120 comprises a ball 122 disposed in a cylindrical ball housing 124 that includes a biasing device 126 such as a biasing spring that biases ball 122 into a hole 128 in a concave wall 130 of mouthpiece breath input portion 34a. Hole 128 is smaller than the diameter of ball 122, so that ball 128 when thus biased blocks hole 128 and closes flow path 26.

When a breath sample is inputted into mouthpiece 34 as indicated at 38, the pressure created in breath input portion 34a pushes ball 122 longitudinally downstream against biasing spring 126 in housing 124, thus opening hole 128 so that the breath sample can flow through valve 120, as shown at 132. When the input of breath sample ceases, the pressure in mouthpiece input portion 34a drops, and biasing spring 126 forces ball 122 upstream in housing 124 to re-close hole 128.

Returning to measurement device 12 as shown in FIG. 4, mouthpiece 34 can be detachable from housing 20. In other configurations, the mouthpiece may be fixedly attached to the housing 20. These components are shown in separate, exploded or expanded view in FIG. 4A, but they may be assembled into normal form for use as illustrated by the transition from FIG. 4A to FIG. 4B, as will now be described.

A user may be provided with at least two components (e.g., two, three, more). One is mouthpiece 34, with valve 90 permanently or removably affixed in it. Optionally, conditioning unit 42 may come predisposed in mouthpiece 34, which would be inserted into mouthpiece distal opening 34d so that rubber seal 44 contacts and abuts stop flange 34e. Alternatively, the conditioning device 42 my come predisposed in housing 20, or as a separate (third) component in addition to mouthpiece 34 and housing 20. In the continuing description, it will be assumed that conditioning device comes as a pre-disposed and pre-assembled component of mouthpiece 34. Incidentally, given the personal nature of mouthpiece 34 with respect to a given user and the fact that mouthpiece 34 and conditioning device 42 will become soiled or contaminated with breath components with use, these two components generally will be replaceable or consumable and disposable components of the overall device 12.

Housing 20 can come with one-way valve 92 pre-disposed in its interior as depicted in the drawing figures. The outer diameter of housing proximal skirt 20a is slightly smaller than the inner diameter of mouthpiece skirt 34b, and they are sized relative to one another so that housing proximal skirt 20a can be slid into and surrounded by mouthpiece skirt 34b in substantially air-tight, slip-fit arrangement (or press-fit, snap fit, threaded, or any other air-tight arrangement). Alternatively, the housing proximal skirt 20a can be slide over the mouthpiece skirt 34b in the substantially air-tight arrangement. As mouthpiece 34 is slid over housing proximal skirt 20a, the distal or downstream end of conditioning device 42 is slid into housing proximal opening 20c until reaches its final position in the housing, e.g., when rubber seal 46 contacts and abuts stop flange 20d. As this occurs, mouthpiece 34 is in substantially airtight, mating contact with housing 20 at the latter's proximal end, so that device 12 is as depicted in FIG. 1, and conditioning device 42 is fixed and immobilized, for example between stop flanges 20d and 34e. Rubber seals 44 and 46 in abutting arrangement with those flanges can create a substantially airtight section of flow path 26.

The operation of system 10, fully configured as has been described and illustrated herein, is as follows. With reference to FIG. 1, measurement device 12 can be coupled to electronic device 14 via cable 16 and the device is powered on. An indicator may indicate when the heating devices have raised the temperature of sensor 52 to its optimal operating temperature, for example, a light on the housing can be illuminated. This can indicate to the user that the device is ready for the acetone test. Upon receiving this indication, the user places his or her mouth on mouthpiece 34 and exhales to input a breath sample into device 12 through the mouthpiece, as indicated at 38, and in downstream direction 32. This downstream flow causes one or more one-way valves 90 and 92 to open so that the breath sample optionally flows through conditioning device 42, where the humidity in the sample is reduced, and into chamber 26a where sensor 52 is located. The dehydrated or otherwise conditioned breath sample contacts sensor 52, which is still at its optimal operating temperature, whereupon sensor 52 interacts with or measures the breath sample and generates a measurement signal. That measurement signal can be communicated via cables 78 to device PCB 80, which then communicates the signal to electronic device 14.

If during the exhalation or otherwise during the operation of device 12 the user inhales or otherwise causes a back pressure or back flow at mouthpiece, the one or more one-way valves 90 and 92 promptly will be closed, thus preventing any gas or heat from sensor 52, or chamber 26a, from reaching mouthpiece breath input section 34a, and thereby preventing such gas or heat from reaching the mouth or respiratory tract of the user.

System with Breath Bag

Figure 10:
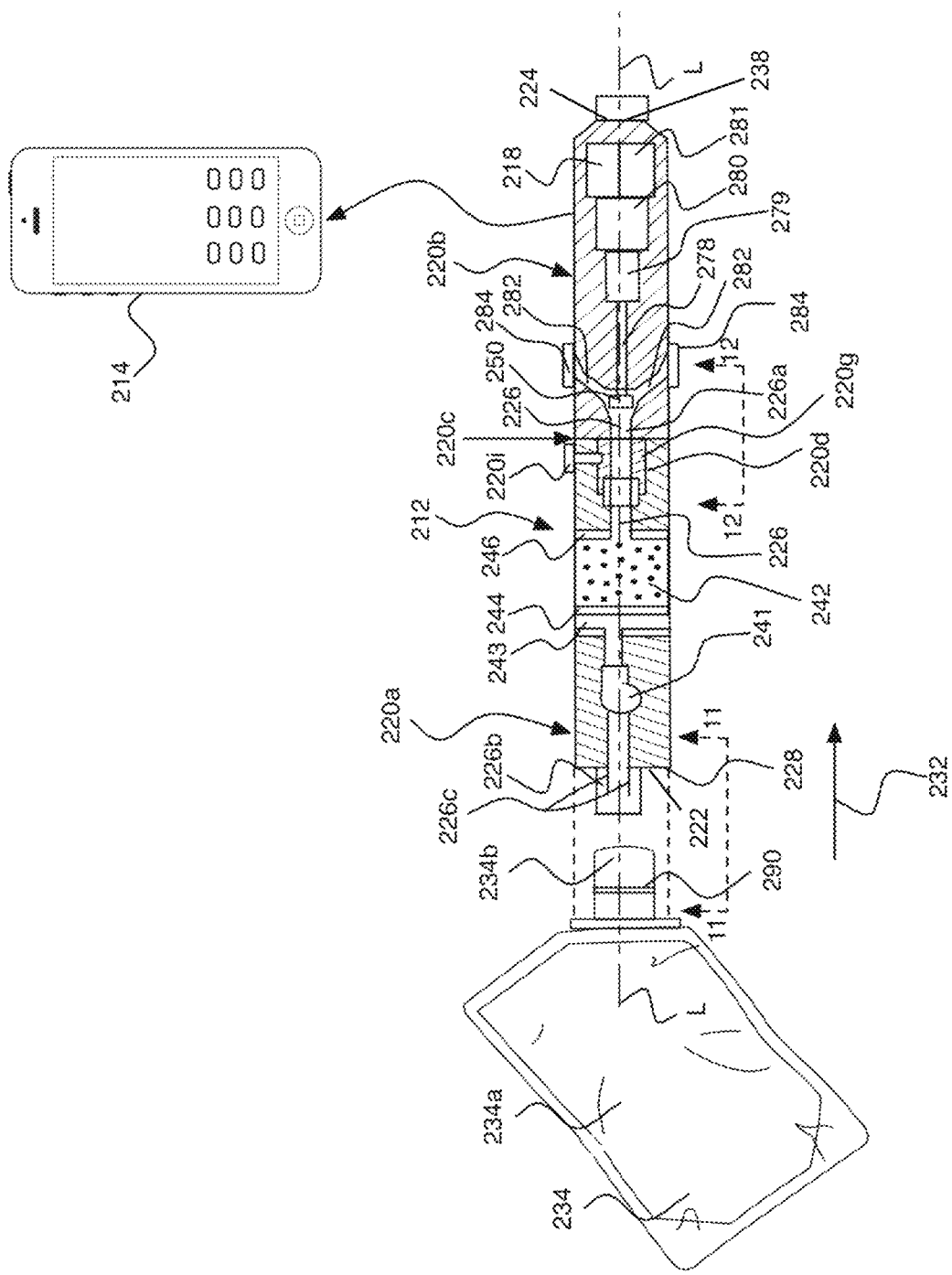
FIG. 10 is a pictorial view of another breath acetone measurement system according to one embodiment, including a side cutaway view of a measurement device that is part of the system, in which the system comprises a breath bag for collection and delivery of the breath sample.
Figure 11A:
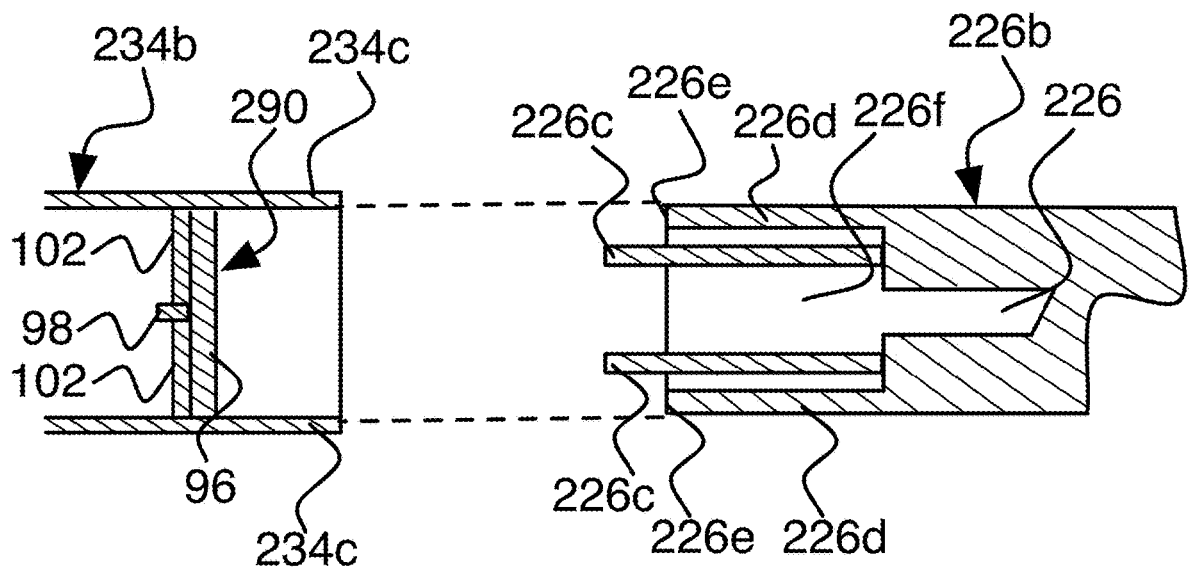
Figure 11B:
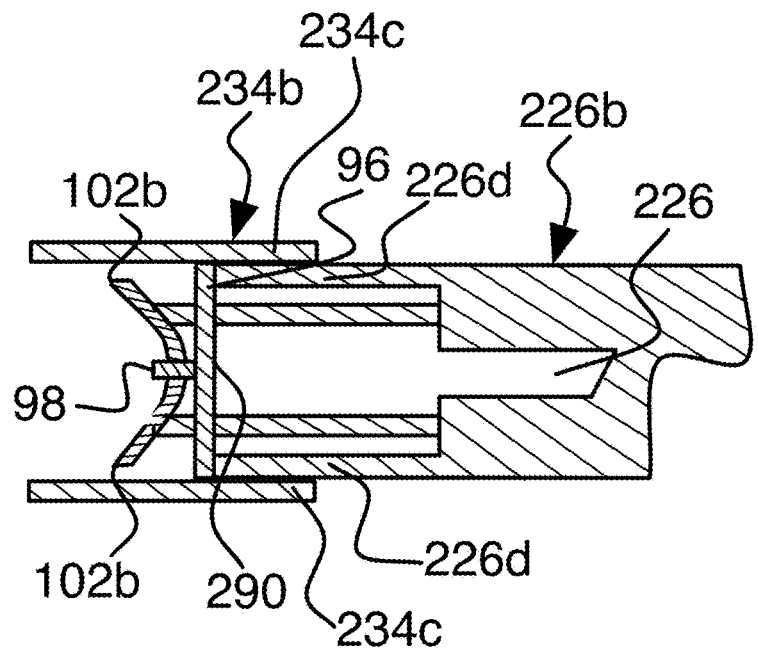
Figure 12:
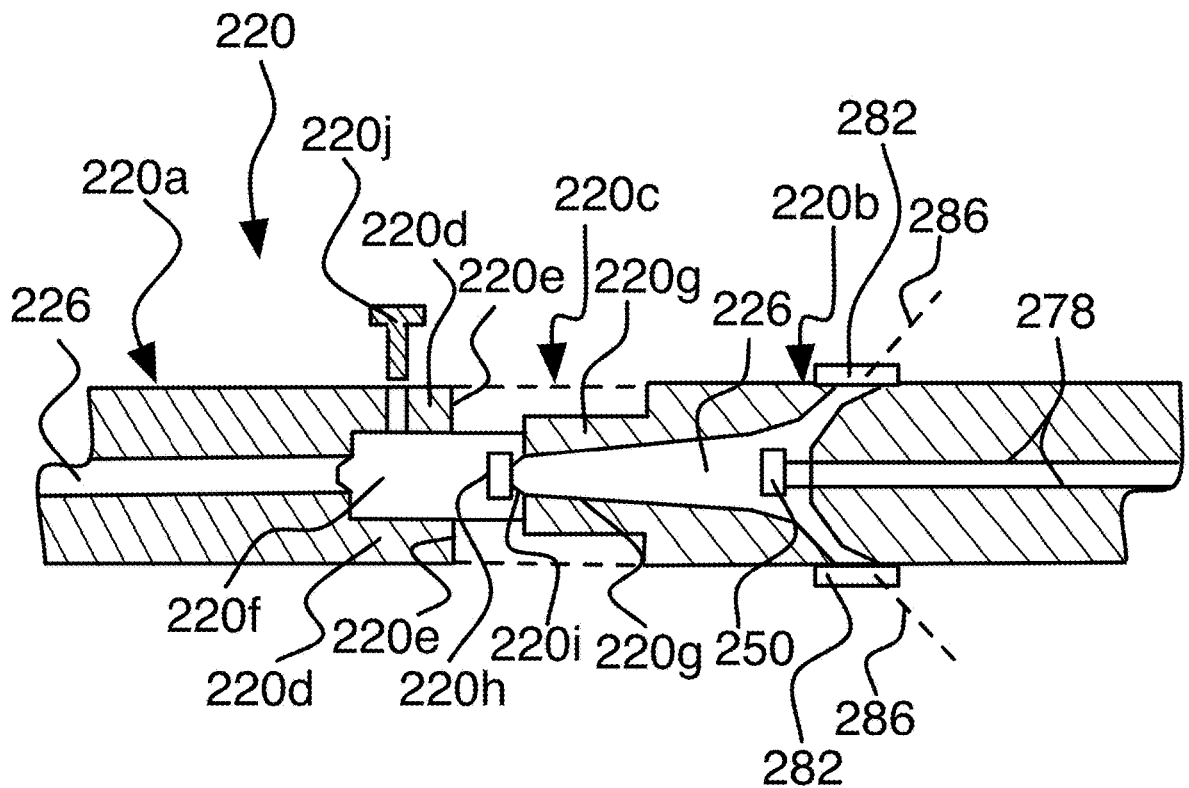
FIG. 12 shows side cutaway views of a portion of the measurement device of FIG. 10 at a joinder between proximal and distal sections of the measurement device.

In accordance with another aspect of the present disclosure, FIGS. 10-12 illustrate a system 210 for measuring acetone in a breath sample of a user and appropriately reporting or storing the measured result or results. System 210 is very similar to system 10, including many of the same components. Accordingly, numerals used to identify features of the system 210 are incremented by a factor of two hundred (200) to identify like features of the system 10.

System 210 comprises a portable, hand-held breath measurement device 212 and an electronic or communications device 214, the latter of which here is illustrated as a cellular telephone in the form of a so-called "smart phone," such as an Apple iPhone®. Measurement device 212 is wirelessly coupled to electronic device 214 in this embodiment, for example, via a WiFi or Bluetooth module 281 that allows measurement results data to be transferred from measurement device 212 to electronic device 214. Electrical power can be provided within measurement device 212 a battery pack 218 as described herein above with respect to system 10.

Measurement device 212 comprises a housing 220 that, in this embodiment as in system 10, comprises a tubular or substantially cylindrical body. To better illustrate measurement device 212, as in device 12, housing 220 is disposed about a longitudinal axis L that corresponds to the axis of the cylindrical body. Housing 220 can be constructed of materials as described herein above. Housing 220 also has an upstream end 222 and a downstream end 224.

Housing 220 further comprises a flow path 226 disposed within housing 220 substantially along longitudinal axis L. At least a part of flow path 226 comprises tubing, although sections of it may not, as further described herein below. Flow path 226 comprises an upstream end 228 corresponding to housing upstream end 222 and a downstream end 238 corresponding to housing downstream end 224. The direction of flow from upstream end 228 to downstream end 230 is referred to herein as the downstream direction 232. The direction directly opposite to the downstream direction, i.e., from the downstream end 230 to the upstream end 228 is referred to herein as the upstream direction.

An input coupler 226b (sometimes referred to herein as a conduit) can be provided at upstream end 228 of flow path 226. The input coupler 226b may be substantially cylindrical. At least one post 226c can be disposed (e.g., fixedly disposed) within the interior of input coupler 226a.

System 210 can also include a breath input device to facilitate the input of the breath sample into the flow channel. In system 210, an "indirect" breath input device can be used, as well as devices that involve indirect input of the breath sample, such as a sealed breath sample storage container or unit, e.g., a tank, bottle, syringe, breath sample collection bag, or combinations of these, and the like. In indirect input designs, the breath sample storage unit may be fluidically coupled to the flow path using a conduit such as a pipe, tubing, and the like.

In system 210, the breath input device comprises a breath bag 234. Breath bag 234 is used by the system user separately from measurement device 212 to collect and retain a breath sample. Breath bag 234 then can be coupled to measurement device 212 to provide the breath sample to flow path 226 for analysis. In some configurations, once the measurement is made, breath bag 234 can be detached from measurement device 212 and re-used or discarded.

Breath bag 234 comprises a bag portion 234a, a mouthpiece, and a connector, such as ferrule 234b. Breath bag portion 234a contains and retains the breath sample inputted by the user. The wall materials of breath bag 234 are substantially air tight, substantially impermeable to acetone. The wall materials of the breath bag 234 may be substantially impermeable to both ambient air components outside the bag and chemical interferents within the collected sample. The walls of the breath bag may be any of a variety of materials that is sufficiently impermeable to air or breath and the analyte of interest, which here is acetone. The wall material also should be substantially impermeable to unwanted constituents of the air or gas outside the bag from infiltrating into the breath sample. Optionally, the material may be relatively light weight for ease of portability and use, and have sufficient flexibility or resiliency to collapse or fold neatly for storage. Examples of such materials comprise low density polyethylene, linear low density polyethylene, polyester films such biaxially-oriented polyethylene terephthalate, and such related commercially-available materials, such as Mylar, Tedlar, Melinex and Hostaphan. In some embodiments, the bag portion material is a low density polyethylene.

Mouthpiece and ferrule 234b serves several functions. Initially it can serve as a mouthpiece for collection of the breath sample from the user, although the bag 234 may have a mouthpiece separate from the ferrule 234b. In that regard, the ferrule 234b may include a one-way valve 290 (e.g., identical to one-way valve 90 of measurement device 12 as described herein above and as shown in FIGS. 5 and 6), but wherein the valve can oriented so that the breath sample is permitted to enter bag 234 but not to exit the bag, except in conjunction with measurement device 212 as described herein below. Ferrule 234b can retain or store the breath sample from the time it is collected and until it is used for acetone measurement, as described herein below.

Breath bag 234 couples to measurement device input coupler 226b. In some configurations, the breath bag 234 may also be detachable for reuse or replacement. The manner of this coupling is shown in greater detail in FIGS. 11A and 11B. FIG. 11A shows the breath bag ferrule 234b and measurement device input coupler 226a in separate but juxtaposed position just prior to coupling. Valve closure 102b is in its closed state, and thus coplanar with and supported by the support structure comprising peripheral flange shelf 94a, support beam 98 and support members 100, (see FIGS. 5 and 6A). This configuration secures the breath sample within bag 234.

Ferrule 234b at its distal end (away from breath bag portion 234a and toward measurement device 212) comprises a ferrule skirt 234c that extends distally with respect to valve 290. Measurement device input coupler 226a similarly has a coupler skirt 226d that extends outwardly (away from flow path 226 and toward breath bag 234). In the process of coupling breath bag 234 to measurement device 212 at input coupler 226b, one slides ferrule 234b, and more specifically ferrule skirt 234c, longitudinally over or within coupler skirt 226d. As shown in FIG. 11B, when engaged, the peripheral edge 226e of coupler skirt 226d can contact and abut the support structure of ferrule valve 290 (peripheral flange 94, support beam 96, and/or support members 100, see FIGS. 5 and 6A. The exterior of coupler skirt 226d is sized to be substantially the same diameter as but slightly smaller than the interior diameter of ferrule skirt 234c or slightly larger than the outer diameter of ferrule skirt 234c, so that the two slidingly engage to form a substantially air-tight seal between the interior of bag portion 234a and measurement device flow path 226.

As ferrule 234b and input coupler 226b are slidingly engaged, posts 226c extend through the spaces above and below support beam 96 of valve 290 and contact valve closure 102, which moves the top and bottom portions of valve closure 102 away from the support structure to open the valve and allow flow of the breath sample from bag portion 234a into a breath input portion 226e of input coupler 226b and into flow path 226. (See FIG. 6B.)

Alternative designs for the breath collection bag may be used in place of breath bag 234. Examples include the breath bags and associated flow control hardware disclosed in the present assignee's U.S. Pub. No. 2014/0276100, and particularly those of FIGS. 2, 3 and 10, and associated text in that document, which is hereby incorporated in its entirety herein.

Returning to FIG. 10 and with attention directed to the upstream end of flow path 226 at input coupler 226b, a pump 241 can be disposed in the flow path downstream from input coupler 22b. Pump 241 can be configured to pump the breath sample in flow path 226 in the downstream direction 238.

A conditioning device 242 as described herein above with respect to device 42 can be disposed in flow path 226 downstream from pump 241 to receive the output from pump 241. Rubber seals 244 and 246 can be provided at the upstream and downstream ends, respectively, of conditioning device 242 to prevent unwanted annular flow of the breath sample between conditioning device 232 and the interior wall of housing 220. A flow diffuser 243 can be provided at the upstream end of conditioning device 242 to diffuse and disperse the breath sample flow across the face of conditioning device 242, e.g., to avoid channeling within the conditioning device and to improve its efficiency. A flow restrictor, such as a porous metal flow restrictor, can be disposed in the flow path just downstream of pump 241.

Housing 220 in this embodiment comprises two detachable sections, e.g., an upstream housing section 220a and a downstream housing section 220b, which are detachably joined at a joinder 220c. Although, in other configurations, the housing 220 may include a single section or more than two sections. An enlarged and expanded cutaway view of this joinder area is shown in FIG. 12, as indicated by the arrows 12 in FIG. 10. The distal or downstream end of upstream housing section 220a comprises a skirt 220d with a peripheral edge 220e, which form an opening 220f. The proximal or upstream end of downstream housing section 220b, which is configured to slidingly mate with upstream section 220a, comprises a skirt 220g. Skirt 220g is sized to that its exterior diameter is substantially the same as the interior diameter of upstream housing section skirt 220d, and slightly smaller, so that skirt 220g can be slidingly engaged inside skirt 220d to form a substantially air tight seal. A rubber seal 220h, such as a gasket or o-ring, can be disposed on the upstream end 220i of downstream section 220b, surrounding flow path 226, so that, as housing sections 220a and b are slidingly joined, rubber seal 220h contacts, joins and seals the flow path in both sections, thus enabling the breath sample to flow through the joinder without leaking breath out of the flow path and without infiltration of air or gas into the flow path at that point. Housing sections 220a and b can be joined to form an air-tight arrangement (e.g., press-fit, snap-fit, screw-fit, or otherwise). In some configurations, when joined, the housing sections 220a and b can be secured by a screw 220j that extends through upstream housing skirt 220c and into downstream housing skirt 220g.

Measurement device 212 further comprises a nanoparticle-based sensor system 250 comprising a sensor 252 disposed in housing 220 and in fluid communication with, for example within, flow path 226. Sensor 252 can be disposed at an intermediate location between upstream end 228 and downstream end 230 of flow path 226, for example downstream of conditioning device 242 and joinder 220c. Nanoparticle-based sensor subsystem 250 and its associated electrical components are as described herein above with respect to nanoparticle-based sensor subsystem 50 and as illustrated in FIGS. 2-3.

Cables 278 (equivalent to cables 78 in device 10) extend down device 212 and ohmically couple nanoparticle sensor 252 with device printed circuit board 280 (equivalent to PCB 80 of device 10). Both PCB 280 and nanoparticle-based sensor 252 are ohmically coupled to battery pack 218 so that they can receive power for their operations.

The operation or use of system 210 involves two steps. In a first, the user employs breath bag 234 to collect a breath sample and attaches the breath bag to measurement device 212. In a second, measurement device 212 inputs the breath sample from breath bag 234, analyzes it to obtain a measurement result, and outputs that result to electronic device (here iPhone) 214.

In the first step, or breath sample collection step, breath bag 234 is used separately and may be detached from measurement device 212 to collect the breath sample. The user grips the bag by mouthpiece/ferrule 234b, positions at his or her mouth, and exhales through mouthpiece 234b and valve 290 to fill bag portion 234a with the breath sample. As this occurs and thereafter, valve 290 prevents the breath sample from escaping from bag portion 234a and retains it there.

The user then positions breath bag as shown in FIG. 10 so that mouthpiece/ferrule 234b is in alignment with longitudinal axis L and input coupler 226b of measurement device 212, and slides ferrule 234b onto coupler 226b so that the former is abutted to the latter and posts 226c contact and open the valve closure of valve 290. This allows the breath sample in breath bag 234 to flow into the portion of flow path 226 between breath bag 234 and pump 241, and to reach equilibrium pressure within this section. It should be noted that this feature may automatically opening the breath bag and allow the breath sample to enter the flow path without the requirement for the user to manually open a valve on the breath bag provides a number of advantages, e.g., such as ease of use, fewer mechanical parts, less risk of disturbing or compromising the seal, and so on.

The user then powers up measurement device 212, whereupon PCB 281 causes heating devices 66 and 72 (FIGS. 2-3) to heat nanoparticle-based sensor 252 to its optimal operating temperature of about 400° C. Once sensor 252 reaches this operating temperature, PCB 280 causes pump 241 to actuate, which causes the breath sample to flow downstream through pump 241, through conditioning device 242, through joinder 220c and into chamber 226a. As the breath sample enters chamber 226a, it contacts nanoparticle-based sensor 252, whereupon acetone in the breath sample interacts with sensor 252 to generate the measurement signal. The breath sample passes sensor 252 and exits device 212, such as through exit valve 82 and through venting ports 284. The measurement signal generated by sensor 252 is communicated via cables 278 to PCB 280. The measurement signal is then wirelessly communicated via Bluetooth module 281 to electronic device 214.

In view of the foregoing, it is clear that the use of system 210, which includes detachable breath bag 234, prevents the risk that heated, toxic or potentially injurious gases from sensor 252 or chamber 226a will come into contact with the user's mouth, oral cavity or respiratory tract.

As an alternative or additional safety feature, in systems such as systems 10 and 210, the nanoparticle-based sensor can be disposed within the housing and the intermediate location can be selected so that the nanoparticle-based sensor is substantially inaccessible to the user during use of the device or system. As shown in FIGS. 1 and 10, nanoparticle-based sensor 52 and 252, respectively, are disposed within their respective housing, where the user cannot intentionally or inadvertently touch or grip them and sustain a thermal or chemical burn. In system 210, although housing 220 is segmented into an upstream section 220a and a downstream section 220b, they are mated to prevent direct access by the user, and they are secured by screw 220i. Nanoparticle sensor 250 thus is inaccessible to the user during normal use of measurement device 212, even though it can be accessed when not in use with the aid of a tool, in this case a screw driver. This segmented design thus affords the opportunity to service or replace the sensor 252 if and when needed, but safely secures it out of the intended or unintended contact by the user during use.

It should be noted that the use of a controllable pump in fluidic communication with the nanoparticle-based sensor, e.g., as shown in FIG. 10, can allow the user to adjust or control and improve performance characteristics of the device, for example, by controlling such parameters as pump speed, flow rate and pumping time, which can correspondingly affect the temperature of the sensor, the fluid flow characteristics (e.g., turbulence at the sensor), and the like. Given the fact that the sensitivity of many nanoparticle-based sensors are temperature dependent, such features can permit the analyte sensitivity range to be improved without sacrificing precision.

System with Sensor on Detachable Insertion Member

Figure 13:
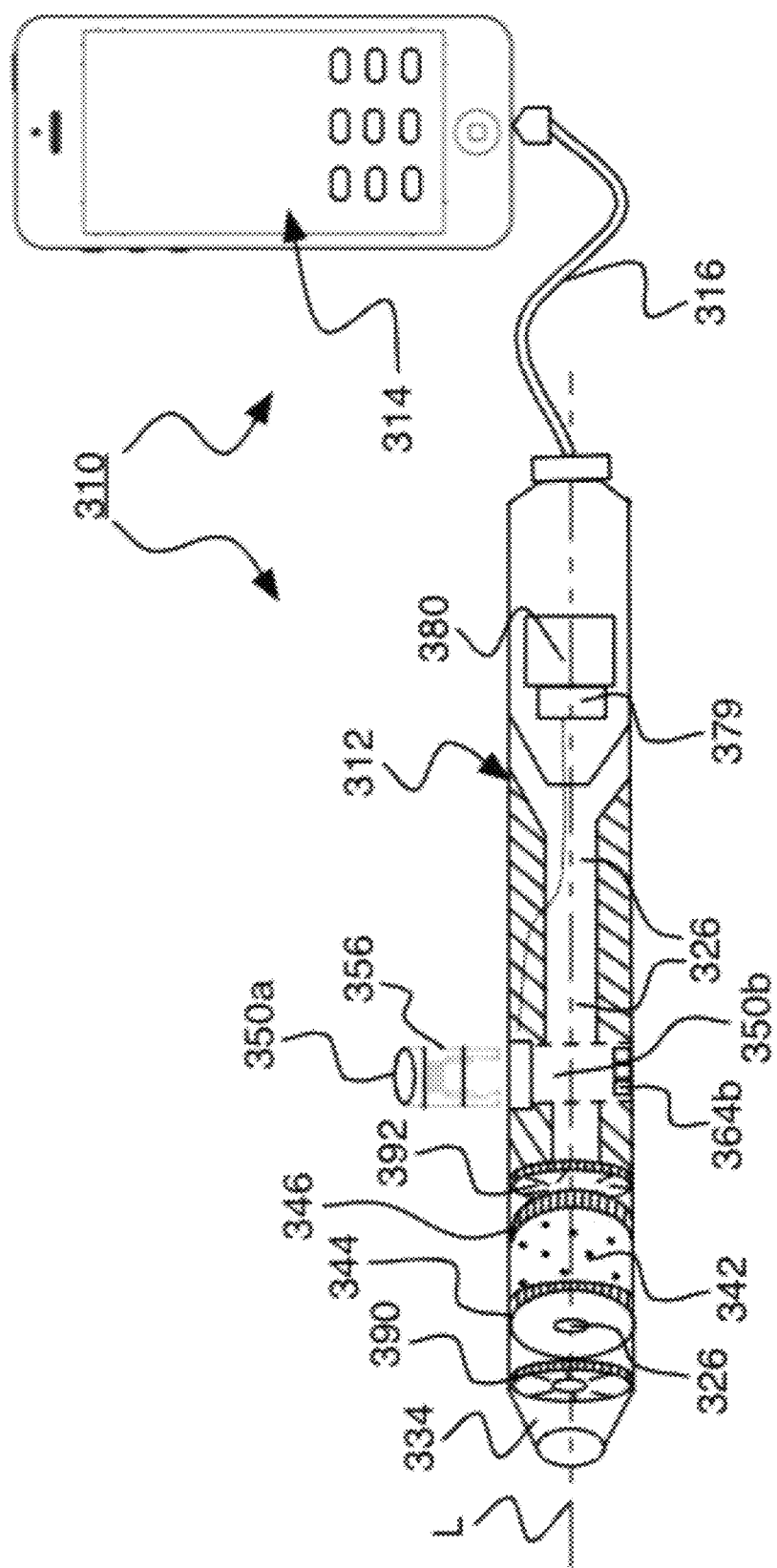
FIG. 13 is a pictorial view of another breath acetone measurement system according to a presently preferred embodiment of an aspect of the invention, including a side cutaway view of a measurement device that is part of the system, in which the measurement device comprises a detachable nanoparticle-based sensor subsystem.

A system 310 according to another embodiment is shown in FIG. 13. System 310 is very similar to system 10, including many of the same components, including one-way valves 90 and 92. Accordingly, numerals used to identify features of the system 310 are incremented by a factor of three hundred (300) to identify like features of the system 10. System 310 differs from system 10 primarily in that the nanoparticle-based sensor (sensor 50 in system 10) is disposed on a detachable or removable insertion member, here a cartridge 350a, that is inserted into an insertion aperture, here insertion slot 350b.

Figure 14A:
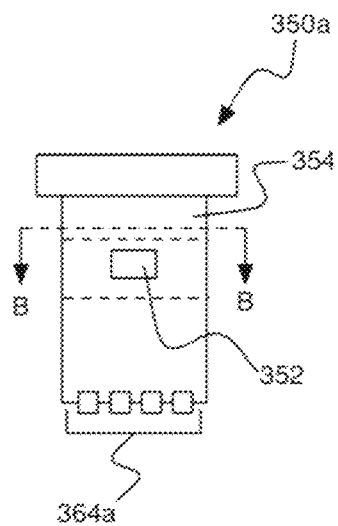
FIGS. 14A-14C show an expanded view of the nanoparticle-based sensor subsystem of FIG. 13 and a section of the measurement device into which the nanoparticle-based sensor subsystem is detachably inserted.
Figure 14B:
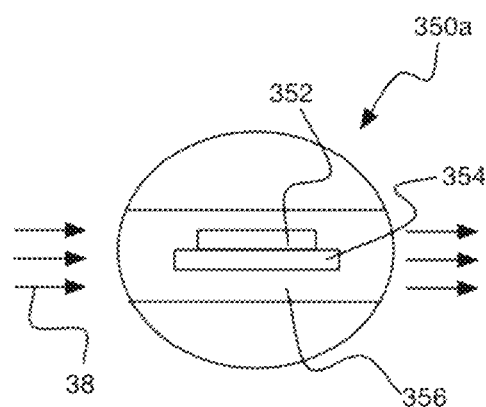
Figure 14C:
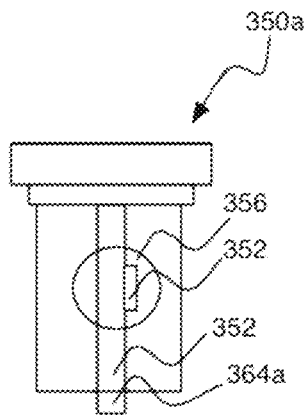

FIG. 14 shows various views of removable sensor cartridge 350a. Sensor cartridge 350a comprises a substantially cylindrical member that comprises a handle at the top (that remains outside the housing after insertion into insertion slot 350b) and a cylindrical body that extends down into the similarly-substantially cylindrical insertion slot 350b. Sensor cartridge 350a comprises a nanoparticle-based sensor 352 disposed on substantially planar PCB 354 that comprises edge connectors 364a (essentially identical to connectors 64 in FIGS. 2-3). Sensor cartridge 350a comprises a substantially cylindrical channel 356 perpendicular to its long axis so that, when cartridge 356 is in its fully inserted and secured position in insertion slot 350b, flow channel 326 is aligned with channel 356 so that the breath sample flows through channel 356 as part of flow channel 326 and in the process contacts sensor 352. When cartridge 350a is fully inserted into insertion slot 305b, edge connector 364a contacts corresponding contacts 364b at the bottom of insertion slot 350b, which places sensor 352 in operative communication with measurement device PCT 380.

System with Dual Sensors

In accordance with another aspect of the invention, systems, devices and methods are provided for measuring multiple analytes with a single device, and wherein protective and risk mitigation features as described herein are embodied. There are many examples of applications in which advantage may be found in measuring multiple analytes with a signal portable breath analyte measurement device. Acetone, oxygen and/or carbon dioxide, for example, may be used to monitor fat metabolism. Monitoring oxygen or carbon dioxide can provide information about an individual's basal metabolic rate. The basal metabolic rate varies, especially when an individual has made changes in his or her diet or exercise program. A combined acetone and oxygen device, therefore, may provide a physician or user with increased information and enable more informed nutritional and weight loss intervention programs.

Under certain physiological circumstances, acetone and isopropanol are in a state of chemical equilibrium. If acetone levels increase, the reverse reaction may occur and acetone may be converted into isopropanol. This has been observed with alcohol breath analyzers used for "driving under the influence" ("DUI") purposes. Even if the DUI breathalyzer is not sensitive to acetone, if a user is in a state with elevated ketone levels, such as diabetic ketoacidosis, acetone may be converted into isopropanol, which is an alcohol, and therefore detectable by the breathalyzer. Thus, elevated levels of breath acetone may result in a false positive by a DUI breathalyzer. When acetone is converted to isopropanol, however, a second problem can exist. When this conversion occurs, a breath acetone sensor may under-report the levels of breath acetone. For these situations, the sum total of breath isopropanol levels and breath acetone levels may actually serve as a better indicator of ketone levels than breath acetone alone. Accordingly, a dual-analyte embodiment that senses acetone and isopropanol has tremendous importance, particularly in critical care situations where acetone levels are extremely high and where acetone may be converted to isopropanol.

In other cases, measuring acetone in connection with other analytes, such as ammonia, isoprene, and markers of oxidative stress, can enable superior health monitoring. In the case of diabetes, for instance, monitoring breath acetone, ammonia, and isoprene can serve as a rapid means to determine blood ketone, creatinine or blood-urea-nitrogen ("BUN"), and cholesterol levels.

A hand-held breath analyzer that senses multiple analytes may be useful to monitor seemingly unrelated disease states, for example, diabetes and asthma. Such a device may utilize disposable cartridges that are application-specific. A single family may purchase a single hand-held device and utilize this device with application-specific cartridges. In this way, one individual may monitor his or her asthma and another individual may use the same device to monitor his or her diabetes.

It may also be a second sensing device that senses an interfering substance. The information from the second sensing device may be used by the processing device to characterize the analyte.

In addition, one also may wish to include a second sensor so that one of the sensors can serve as a reference. As an example, the first sensor may be constructed or selected to be selective for acetone, whereas the second sensor may be selective to an acetone interferent, such as water vapor. The sample breath sample is contact with each sensor, but the first sensor measures the acetone concentration while the second sensor measures the concentration of water vapor and thus the amount of interferent in the sample. This would permit the user or an analyst to subtract out the effects of the water vapor to obtain a normalized acetone measurement with respect to other breath samples having relatively more or less humidity.

Figure 15:
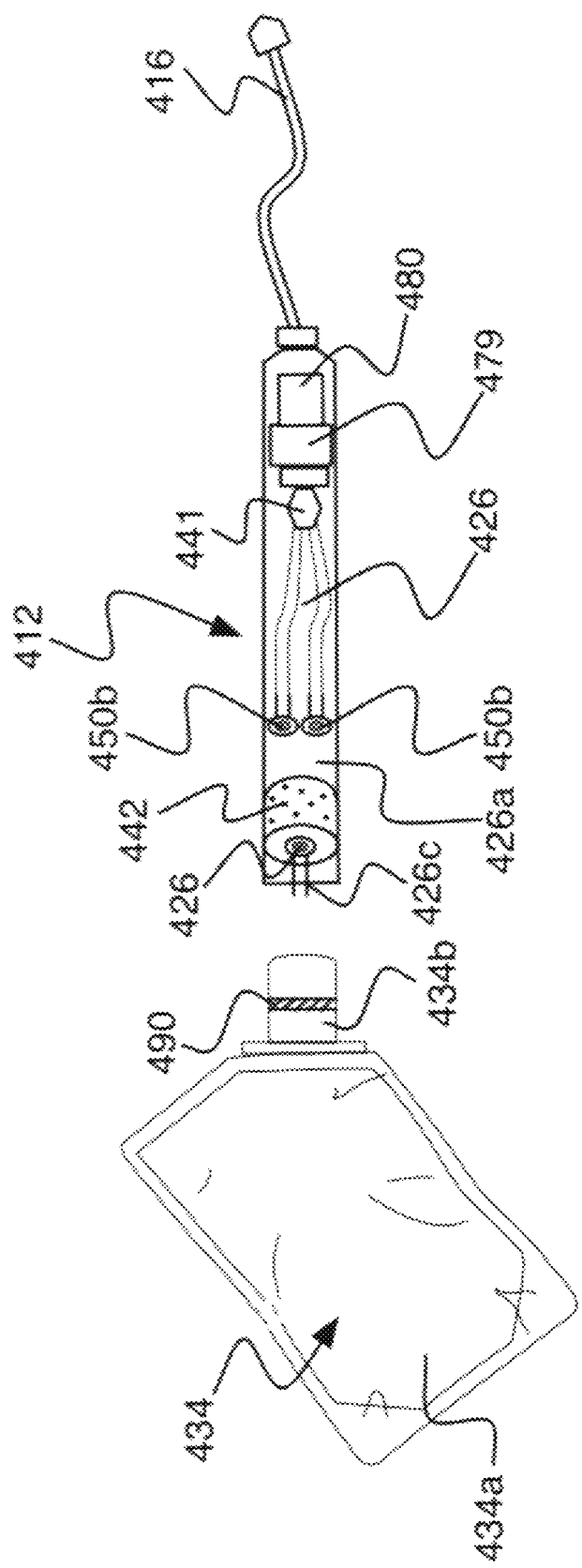
FIG. 15 is a pictorial view of still another breath acetone measurement system according to one embodiment, including a side cutaway view of a measurement device that is part of the system, in which the measurement device comprises two nanoparticle-based sensors.

A system 410 according to another embodiment is shown in FIG. 15. System 410 is very similar to system 10, including many of the same components. Accordingly, numerals used to identify features of the system 400 are incremented by a factor of four hundred (400) to identify like features of the system 10. The system 410 differs in that system 410 comprises at least two sensors subsystems, e.g., a nanoparticle-based sensor subsystem 450a and a second sensor subsystem 450b, which may include a nanoparticle-based sensor but which may comprise other types of sensors. Each sensor subsystem comprises a sensor disposed in the flow path or in fluid communication with it. A pump 441 can be disposed downstream of sensor subsystems 450a and b to induce flow of the breath sample past the sensors and to contact them to obtain the analyte measurements.

In this embodiment, the breath sample can be inputted into measurement device 412 directly or via a breath bag 434, past one-way valve 290 via posts 426c and into flow path 426. The sample may flow through conditioning device 442 before entering chamber 426a and into contact with the sensors. The sample is then vented as shown in FIGS. 1 and 10.

System with Non-Linear Flow Path

Figure 16:
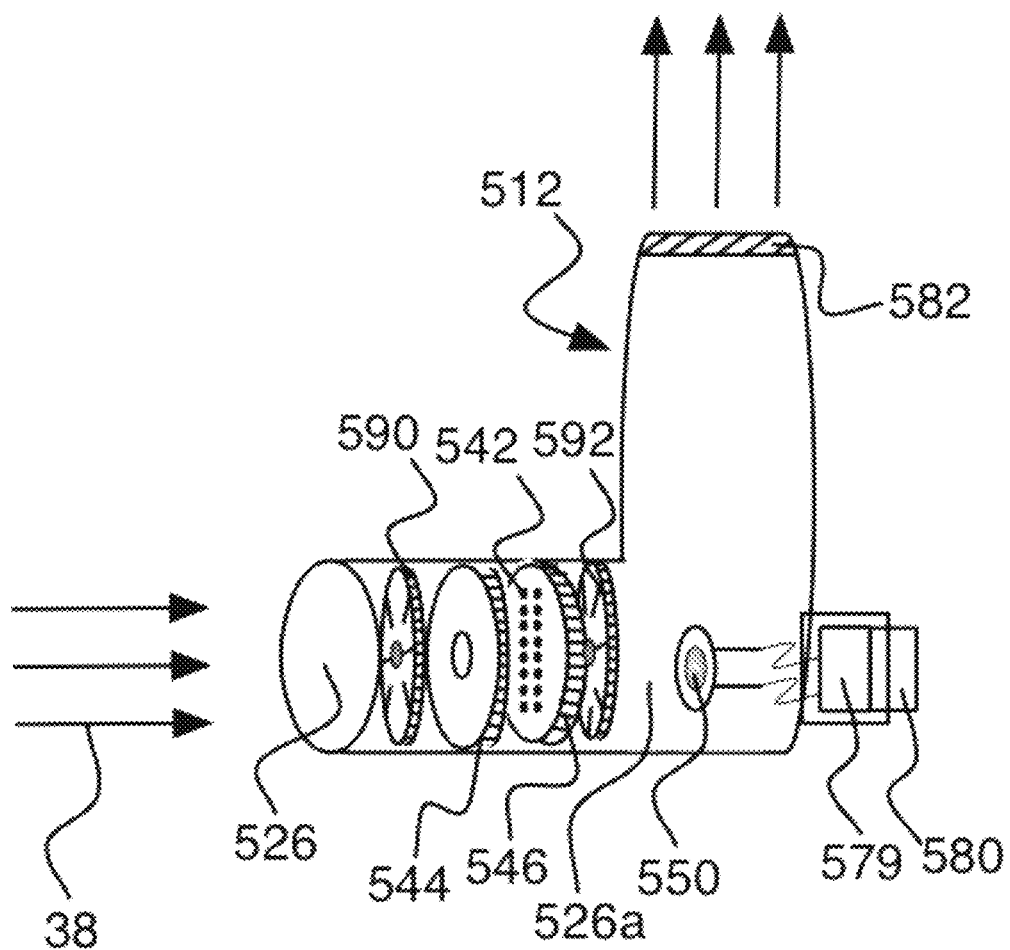
FIG. 16 is a pictorial view of yet another breath acetone measurement system according to one embodiment, including a side cutaway view of a measurement device that is part of the system, in which the system comprises a non-linear flow path.

A system 510 according to another embodiment is shown in FIG. 16. System 510 is very similar to system 10, including many of the same components. Accordingly, numerals used to identify features of the system 500 are incremented by a factor of five hundred (500) to identify like features of the system 10. The system 510 includes a non-linear flow path, comprising a first flow path 526a, which delivers the breath sample to nanoparticle-based sensor 550, and a second flow path 526b, which continues the flow path to a one-way exit port valve 582.

System with Heart Rate Monitor

Figure 17:
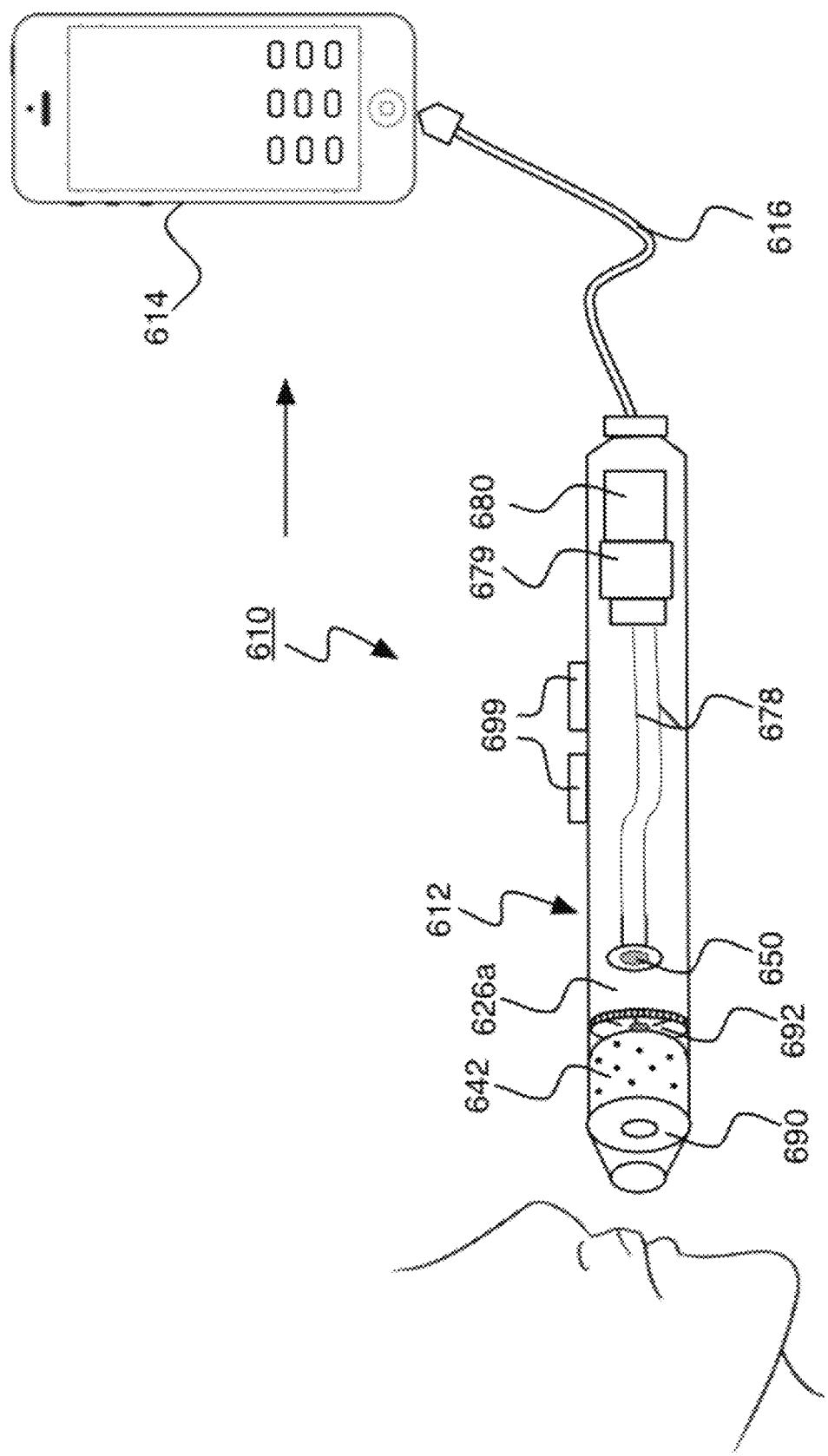
FIG. 17 is a pictorial view of another breath acetone measurement system according one embodiment, including a side cutaway view of a measurement device that is part of the system, in which the measurement device comprises an integrated heart rate monitor.

A system 610 according to another embodiment is shown in FIG. 17. System 610 is very similar to system 10, including many of the same components. Accordingly, numerals used to identify features of the system 600 are incremented by a factor of six hundred (600) to identify like features of the system 10.

System 610 differs from system 10, however, in that system 610 includes a heart rate monitor for measuring the heart rate of the user while the user uses the measurement device 612 to measure breath acetone concentration. Heart rate monitor comprises a pair of pads 699 disposed on the exterior of device housing 620.

Material on Purging and Multiple Conditioning Devices

In certain instances, once the nanoparticle-based sensor has been exposed to the breath sample containing the acetone analyte, it may be necessary to purge the conduit of the gas. This may be necessary for a variety of reasons. For example, in breath analysis, especially if the breath has not been stripped of moisture or bacteria, it may be important to remove any residual water/bacteria from the sensor and/or the conduit so as to prevent corrosion or contamination.

Purging the conduit can also allow for reverse reactions or physical phenomena to occur, which may help to bring the overall system back to equilibrium. For example, if an adsorption interactant were selected, exposure to the analyte will promote adsorption, but exposure to a purging gas stream may help promote desorption.

In other instances, prior to exposure to the gas containing the analyte, it is advantageous for the analyte interactant to be exposed to a priming stream. For example, water may be passed through the conduit to allow water and the immobilized interactant to react, thereby forming a species that will interact with the analyte of interest. This is particularly desirable when an interactant is selected because it is stable, but perhaps needs to be activated to become truly reactive with the analyte.

It may also be desirable to utilize a priming stream to establish the temperature and flow regime. For example, if the overall device is placed in an environment where the environmental conditions are substantially different than those of its prior use, a priming stream may be helpful to calibrate the device.

Figure 18:
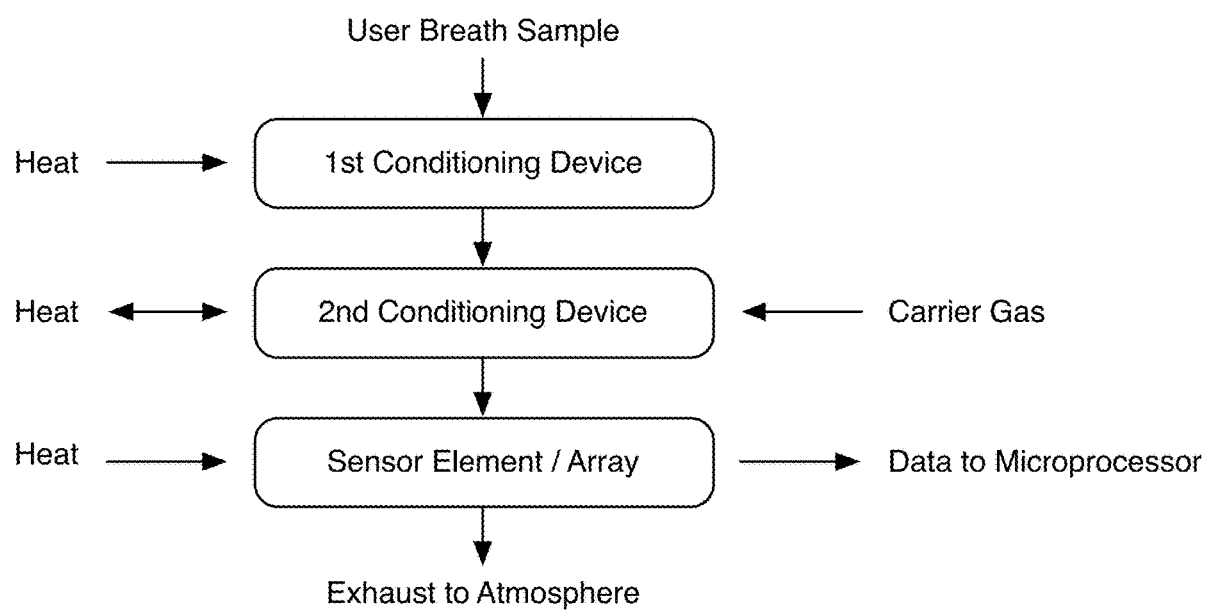
FIG. 18 is a functional block diagram illustrating the configuration of an embodiment that can be used in conjunction with a nanoparticle-based sensor.

FIG. 18 is a functional block diagram illustrating the configuration of an embodiment that can be used in conjunction with a nanoparticle-based sensor. A user breathes into a fluid collecting device and the sample of breath passes into a first conditioning device containing a moisture-removal function. The sample then passes into a second conditioning device containing an analyte-retaining sorbent material. The analyte is thus retained in the second conditioning device while the remainder of the sample of breath passes over the heated sensor element and then exits the breath analysis device. The second conditioning device is then isolated from the flow path and heated. Carrier gas is allowed to pass over the second conditioning device, removing the analyte from the second conditioning device and directing it over the sensing device comprising a nanoparticle-based sensor, which may include a single element or an array. Changes in the characteristics of the sensing device are then transmitted to a microprocessor for analysis, data logging, storage, and/or transmission.

Figure 19:
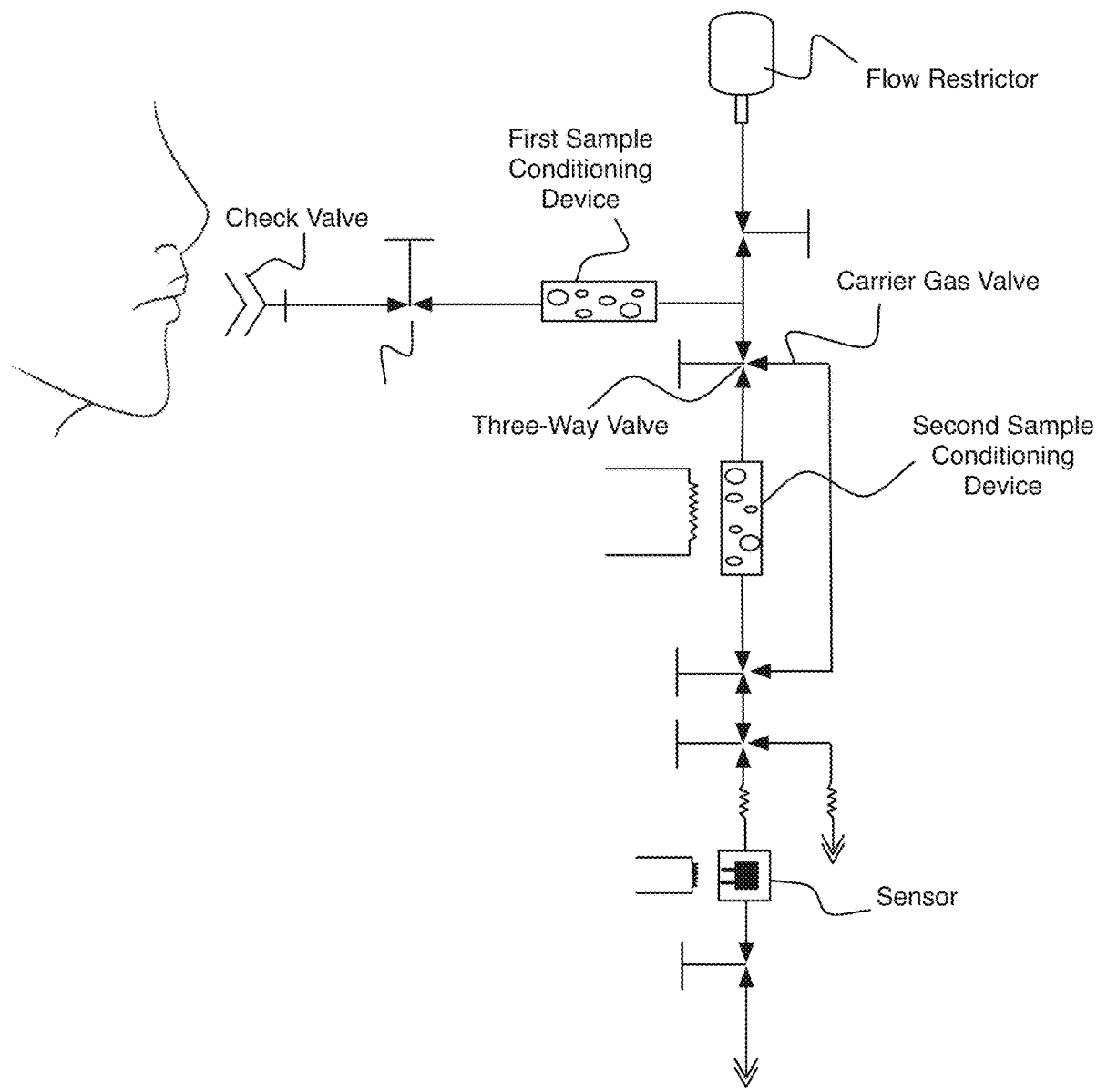
FIG. 19 is a schematic representation of an embodiment that utilizes two conditioning devices and a sensing device.

FIG. 19 is an embodiment that utilizes two conditioning devices and a nanoparticle-based sensor. In this embodiment, a user blows into the fluid collecting device through a check valve. The sample of breath passes through a first sample conditioning device and then through a second sample conditioning device. The breath sample then passes through a 3-way valve, then through a flow restrictor, and exits the breath analysis device. The resistance to breath flow is controlled by the packing density of the two sample conditioning columns and the flow restrictor. The fluid resistance is set by the flow restrictor to allow comfortable and rapid sampling of the users' breath. Once the sample has been dehumidified by the first sample conditioning device and trapped into the second sample conditioning device, the second sample conditioning device is then isolated by the three-way valve. A carrier gas valve is opened, which then bypasses the second sample conditioning device and is then directed to flow over the sensing device and to exit the device. The system thus collects baseline sensor data, showing the electrical resistance changes with time for a sample with no analyte. While the carrier is bypassing the second conditioning device, the second conditioning device is being heated. Once the appropriate temperature is reached, the valves are switched to pass the carrier gas through the second conditioning device and onto the sensing device. The analyte in the gas stream interacts with the sensing device in a manner that is reproducible and dependent on the concentration of the analyte released from the second conditioning device.

Such an apparatus may be used to sense acetone in breath. In this embodiment, a mouthpiece is coupled to a first conditioning device comprised of a desiccant material within a flow conduit or chamber, wherein the flow conduit or chamber may be under thermal control whereby the desiccant material may be heated and/or cooled. The desiccant material can be calcium chloride (200 mg). A second conditioning device is positioned downstream of the first conditioning device and consists of a sorbent material within a flow conduit or chamber, such as Tenax TA (250 mg). The second conditioning device is under thermal control whereby the sorbent material may be heated and/or cooled. A disposable gas cylinder or alternative gas source (such as a pump utilizing ambient air) is connected to the flow circuit by a one-way valve, and automated 3-way valves allow computer-controlled direction of the gas streams within the acetone-sensing device. A user blows into the mouthpiece, whereby the exhaled breath gases pass through the desiccant held at 40° C. and into the sorbent trap held at 30° C. Exhaled moisture is thus first captured into the desiccant material and the residual moisture passes through the sorbent material. Acetone is retained in the sorbent material. The second conditioning device is then isolated from the flow path using two 3-way valves and the sorbent material is heated to 85° C. The one-way valve is then opened to allow passage of gas from the disposable cylinder or alternate gas source over the nanoparticle-based sensor, bypassing the sorbent trap. The gas in the cylinder may comprise 21% v/v oxygen in a balance of nitrogen, charged with a set pressure to allow flow from the cylinder to be repeatable for each replacement of the cylinder. The nanoparticle-based sensor is operated with the nanoparticle material held at 160° C. The gas from the disposable cylinder flows over the nanoparticle-based sensor and creates a baseline signal, which is logged by a microcontroller. Once a sufficient baseline has been logged and the second conditioning device containing the sorbent material has attained a temperature of 85° C., the 3-way valves are actuated to put the second conditioning device in-line with the flowing gas stream of a known composition. Acetone is thus swept out of the sorbent material and over the nanomaterial sensing element. A first deflection in the sensor signal trace is due to the flow artifact created by the switching of the valves, but the second deflection in the sensor signal trace has a magnitude of deflection that is proportional to the acetone fraction in the breath sample. The acetone displaces oxygen in a chemical reaction occurring at the nanomaterial surface and this causes a decrease in the resistance of the nanomaterial. A circuit comprising a low current constant current source and high input impedance voltmeter measures the change in resistance and this change corresponds to the concentration of acetone in the sample. The nanoparticle-based sensor is comprised of gamma-phase ferric oxide ($Fe_2O_3$) nanoparticles manufactured using a sol-gel process with an average particle diameter of 20 nm. The nanoparticles are disposed on a planar alumina substrate onto screen-printed gold contacts, which are in electrical communication with screen printed silver lead traces. The nanoparticle material is deposited over the gold contacts, bridging a 1 mm electrode gap. The nanoparticle material is approximately 150 micrometers thick, 2 mm wide, and 3 mm long.

The apparatus described above can be modified to sense ethanol, isopropanol, or other analytes, in breath. In the case of an embodiment for ethanol sensing, an ethanol-sensitive nanoparticle material is used and the elution parameters are modified. In this embodiment, a mouthpiece is coupled to a first conditioning device comprised of a desiccant material within a flow conduit or chamber, wherein the flow conduit or chamber is under thermal control whereby the desiccant material may be heated and/or cooled. The desiccant material can be calcium chloride (200 mg). A second conditioning device is positioned downstream of the first conditioning device and consists of a sorbent material within a flow conduit or chamber, such as Tenax TA (250 mg). The second conditioning device is under thermal control whereby the sorbent material may be heated and/or cooled. A disposable gas cylinder or suitable alternative gas source such as a pump in communication with ambient air is connected to the flow circuit by a one-way valve, and automated 3-way valves allow computer-controlled direction of the gas streams within the ethanol-sensing device. A user blows into the mouthpiece, whereby the exhaled breath gases pass through the desiccant held at 40° C. and into the sorbent trap held at 30° C. Exhaled moisture is thus first captured into the desiccant material and the residual moisture passes through the sorbent material. Ethanol is retained in the sorbent material. The second conditioning device is then isolated from the flow path using two 3-way valves and the sorbent material is heated to 50° C. The one-way valve is then opened to allow passage of gas from the disposable cylinder over the nanoparticle-based sensor, bypassing the sorbent trap. The gas in the cylinder may comprise 21% v/v oxygen in a balance of nitrogen, charged with a set pressure to allow flow from the cylinder to be repeatable for each replacement of the cylinder. The nanoparticle-based sensor is operated with the nanoparticle material held at 200° C. The gas from the disposable cylinder or alternative gas source flows over the nanoparticle-based sensor and creates a baseline signal, which is logged by a microcontroller. Once a sufficient baseline has been logged and the second conditioning device containing the sorbent material has attained a temperature of 50° C., the 3-way valves are actuated to put the second conditioning device in-line with the flowing gas stream of a known composition. Ethanol is thus swept out of the sorbent material and over the nanomaterial-sensing element. A first deflection in the sensor signal trace is due to the flow artifact created by the switching of the valves, but the second deflection in the sensor signal trace has a magnitude of deflection that is proportional to the ethanol fraction in the breath sample. The ethanol displaces oxygen in a chemical reaction occurring at the nanomaterial surface and this causes a decrease in the resistance of the nanomaterial. A circuit comprising a low current constant current source and high input impedance voltmeter measures the change in resistance and this change corresponds to the concentration of ethanol in the sample. The nanoparticle-based sensor is comprised of gamma-phase ferric oxide ($Fe_2O_3$) nanoparticles manufactured using a sol-gel process with an average particle diameter of 20 nm doped with 33% w titanium dioxide ($TiO_2$, anatase). The nanoparticles are disposed on a planar alumina substrate onto screen-printed gold contacts, which are in electrical communication with screen printed silver lead traces. The nanoparticle material is deposited over the gold contacts, bridging a 1 mm electrode gap. The nanoparticle material is approximately 150 micrometers thick, 2 mm wide, and 3 mm long.

The apparatus is not limited to sensing a single analyte. Two-analyte sensing capacity of a nanoparticle-based sensor can be achieved using the general components as described above for acetone and isopropanol sensing, but using a two-step elution procedure and both acetone and isopropanol-sensitive nanoparticle-based sensor materials. In this case, a mouthpiece is coupled to a first conditioning device comprised of a desiccant material within a flow conduit or chamber, wherein the flow conduit or chamber is under thermal control whereby the desiccant material may be heated and/or cooled. The desiccant material is calcium chloride (200 mg). A second conditioning device is positioned downstream of the first conditioning device and consists of a sorbent material within a flow conduit or chamber, such as Tenax TA (250 mg). The second conditioning device is under thermal control whereby the sorbent material can be heated and cooled. A disposable gas cylinder or suitable alternative gas source such as a pump in communication with ambient air is connected to the flow circuit by a one-way valve, and automated 3-way valves allow computer-controlled direction of the gas streams within the two-analyte sensing device. A user blows into the mouthpiece, whereby the exhaled breath gases pass through the desiccant held at 40° C. and into the sorbent trap held at 30° C. Exhaled moisture is thus first captured into the desiccant material and the residual moisture passes through the sorbent material. Acetone and ethanol are retained in the sorbent material. The second conditioning device is then isolated from the flow path using two 3-way valves and the sorbent material is heated to 50° C. The one-way valve is then opened to allow passage of gas from the disposable cylinder or an alternative gas source over the nanoparticle-based sensor, bypassing the sorbent trap. The gas in the cylinder or the ambient air comprises 21% v/v oxygen in a balance of nitrogen, charged with a set pressure to allow flow from the cylinder to be repeatable for each replacement of the cylinder. A first nanoparticle-based sensor for isopropanol is operated with the nanoparticle material held at 200° C. A second nanoparticle-based sensor for acetone is operated with the nanoparticle material held at 160° C. The gas from the disposable cylinder or alternative gas source flows over the nanoparticle-based sensors and creates baseline signals, which are logged by a microcontroller. Once a sufficient baseline has been logged and the second conditioning device containing the sorbent material has attained a temperature of 50° C., the 3-way valves are actuated to put the second conditioning device in-line with the flowing gas stream of a known composition. Isopropanol is thus swept out of the sorbent material and over the nanomaterial sensing element. A first deflection in the sensor signal trace is due to the flow artifact created by the switching of the valves, but the second deflection in the sensor signal trace has a magnitude of deflection that is proportional to the isopropanol fraction in the breath sample. The isopropanol displaces oxygen in a chemical reaction occurring at the nanomaterial surface and this causes a decrease in the resistance of the nanomaterial. A circuit comprising a low current constant current source and high input impedance voltmeter measures the change in resistance and this change corresponds to the concentration of isopropanol in the sample. The second conditioning device is then re-isolated using the 3-way valves, and the sorbent material is heated to 85° C. Once the temperature has been obtained, the 3-way valves open to allow the carrier gas to displace the acetone from the sorbent, which then passes over the two sensors. As each sensor is sensitive in varying degree to both analytes, the sensor signals from both sensors are used to infer the concentration of both analytes in the sample. The acetone nanoparticle-based sensor is comprised of gamma-phase ferric oxide ($Fe_2O_3$) nanoparticles manufactured using a sol-gel process with an average particle diameter of 20 nm. The isopropanol nanoparticle-based sensor is comprised of gamma-phase ferric oxide ($Fe_2O_3$) nanoparticles manufactured using a sol-gel process with an average particle diameter of 20 nm doped with 33% w titanium dioxide ($TiO_2$, anatase). The nanoparticles are disposed on a planar alumina substrate onto screen-printed gold contacts, which are in electrical communication with screen printed silver lead traces. The nanoparticle material is deposited over the gold contacts, bridging a 1 mm electrode gap. The nanoparticle material is approximately 150 micrometers thick, 2 mm wide, and 3 mm long.

Figure 20:
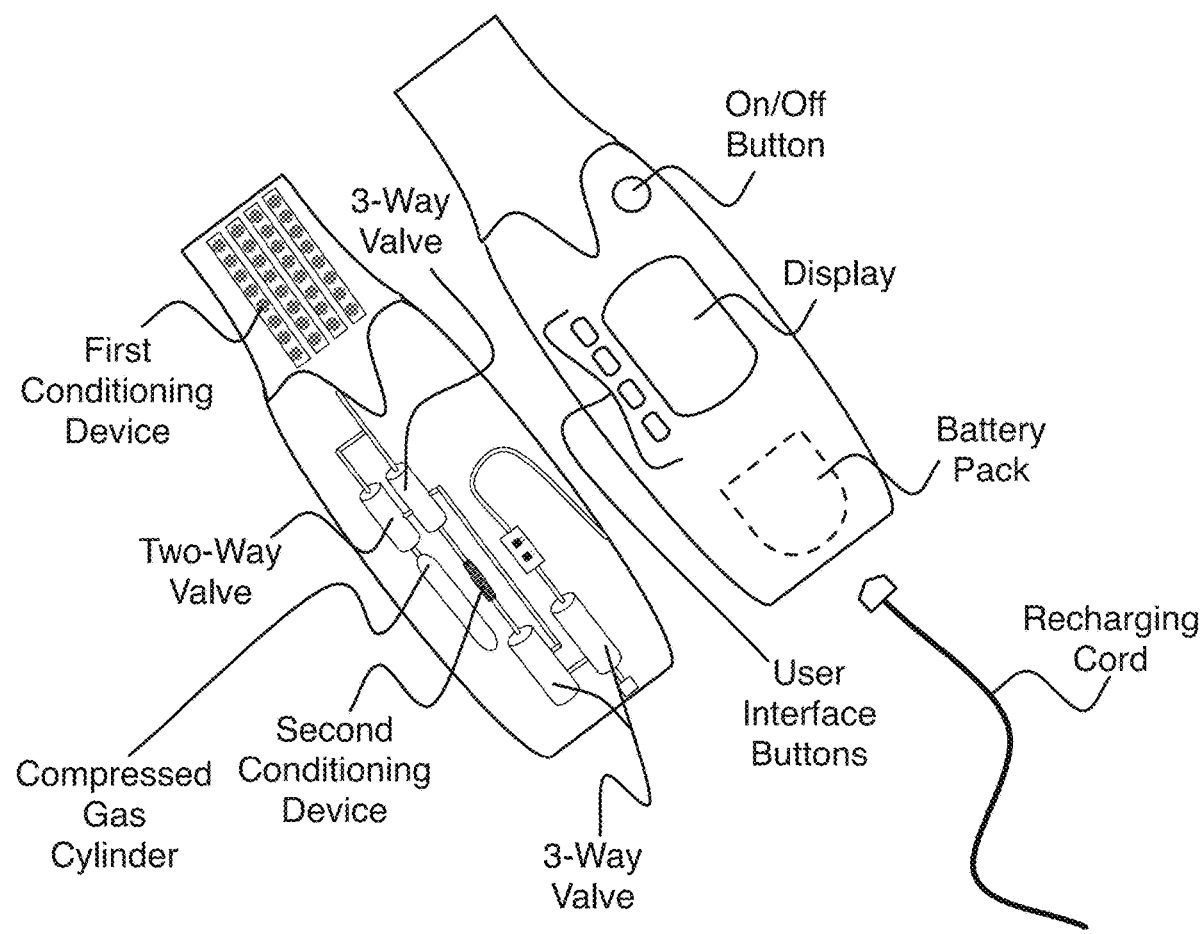
FIG. 20 illustrates an embodiment of a hand-held breath gas analyzer with a nanoparticle-based sensing device that embodies the configuration of FIG. 19.

FIG. 20 is an embodiment of a hand-held breath gas analyzer with a sensing device, such as a nanoparticle-based sensor. This hand-held embodiment of the breath gas analyzer is comprised of electronically-actuated valves, a first conditioning device embedded in a disposable mouthpiece, a second conditioning device, a two-element nanoparticle-based sensor array, a disposable/rechargeable compressed gas cylinder, fluidic interconnect components, a user display screen, and interface buttons. The battery pack, positioned on the top piece adjacent to the user display, is rechargeable.

Figure 21:
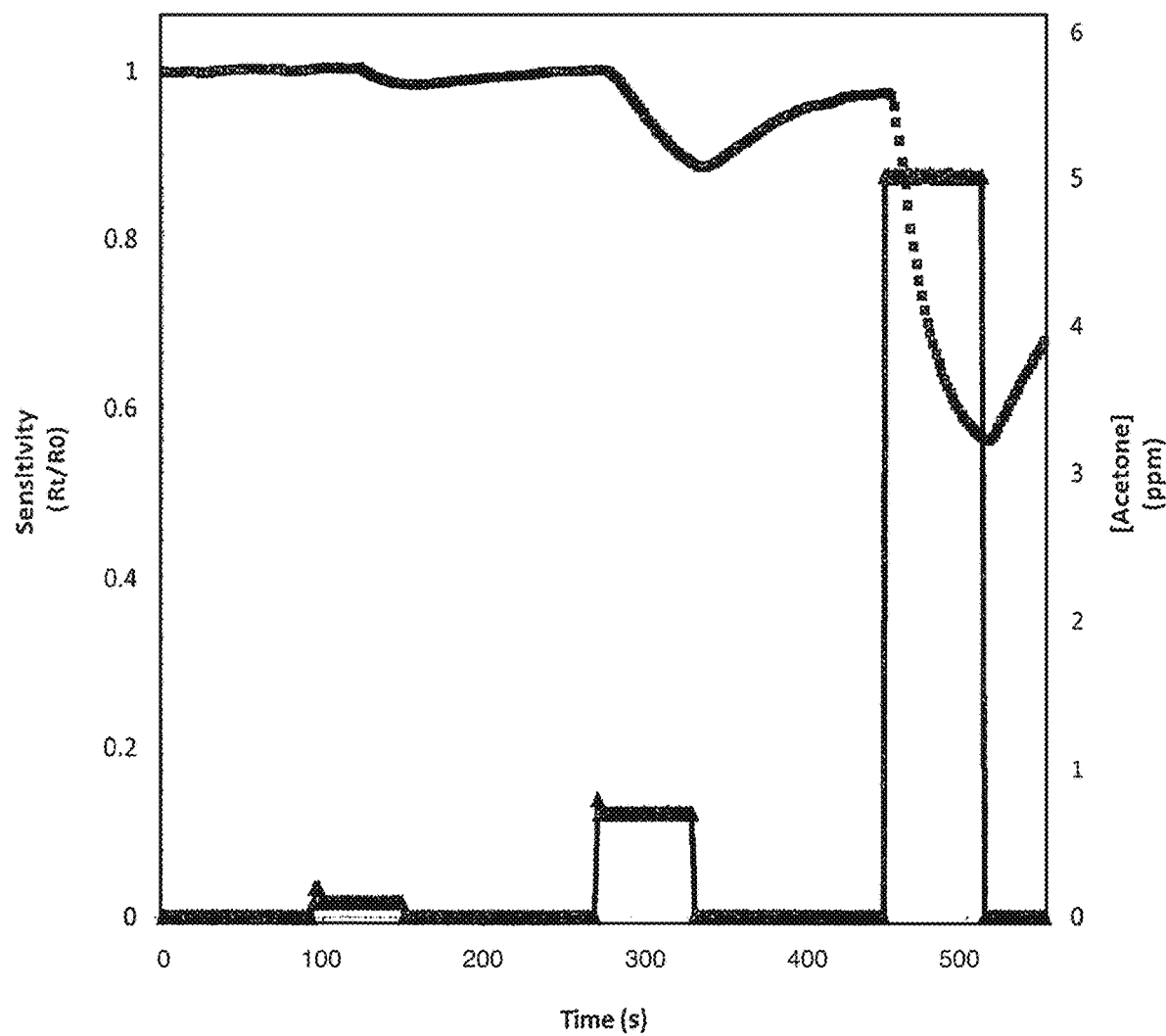
FIG. 21 is a graph showing the sensitivity to acetone of a nanoparticle-based sensor as disclosed herein.

FIG. 21 is a graph showing the sensitivity of an embodiment of a nanoparticle-based sensor to acetone. This embodiment comprises an $Fe_2O_3$ nanoparticle sensor. This sensor was tested in an environment with a continuous stream of gas (500 standard cubic centimeters per minute ("SCCM")) mixed from compressed sources via mass flow controllers (to final percent volumes of 18% $O_2$, 3% $CO_2$, ppm levels of acetone, balance $N_2$). Under dry, continuous gas streams, the sensitivity of the nanoparticle sensors to acetone is very high and stable.

Figure 22:
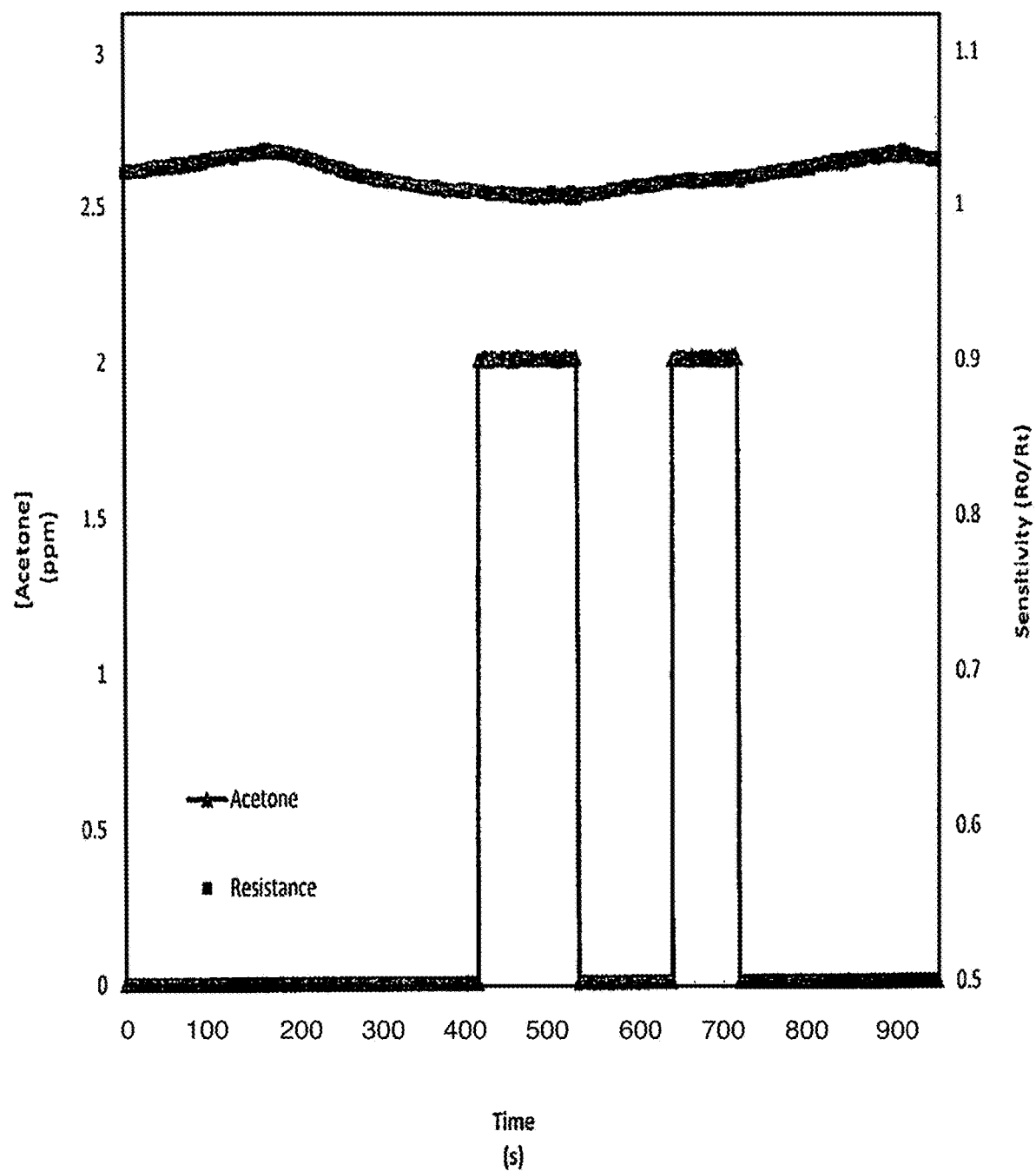
FIG. 22 is a graph showing the sensitivity to acetone of a nanoparticle-based sensor as disclosed herein.

FIG. 22 is a graph showing the sensitivity of an embodiment of a nanoparticle-based sensor to acetone. This embodiment comprised an $Fe_2O_3$ nanoparticle sensor. This sensor was tested with moderate amounts of humidity (20% relative humidity ("RH") at 37° C.) added to the continuously supplied simulated breath (18% $O_2$, 3% $CO_2$, ppm levels of acetone). The sensor response to even moderately high acetone concentrations (2 ppm in the figure) are severely impaired. The humidity chamber created a constant supply of 20% RH at 37° C. (roughly 40% RH at 25° C.) with a 3% fluctuation band. Humidity can be a significant deterrent of acetone detection using the nanoparticle-based sensor without humidity mitigation strategies.

Figure 23:
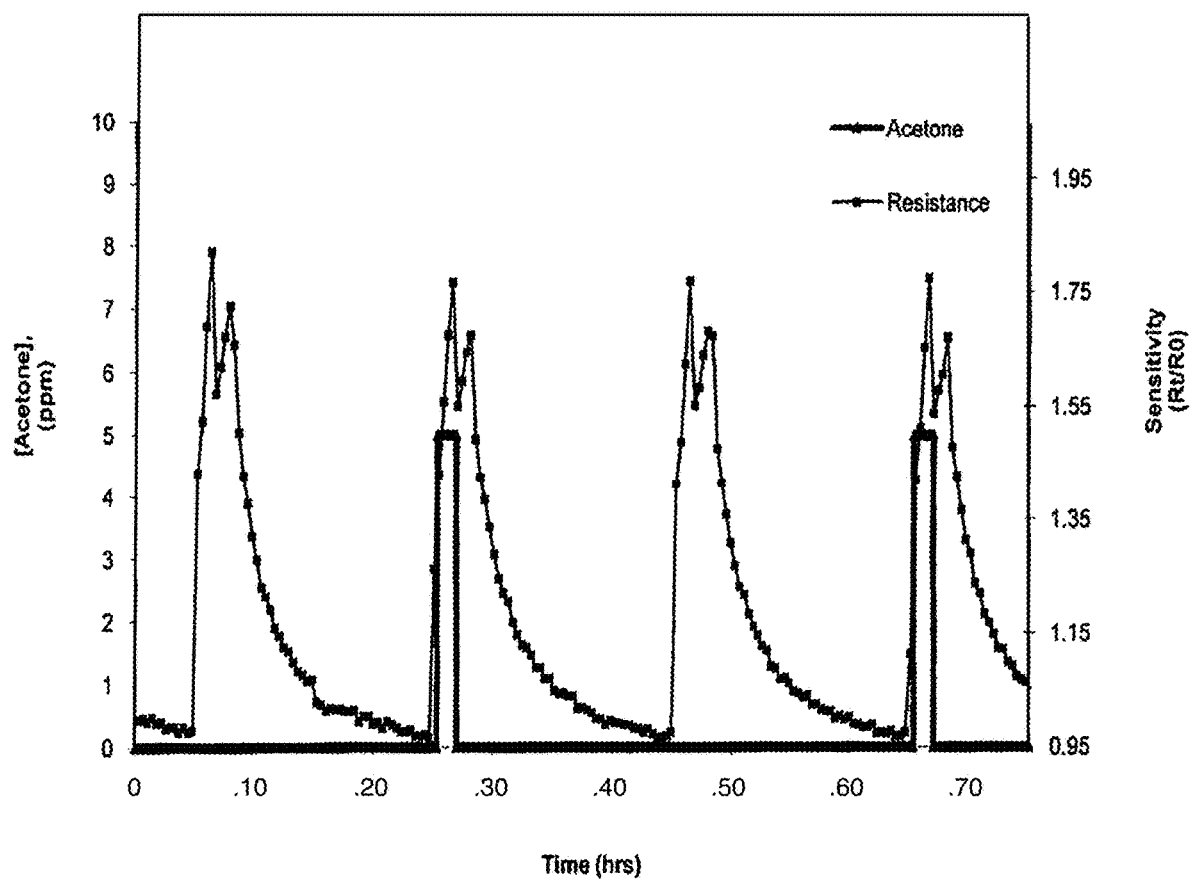
FIG. 23 is a graph showing the sensitivity to acetone of a nanoparticle-based as disclosed herein.

FIG. 23 is a graph showing the sensitivity of an embodiment of a nanoparticle-based sensor to acetone. This embodiment comprised an $Fe_2O_3$ nanoparticle sensor. The sensor was tested in a flow chamber with 21% v/v $O_2$ and then flow was stopped for a few minutes, simulating an operating mode whereby a hand-held sensor would be warming up in preparation for a breath sampling event. Then, the gas concentration was set at 18% $O_2$ and 3% $CO_2$, balance $N_2$, with acetone spikes where indicated. The sensor response to zero flow switched to sample flow (500 SCCM) with a concurrent change in $O_2$ concentration was dramatic. Sensor response to 5 ppm administrations of acetone are not visibly discernible under these pulsatile flow conditions. Immediately following the simulated breath sample, the sensor chamber was flushed with 21% $O_2$ in preparation for another resting state. Pulsatile flow is shown to be a significant deterrent of acetone detection without using flow and pressure mitigation strategies. Also, the sensitivity of the nanoparticle sensor to changes in oxygen concentration are strong, a fact that complicates breath analysis using semiconductor nanoparticles.

Figure 24:
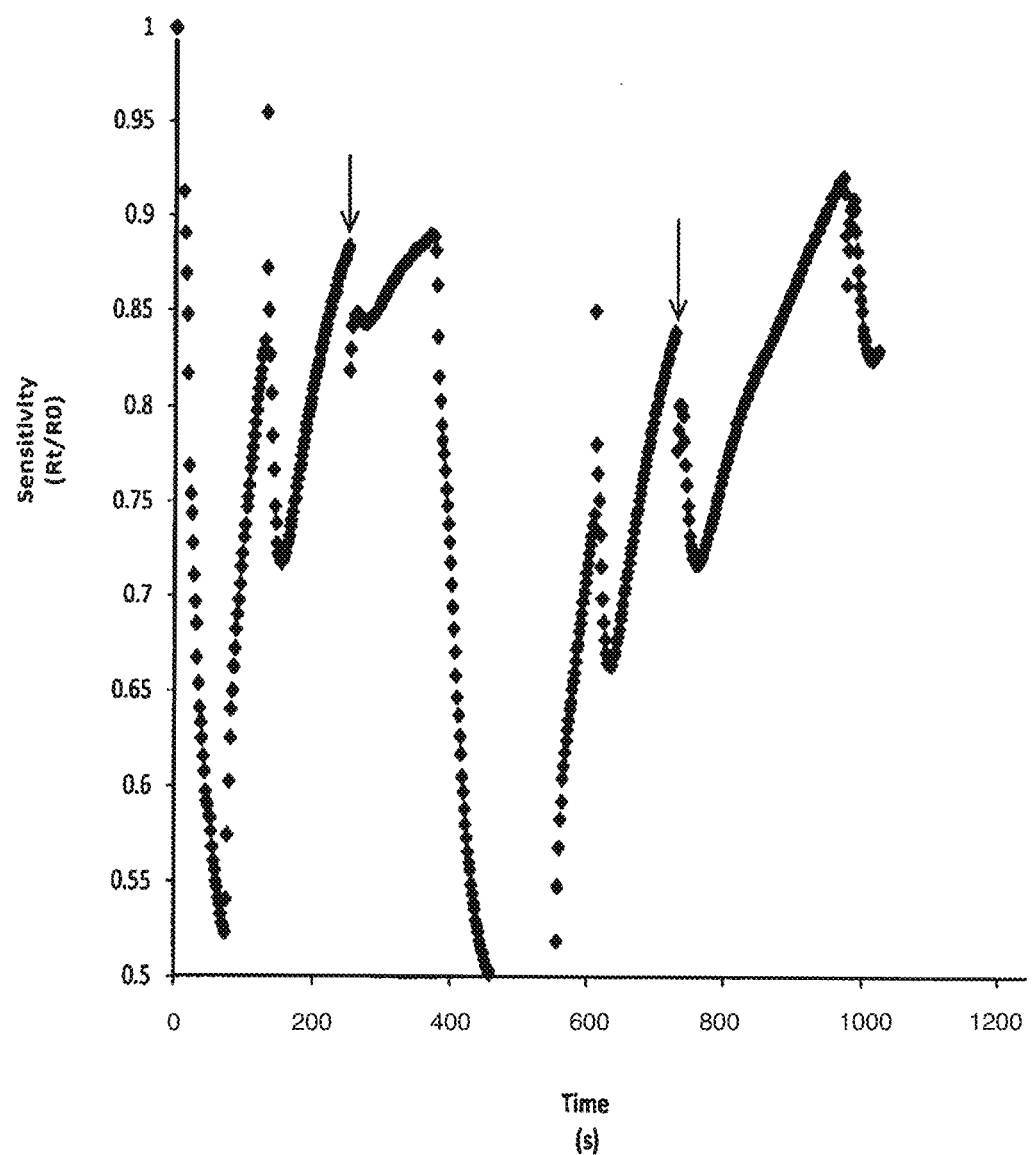
FIG. 24 is another graph showing the sensitivity to acetone of a nanoparticle-based sensor as disclosed herein.

FIG. 24 is a graph showing the sensitivity of an embodiment of a nanoparticle-based sensor to acetone. This embodiment comprised an $Fe_2O_3$ nanoparticle sensor, using a conditioning device. The response of the sensor element to the various stages of breath sampling, as described in FIG. 18, is shown in FIG. 23. Arrows indicate the time point wherein the three-way valves switch to allow the carrier gas to deliver the analyte to the sensor element. The sensitivity trace upstream of the arrow indicates a portion where a blank sample is administered to the sensor element, allowing the collection of baseline data. The sensitivity trace after the switch shows the sensor response to the gas stream with the swept analyte. After the artifact of switching passes, a downward deflection in the sensitivity is observed. The downward deflection caused by a 2 ppm analyte concentration is noticeably larger than that caused by the 0 ppm sample.

Figure 25:
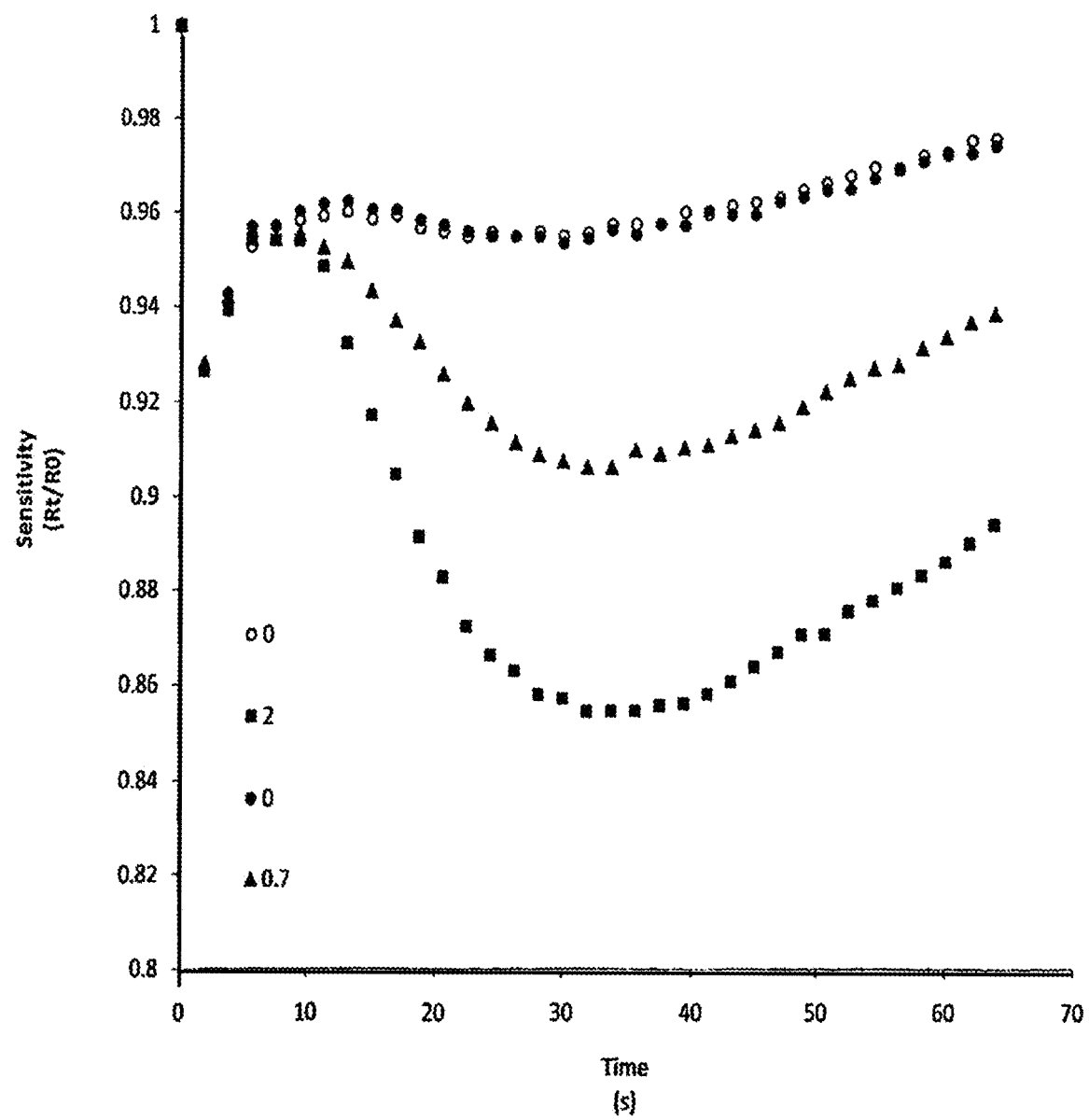
FIG. 25 is another graph showing the sensitivity to acetone of a nanoparticle-based sensor as disclosed herein.

FIG. 25 is a graph showing the sensitivity of an embodiment of a nanoparticle-based sensor to acetone. This embodiment again utilizes an $Fe_2O_3$ nanoparticle sensor and a conditioning device. A data processing scheme is presented and utilized for creating a dose response curve from the raw data traces as presented in FIG. 24. The last data point before the carrier gas switch-over is used for data normalization, a procedure which effectively removes minor baseline drifts. FIG. 25 was created by analyzing the raw traces from a blank breath sample (no acetone), a 2 ppm sample, another blank, and then a 0.7 ppm sample, separated by several minutes. The simulated breath consisted of 40% RH (at 37° C.), 18% $O_2$, and 3% $CO_2$ (balance nitrogen). 400 cc's of simulated breath were administered to the capture and release scheme, without the use of the first sample conditioning column (moisture removal column). Use of the moisture removal column enhances the sensor performance. The data presented in FIG. 25 represents the response of a nanoparticle-based sensor to acetone in simulated breath with characteristics that mimic human breath samples.

Figure 26:
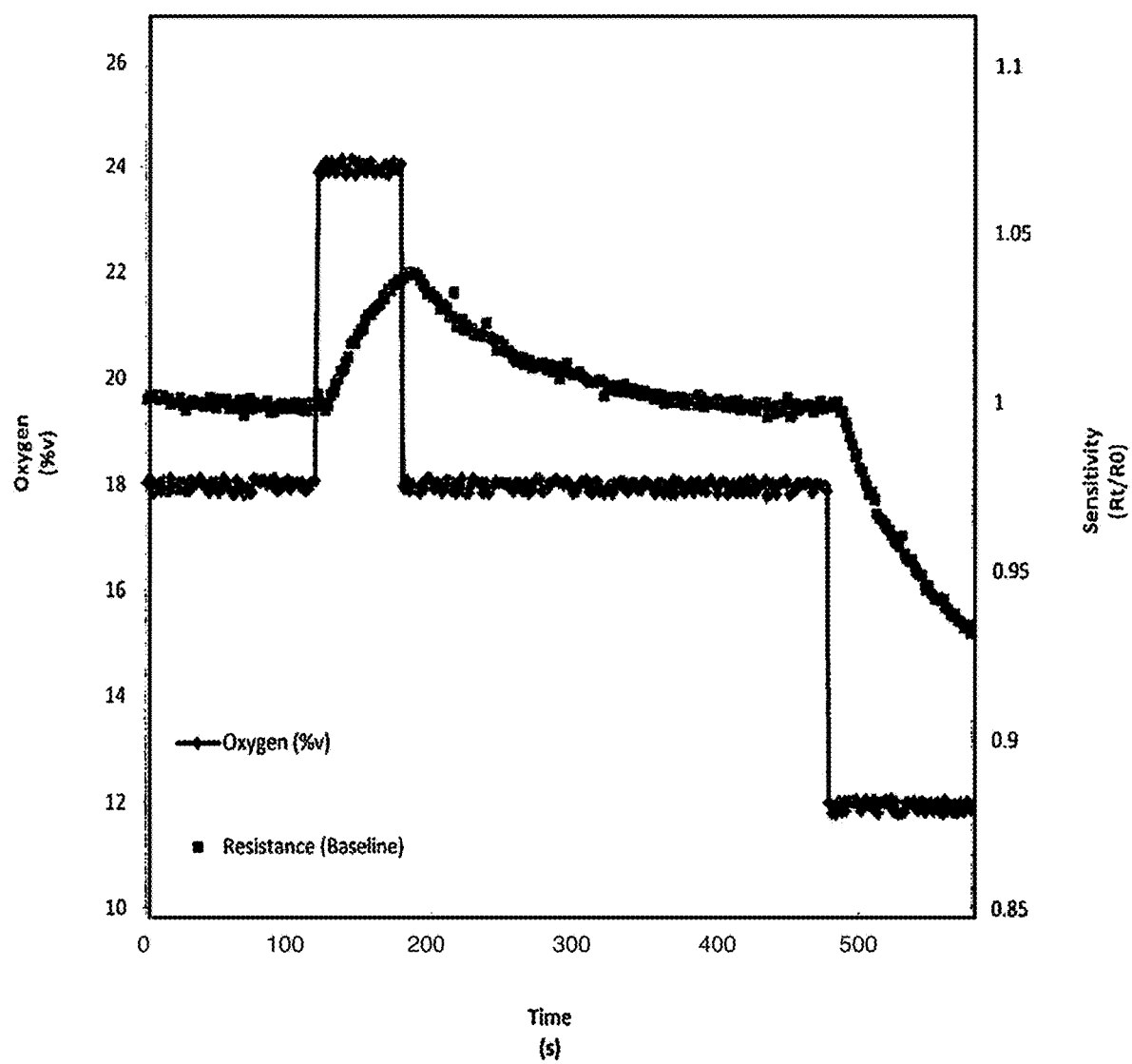
FIG. 26 is another graph showing the sensitivity to oxygen of a nanoparticle-based sensor as disclosed herein.

FIG. 26 is a graph showing the sensitivity of an embodiment of a nanoparticle-based sensor to oxygen. This embodiment again utilizes an $Fe_2O_3$ nanoparticle sensor and a conditioning device. The conditioning device is comprised of a calcium chloride desiccant (5 g). The oxygen was varied under a steady flow (500 SCCM) at RH of 40% at 37° C. (equivalent to roughly 80% RH at room temperature). The concentration of oxygen in the gas stream was varied between 18, 24, and 12% v. FIG. 26 demonstrates the ability of a nanoparticle-based sensor to measure oxygen in the presence of humidity.

Figure 27:
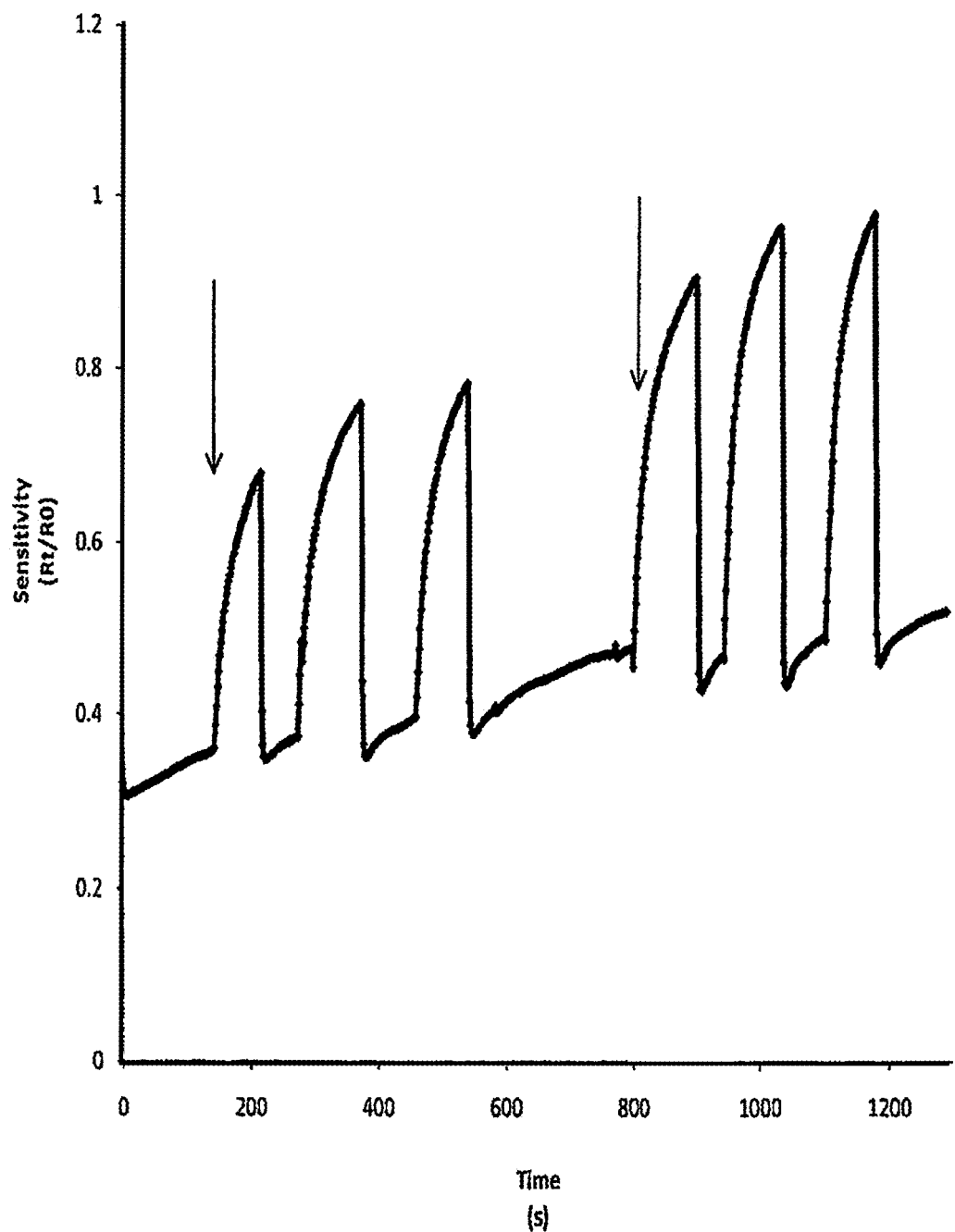
FIG. 27 is another graph showing the sensitivity to isopropanol of a nanoparticle-based sensor as disclosed herein.

FIG. 27 is a graph showing the sensitivity of an embodiment of a nanoparticle-based sensor to isopropyl alcohol. This embodiment uses a $SnO_2$ nanoparticle sensor. Carrier gas consisting of 18% v oxygen, 3% v $CO_2$, and a balance of nitrogen was alternately passed through the head space of two vials holding different mixtures of alcohol and water held at room temperature. The first arrow indicates the time when carrier gas flow was switched from a vial containing 0.225% v isopropanol in water to a vial containing 0.125% v isopropanol in water. Flow was subsequently alternated between the two vials a few times. Then, the vial containing 0.125% v isopropanol in water was diluted to hold 0.0625% v isopropanol in water. The second arrow indicates the first time that flow was directed through the vial containing 0.0625% v isopropanol in water. Flow was subsequently switched a few times between the vial with 0.0625% v isopropanol in water and the vial with 0.225% v isopropanol in water.

Electrical Safety

In accordance with another aspect of the invention, systems, devices and methods are provided that comprise or provide electrical safety features for mitigating risks and adverse effects. Electrical safety is an important consideration for breath analysis devices that interface directly with a user, particularly for devices, e.g., such as measurement device 12 as shown in FIG. 1, wherein there is contact and interaction directly between the device and the user's respiratory tract. Electrical safety considerations include protection against over-voltage, electrostatic discharge, electrical surge, and the like. The use of battery power in breath analysis devices introduces the potential for further issues, e.g., such as battery over-charging, cross-polarity damage, and potentially meltdown or catastrophic failure of a battery pack. These issues are of particular concern in devices that make use of, for example, lithium ion batteries. Additional considerations of an electrical nature include protection from electromagnetic emissions, for example, associated with certain wireless communication components, and the like.

Adverse effects that may be caused by improper or inadequate consideration of electrical safety include, electrolysis of body tissues by passing direct current ("DC") currents directly through body tissues, burns, muscle cramps, respiratory dysfunction or respiratory arrest, cardiac dysfunction or cardiac arrest, including ventricular fibrillation, and the like.

Certain embodiments of nanoparticle sensors are connected to a main power supply, such as a wall socket, capable of supplying alternating current ("AC") directly from the power grid. These devices typically include a power cord, often with an integral grounding wire and grounding pin on the plug. Unfortunately, such devices may be subject to transient power surges from the main power line, AC frequency deviations, spurious line noise, etc. These electrical aberrations may cause circuit board, sensors, and other components of the device to function improperly, be damaged, or cease functioning entirely. For example, power surges may cause electrical shorts, or the like. Power or frequency deviations and line noise may decrease sensor sensitivities, and over-voltage may cause current or thermal run-away on a diode, transistor, or amplifier in the device. These issues can be troublesome and in some instances dangerous, particularly in the case of thermal run-away, because they can cause damage to the device or injury to the user, such as burns, electrical shocks, interference with pacemakers, and the like. Such devices would benefit from use of the safety devices described herein.

Certain embodiments of nanoparticle sensors are connected to a power main, but without a separate ground connection. Alternatively, these sensors may be connected to an auxiliary power supply, such as a Universal Serial Bus ("USB") chipset on a computer, a portable charging pack or power supply, or the like. While the power cord of such devices may be insulated, the lack of grounding can cause challenges to performance and the potential for danger to a user. For example, electrostatic charge may build up on surfaces of the device, and may discharge when the user touches the device. This may be particularly troublesome if the device is in contact with a user's mouth or respiratory tract. Again, such devices would benefit from use of the safety devices described herein.

Other devices may be battery powered. Battery powered devices, while generally safe from the sometimes dramatic power fluctuations associated with main power lines, also have inherent risks. Battery packs, for example, may become extremely hot, which may cause burns to a user. Batteries may also leak corrosive or toxic chemicals and fluids, which is particularly dangerous for embodiments that come into contact with a user's mouth. Other examples, including embodiments that use lithium ion battery packs, may suffer catastrophic failures resulting in explosion, leaking, or combustion of the battery pack and the device. These dangers each pose potential but real threats to the user, and to the device. Furthermore, the power provided by the battery over the charge depletion period may adversely affect sensor and circuit performance. Again, such devices would benefit from use of the safety devices described herein.

There are three main mechanisms by which the user can generate physical harm if the sensor system is not properly designed:

(1) battery leaks or overheats,
(2) power line surges or fast transients from A/C main are not rejected by the sensor system and components of the sensor system, e.g., the processor, are damaged, causing incorrect performance, and
(3) power line surges or fast transients from A/C main are not rejected by the sensor system and components of the sensor system, e.g., the processor, are damaged, causing improper signaling between components (e.g., overheating of a thermistor), which ultimately causes exposure to heavy metals from the nanoparticle sensor itself.

In certain embodiments, the power supply includes an isolation circuit for electrically isolating the devices electrical components from the power supply. An isolation circuit may include one or more isolation capacitors, an isolation transformer, or the like.

Additionally, an embodiment may include a power conditioning circuit configured to regulate the frequency of power supplied to operational components of the device. Such an embodiment, may include a phase-locked loop circuit, a frequency filter circuit, such as a low-pass circuit or band-pass circuit. In such embodiments, frequency anomalies from the main power line, and other power supplies. The present embodiments may further include a current limiting circuit configured to protect device components for electrical surges or from current run-away. The current limiting circuit may include one or more transistors or an amplifier configured in combination with one or more additional components such as resistors and capacitors for detecting when the current draw is over a threshold value, and then restricting or limiting the current supplied. For example, the power supply may be switched off. In another embodiment, a step-down circuit may reduce the voltage supplied by the power supply.

The present embodiments may include thermal sensor circuit configured to detect an over-temperature or thermal run-away condition. The thermal sensor may comprise, for example, a thermistor. In an embodiment, the thermal sensor may be coupled to a comparator circuit for comparing the temperature detected by the thermistor with a threshold value. If the temperature exceeds the threshold, then the power source may be switched off. Alternatively, the current or voltage supplied to the device may be limited by, for example, the current limiting circuit.

Additionally, the present embodiments may include one or more battery safety devices. For example, a battery safety device may include a physically restrictive device, such as an irregularly shaped receptacle for the battery configured to prevent improper installation of the battery. The battery safety device may also include a cross-polarization detection circuit configured to detect when the battery has been inserted incorrectly and to disable the device in response. In still other embodiments, the battery safety device may include a thermal detector configured to monitor the temperature of the battery pack.

Additional embodiments may include a voltage regulator circuit configured to ensure that the power supplied by the battery is within an acceptable range. For example, the voltage regulator circuit may limit the voltage supplied in response to a determination, e.g., with a comparator, that the supplied voltage is above a threshold. In another embodiment, the voltage regulator circuit may switch off power supplied by the battery, for example with a transistor or amplifier circuit, in response to a determination that the voltage supplied by the battery is under a threshold voltage. In certain embodiments, there may be an upper threshold and a lower threshold.

In one embodiment, the battery safety device may include a battery overcharge protection circuit configured to monitor a charging cycle of a battery and to restrict or shut off the charging current in response to a determination that the battery is charged up to a predetermined level. In an embodiment, the battery overcharge protection circuit may monitor a charging time. In another embodiment, the overcharge protection circuit may monitor a current or voltage supplied by the battery during the charge, and determine when the voltage or current exceed a predetermined threshold.

In some embodiments, the device may generate electromagnetic energy, which may interfere with the sensor, or medical equipment in a medical facility. For example, the present embodiments may include a wireless communication chipset or the like. In other embodiments, the power supplied via the power cord may generate electromagnetic energy. In such embodiments, an electromagnetic isolation device may be provided. An embodiment of an electromagnetic isolation device may include electromagnetic shielding of the power cord with, for example, a metal foil, a metallic braid, or the like. In still other embodiments, certain components such as transformers, may be housed in a metallic or other electromagnetically shielding material. In still other embodiments, an electromagnetic isolation circuit may be included, which for example, includes one or more isolation capacitors, resistors, transistors, or the like.

A representative electrical design and configuration for a nanoparticle-based sensor such as those described herein above is illustrated in FIG. 2 for a single heater design, and in FIG. 2 and FIG. 3 for a dual heater design. In the former instance, the nanoparticle-based sensor subsystem comprises a four-terminal device (two leads for the sensor and two for the heater) and, in the latter, a six-terminal device (two lead for the sensor and two for each of the two heaters). This may be reduced, for example, by combining leads, e.g., by using a common power lead or a common ground lead.

Figure 28:
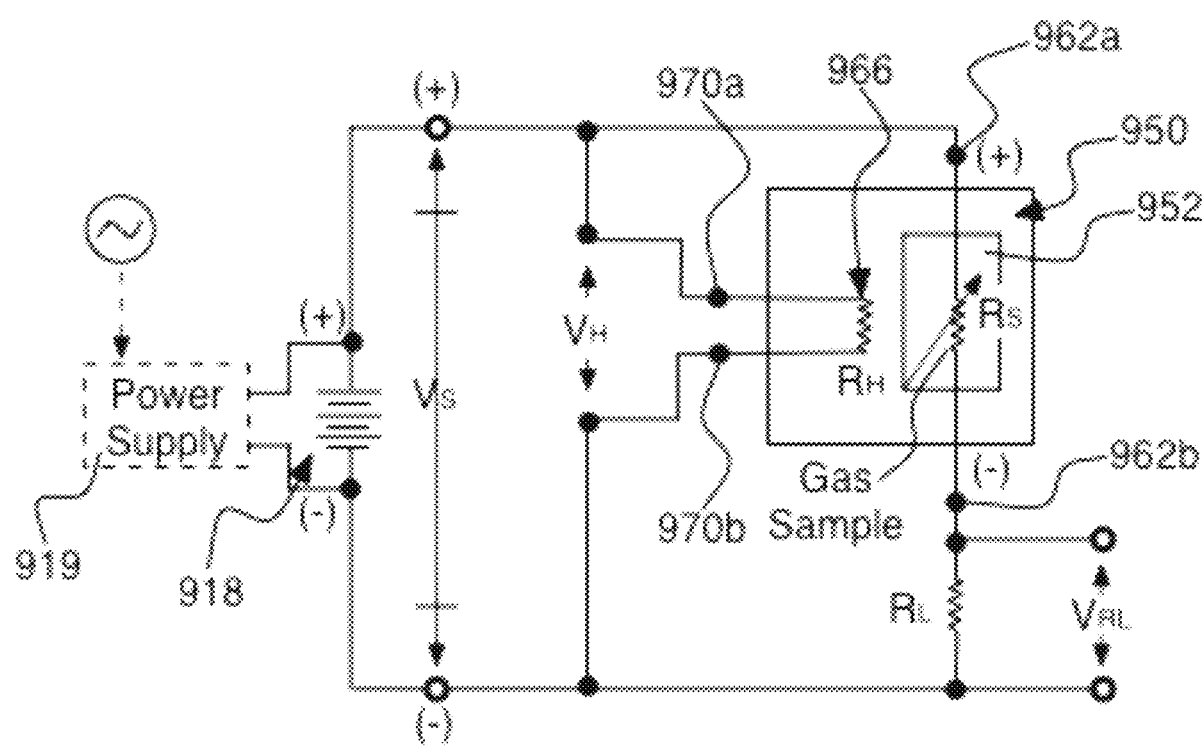
FIG. 28 is an electrical diagram that shows a typical electrical circuit associated with a nanoparticle-based sensor system used in a breath measurement system.

A circuit diagram or schematic illustrating the electrical design and configuration for a nanoparticle-based sensor subsystem such as those described herein above is shown in FIG. 28, which may be used in conjunction with FIG. 2 to better understand this illustrative embodiment. Nanoparticle-based sensor subsystem 950 comprises sensor 952 and heating device 966, corresponding to sensor subsystem 50, sensor 52 and heating device 66 of FIG. 2. The load or resistance of sensor 952 is represented in the drawing by $R_S$ and that of heater 66 is represented by $R_H$. A power supply 918, such as battery pack 18 of FIG. 1, supplies DC power at a sensor voltage $V_S$. To provide DC power to sensor 952, sensor lead 962a (corresponding to lead 62a in FIG. 2) is ohmically coupled to the positive terminal of battery 918. The other sensor lead 962b (corresponding to lead 62b in FIG. 2) is coupled to a load resistor $R_L$ and through it to the negative terminal of battery 918 or, equivalently in this embodiment, to ground. The value of load resistor $R_L$ is selected to optimize the operating characteristics of sensor 952, such as sensitivity and power consumption. Heating device 966 (corresponding to hearing device 66 in FIG. 2) is coupled at its hot lead 970a to the positive terminal of battery 918 and heater lead 970b is coupled to ground, (970a and b here corresponding to leads 70a and b in FIG. 2).

In operation, battery 918 provides power to both sensor 950 and heater 966. The heater raises the temperature of sensor 950 to its operating temperature of about 400° C. When this operating temperature is achieved, the breath sample is passed over or through sensor 950. Acetone in the breath sample selectively adsorbs onto or otherwise interacts with sensor 950 and in the process alters the resistivity RS of the sensor. This change in resistivity is sensed as a change in the voltage or potential difference $V_{RL}$ outputted by sensor 952 at lead 962b relative to ground across load resistor $R_L$. This potential difference $V_{RL}$ comprises a sensor measurement signal that is reflective of the concentration of acetone in the breath sample (marked "gas sample" in FIG. 28).

The representative circuitry for sensor 952 as shown in FIG. 28, although functional, lacks protection from such concerns as over voltage and electrostatic discharge ("ESD"). The problem is even more pronounced where an active power supply, such as an AC-supplied power supply 919 is used, as shown in FIG. 28. With the circuit of FIG. 28, particularly when using active power supply 919, presents risks from power surge, over voltage, over current, ESD, electrical fast transient ("EFT"), and over charging. An over-voltage condition, for example, could cause heating device 966 to overheat, thus potentially threatening risk of injury to the mouth or respiratory tract of the user for a device such as measurement device 12 in FIG. 1. Such overheating also could damage sensor 952.

To address and mitigation risks such as these, a system can be provided that comprises a measurement device for measuring acetone in the breath of a user, and an electronic device operatively coupled to the measurement device, wherein the measurement device comprises protective circuitry. The measurement device itself, including the incorporated protective circuitry, comprises another related but separate aspect of the invention.

In some embodiments, such a system comprises system 10 as shown in FIG. 1 and subsequent figures, and may include the measurement device 12 in FIG. 1 and subsequent figures, both modified to include the protective circuitry features described herein below.

Figure 29:
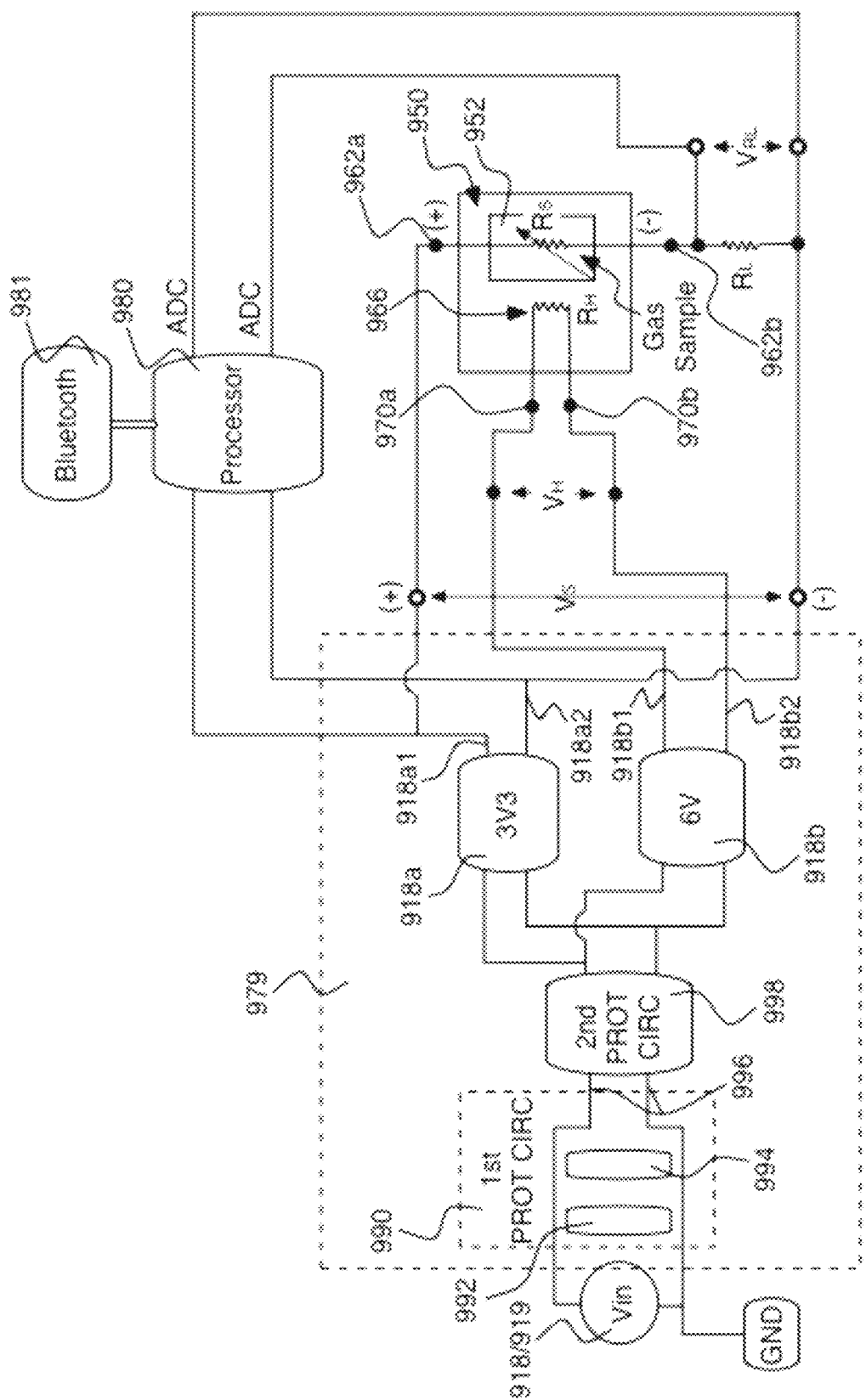
FIG. 29 is an electrical diagram that shows an electrical circuit associated with a nanoparticle-based sensor system.

FIG. 29 shows nanoparticle-based sensor system circuitry as described herein above with respect to FIG. 28, but which comprises protective circuitry 979 that mitigates or eliminates risks of damage or user injury. Protective circuitry 979 is also included in FIG. 1 as circuitry 79, in FIG. 10 as circuitry 279, in FIG. 379 as FIG. 13, in FIG. 15 as circuitry 479, in FIG. 16 as circuitry 579, in FIG. 17 as circuitry 679.

In these embodiments, power is supplied to the circuit by a power supply that may comprise battery pack 918 or AC power supply 919. For purposes of this illustration, the power supply is assumed to be AC power supply 919. Power supply 919 operates on standard AC power and outputs a rectified DC voltage $V_{IN}$.

The circuit may include first protective circuitry 990 that in turn comprises a diode 992 and a capacitor 994. Diode 992 protects the circuit from reverse polarity conditions that could adversely affect system components, e.g., such as sensor 952. Capacitor 994 buffers the circuit from transients and provides protection from EFTs. The output of first protective circuitry is a pair of lines 996 comprising a DC voltage and a ground.

The circuit may include second protective circuitry 998, which provides over voltage protection, over current protection, and ESD protection. Circuitry 998 receives as inputs lines 996 from first protective circuitry 990. The output from circuitry 998 is a pair of lines 999 that comprise a DC voltage and a ground.

The circuitry may include a first voltage regulator 918*a* that in this embodiment provides a steady output voltage of 3 volts ("v"), and a second voltage regulator 918*b* that in this embodiment provides a steady output voltage of 6 v. Each of the voltage regulators 918*a* and 918*b* receives as an input from circuit 998 the DC voltage and ground lines.

Voltage regulator 918*a* has as an output a first output terminal 918*a*1 that represents a high or 3 v line and a second output terminal 918*a*2 that represents a low or ground terminal. Similarly, voltage regulator 918*b* has a first output terminal 918*b*1 that represents a high or 6 v line and a second output terminal 918*a*2 that represents a low potential terminal.

Nanoparticle-based sensor 952 obtains its power from 3-volt regulator 918*a*. High terminal 918*a*1 of regulator 918*a* is coupled to nanoparticle-based sensor lead 962*a* (corresponding to lead 62*a* of FIG. 2). Sensor lead 962*b* is coupled to load resistor $R_L$ and through it to ground 918*a*2. High terminal 918*a*1 also is provided to processor 980 (corresponding to the processor on PCB 80 in FIG. 1), as explained more fully herein below. The output of sensor 952 is provided to processor 980 via coupling to terminal 962*b* and via coupling to ground, across load resistor $R_L$. The sensor measurement signal outputted by sensor 952 and reflective of the concentration of acetone in the breath sample is provided by the voltage or potential difference $V_{RL}$ across these leads.

Heating device 966 obtains its power from 6-volt regulator 918*b*. High terminal 918*b*1 is coupled to lead 970*a* of heater 966 and terminal 918*b*2 is coupled to lead 970*b* of heater 966 (970*a* and *b* here corresponding to leads 70*a* and *b* in FIG. 2).

This circuit embodiment incorporates power protection capabilities in the form of diode 992 (for inverse polarity protection), capacitor 994 (for EFT protection), and second protective circuitry 998 for over voltage and over current conditions and ESD protection. These protective circuit elements can ensure that there is a safe power source for the system.

This circuit embodiment further incorporates voltage regulators to ensure that the power output is clean and stable. This design incorporates multiple regulators to power the heating element as well as the sensor circuit and the other system circuit (for example, the processor) with the option of providing different voltages.

In addition, this embodiment incorporates a microprocessor that is connected across $R_L$ of the sensor circuit. The ends of the $R_L$ resistor are attached to ADC pins on the microprocessor to measure the voltage drop across $R_L$. The processor is also attached to other peripherals that may make use of the sensor output.

Additional advantages and modifications will readily occur to those skilled in the art. For example, although the illustrative embodiments, method implementations and examples provided herein above were described primarily in terms of the conductivity or current state of the conduction paths, one also may monitor or control voltage states, power states, combinations of these, electro-optically, and the like. Therefore, the invention in its broader aspects is not limited to the specific details, representative devices and methods, and illustrative examples shown and described. Accordingly, departures may be made from such details without departing from the spirit or scope of the general inventive concept as defined by the appended claims and their equivalents.

Terminology

Although certain embodiments have been described herein with respect to breath measurement systems and methods for measuring acetone, the systems described herein can detect other analytes, such as oxygen, ketone, ammonia, isoprene, ethanol, isopropanol, and/or carbon dioxide, in addition to or instead of acetone.

Conditional language used herein, such as, among others, "can," "might," "may," "e.g.," and the like, unless specifically stated otherwise, or otherwise understood within the context as used, is generally intended to convey that some embodiments include, while other embodiments do not include, certain features, elements, and/or states. Thus, such conditional language is not generally intended to imply that features, elements, blocks, and/or states are in any way required for one or more embodiments or that one or more embodiments necessarily include logic for deciding, with or without author input or prompting, whether these features, elements and/or states are included or are to be performed in any particular embodiment.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The ranges disclosed herein also encompass any and all overlap, sub-ranges, and combinations thereof. Language such as "up to," "at least," "greater than," "less than," "between," and the like includes the number recited. For example, "about 150° C." includes "150° C." Numbers preceded by a term such as "about," "substantially," or "approximately" include the recited numbers and should be interpreted based on the circumstances (e.g., as accurate as reasonably possible under the circumstances, for example ±1%, ±5%, ±10%, ±15%, etc.).

Although certain embodiments and examples have been described herein, it will be understood by those skilled in the art that many aspects of the delivery systems shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

What is claimed is:

1. A portable measurement device for measuring acetone in a breath sample of a user, the measurement device comprising:
    a housing;
    a mouthpiece for receiving the breath sample from a respiratory tract of the user;
    a flow path disposed within the housing and comprising an upstream end and a downstream end, the upstream end of the flow path being in fluid communication with the mouthpiece, wherein in normal operation of the device the flow path directs the breath sample in a downstream direction from the mouthpiece at the upstream end of the flow path and toward the downstream end;
    a nanoparticle-based sensor disposed in the housing in fluid communication with the flow path and at an intermediate location between the upstream end and the downstream end;
    a temperature sensor disposed in the housing proximate the nanoparticle-based sensor;
    a temperature control circuit connected to the nanoparticle-based sensor to adjust a temperature of the nanoparticle-based sensor; and
    a flow control device disposed in the housing and in the flow path between the upstream end and the downstream end that prevents flow of the breath sample in an upstream direction opposite the downstream direction, the flow control device thereby inhibiting inhalation by the user of gas heated by the nanoparticle-based sensor.

2. A measurement device as recited in claim 1, wherein the nanoparticle-based sensor is substantially inaccessible to the user during use of the device.

3. A measurement device as recited in claim 1, wherein the measurement device further comprises an electrical safety circuit coupled to a power supply and the nanoparticle-based sensor that protects the nanoparticle-based sensor.

4. A measurement device as recited in claim 1, wherein the intermediate location comprises a compartment within the housing that comprises a detachable cover at an external location on the housing, and wherein the detachable cover is secured in a closed position.

5. A measurement device as recited in claim 1, wherein the flow control device comprises a one-way valve.

6. A measurement device as recited in claim 1, further comprising a conditioning device disposed adjacent to the mouthpiece.

7. A measurement device as recited in claim 1, further comprising a processor coupled to the nanoparticle-based sensor for receiving a measurement signal representative of a concentration of the acetone in the breath sample from the nanoparticle-based sensor.

8. A system for sensing an analyte in a breath sample of a user, the system comprising:
    a housing,
    a mouthpiece for receiving the breath sample from a respiratory tract of the user,
    a flow path disposed within the housing and comprising an upstream end and a downstream end, wherein during exhalation of the breath sample by the user into the mouthpiece the breath sample flows in the flow path in a downstream direction from the upstream end toward the downstream end,
    a nanoparticle-based sensor disposed in the housing in fluid communication with the flow path and at an intermediate location between the upstream end and the downstream end,
    a temperature sensor disposed in the housing proximate the nanoparticle-based sensor;
    a temperature control circuit connected to the nanoparticle-based sensor to adjust a temperature of the nanoparticle-based sensor; and
    a flow control device that inhibits inhalation by the user of gas heated by the nanoparticle-based sensor by inhibiting gas flow in an upstream direction in the flow path.

9. The system of claim 8, wherein the flow control device comprises a one-way valve.

10. The system of claim 8, wherein the analyte is acetone.

11. A portable device capable of measuring a concentration of an analyte in a breath sample of a user, the portable device comprising:
    a mouthpiece;
    a housing;
    a conduit formed within the housing and fluidly coupled to the mouthpiece at an upstream end, the conduit forming a flow path through which the breath sample flows in a downstream direction during exhalation by the user into the mouthpiece;
    a nanoparticle-based sensor positioned along the flow path, the nanoparticle-based sensor capable of measuring the concentration of the analyte in the breath sample;
    a heating device that heats the nanoparticle-based sensor; and
    a flow control device that inhibits a flow of gas in the conduit in an upstream direction opposite the downstream direction, the flow control device thereby inhibiting inhalation by the user of gas heated by the nanoparticle-based sensor.

12. The portable device of claim 11, wherein the nanoparticle-based sensor is a metal oxide semiconductor sensor.

13. The portable device of claim 11, wherein the flow control device comprises a one-way valve.

14. The portable device of claim 11, wherein the analyte is acetone.

\* \* \* \* \*